US009926373B2

(12) United States Patent
Andersen et al.

(10) Patent No.: US 9,926,373 B2
(45) Date of Patent: Mar. 27, 2018

(54) HUMAN CD30 LIGAND ANTIGEN BINDING PROTEINS

(71) Applicants: Novo Nordisk A/S, Bagsvaerd (DK); Amgen Inc., Thousand Oaks, CA (US)

(72) Inventors: Mette D. Andersen, Vaerloese (DK); Jeff Dantzler, Seattle, WA (US); Richard J. Armitage, Bainbridge Island, WA (US); Rutilio Clark, Bainbridge Island, WA (US)

(73) Assignees: Novo Nordisk A/S, Bagsvaerd (DK); Amgen Inc., Thousand Oaks, CA (US)

( * ) Notice: Subject to any disclaimer, the term of this patent is extended or adjusted under 35 U.S.C. 154(b) by 143 days.

(21) Appl. No.: 14/396,248

(22) PCT Filed: Apr. 25, 2013

(86) PCT No.: PCT/US2013/038135
§ 371 (c)(1),
(2) Date: Oct. 22, 2014

(87) PCT Pub. No.: WO2013/163377
PCT Pub. Date: Oct. 31, 2013

(65) Prior Publication Data
US 2016/0039940 A1    Feb. 11, 2016

Related U.S. Application Data

(60) Provisional application No. 61/639,637, filed on Apr. 27, 2012.

(51) Int. Cl.
*A61K 38/00* (2006.01)
*C07K 16/28* (2006.01)
*C07K 14/705* (2006.01)
*A61K 39/00* (2006.01)

(52) U.S. Cl.
CPC .... *C07K 16/2875* (2013.01); *C07K 14/70575* (2013.01); *A61K 2039/505* (2013.01); *C07K 2317/21* (2013.01); *C07K 2317/34* (2013.01); *C07K 2317/55* (2013.01); *C07K 2317/565* (2013.01); *C07K 2317/732* (2013.01); *C07K 2317/76* (2013.01); *C07K 2317/92* (2013.01); *C07K 2319/21* (2013.01); *C07K 2319/43* (2013.01); *C07K 2319/50* (2013.01)

(58) Field of Classification Search
None
See application file for complete search history.

(56) References Cited

U.S. PATENT DOCUMENTS 5,480,981 A    1/1996  Goodwin et al.
5,567,440 A *  10/1996 Hubbell ............... A61K 9/5031
                                                    424/484
5,677,430 A *  10/1997 Goodwin ............ C07K 14/70575
                                                    530/387.9
5,840,869 A    11/1998 Mosley et al.
6,143,869 A    11/2000 Goodwin et al.
6,652,854 B2   11/2003 Mohler et al.
6,667,039 B1   12/2003 Goodwin et al.
2005/0163747 A1* 7/2005 Hilbert ................. C07K 14/525
                                                    424/85.1
2015/0274827 A1* 10/2015 Pfizenmaier ..... C07K 14/70575
                                                    424/134.1

FOREIGN PATENT DOCUMENTS

EP          460846 B1    2/2002
JP       2005021110 A    1/2005
WO         9324135 A1   12/1993
WO         9940187 A1    8/1999
WO         0211767 A2    2/2002

OTHER PUBLICATIONS

Blazar et al. CD30/CD30 Ligand (CD153) Interaction Regulates CD4-T Cell-Mediated Graft-versus-Host Disease. The Journal of Immunology, 2004, 173: 2933-2941.*
Campbell A, General properties and applications of monoclonal antibodies, Elsevier Science Publishers, section 1.1, pp. 1-32, 1984.*
Oflazoglu et al. Targeting CD30/CD30L in Oncology and Autoimmune and Inflammatory Diseases. Therapeutic Targets of the TNF Superfamily. vol. 647 of the series Advances in Experimental Medicine and Biology pp. 174-185, Edited by Iqbal S. Grewal, 2009.*
Vajdos et al. Comprehensive functional maps of the antigen-binding site of an anti-ErbB2 antibody obtained with shotgun scanning mutagenesis. J. Mol. Biol. 2002, Jul. 5, 320(2):415-28.*
Brown et al. Tolerance of single, but not multiple, amino acid replacements in antibody VH CDR 2: a means of minimizing B cell wastage from somatic hypermutation? J. Immuno. May 1996, 3285-91.*
Van Regenmortel MHV. Mapping Epitope Structure and Activity: From One-Dimensional Prediction to Four-Dimensional Description of Antigenic Specificity Methods. 9(3):465-72, 1996.*
Gruss et al. CD30 Ligand Expression in Nonmalignant and Hodgkin's Disease-involved Lymphoid Tissues. American Journal ofPathology, vol. 149, No. 2, Aug. 1996.*
Bruce B et al. CD30/CD30 Ligand (CD153) Interaction Regulates CD4 +T Cell-mediated Graft-versus-Host Disease, The Journal of Immunology.2004,vol. 173, No. 5 ,pp. 2933-2941.
S. Chakrabarty et al.,Critical roles of CD38/CD38L interactions in murine auto immune diabetes,Clinical & Experimental Immunology, 2003, vol. 133, No. 3, pp. 318-325.

(Continued)

Primary Examiner — Maher M Haddad
(74) Attorney, Agent, or Firm — Fangli Chen; Proskauer Rose LLP

(57) ABSTRACT

Provided are compositions and methods relating to human CD30L antigen binding proteins. Compositions described herein include: human CD30L antigen binding proteins, polynucleotides encoding human CD30L antigen binding proteins, vectors comprising these polynucleotides, host cells, and pharmaceutical compositions. Methods of making and using each of these compositions are also provided.

6 Claims, 2 Drawing Sheets

(56) References Cited

OTHER PUBLICATIONS

Figure 1A:
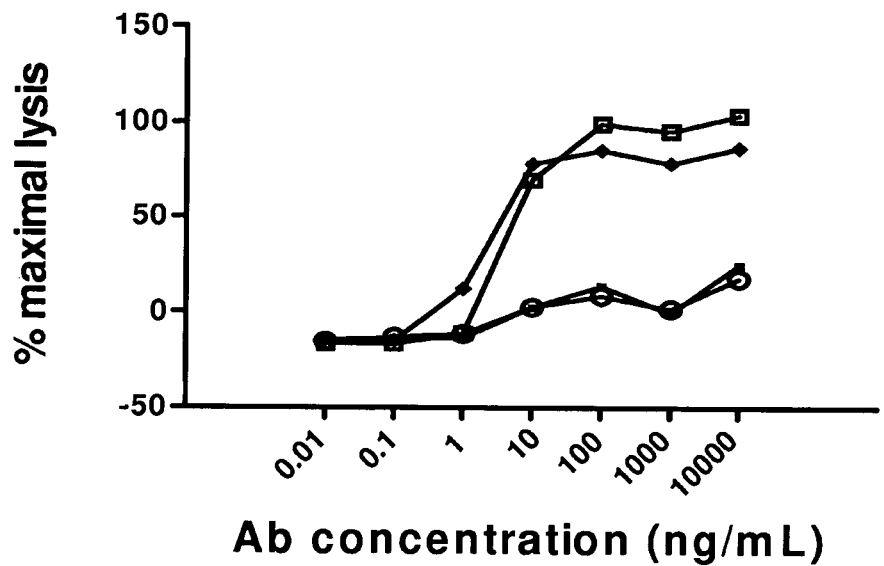

Saraiva M et al. Inhibition of Type 1 Cytokine-Mediated Inflammation by a Soluble CD30 Homologue Encoded by Ectromelia (Mousepox) Virus, The Journal of Experimental Medicine Rockefeller University Press, US, 2002, vol. 196, No. 6, pp. 829-839.
Polte et al., Direct evidence for a critical role of CD30 in the development of allergic asthma, Journal of Allergy and Clinical Immunology,Elsevier,Amsterdam, 2006, vol. 118, No. 4, pp. 942-948.
Kennedy M K et al., Deciphering CD30 ligand biology and its role in humoral immunity, Immunology, 2006 vol. 118, No. 2, pp. 143-152.
Fischer M et al., "Mast cell CD30 ligand is upregulated in cutaneous inflammation and mediates degranulation-independent chemokine secretion", Journal of Clinical Investigation, 2006, vol. 116, No. 10, pp. 2748-2756.
Franke A C et al., Characterization of the CD30L binding domain on the human CD38 antibodies, Hybridoma, Liebert, New York, NY, US, 2000, vol. 19, No. 1, pp. 43-48.
Durkop et al,Molecular Cloning and Expression of a New Member of the Nerve Growth Factor Receptor Family That is Characteristic for Hodgkin's Disease , Journal Cell,Year 1992 vol. 68 pp. 421-427.
Smith et al,CD30 Antigen, a Marker for Hodgkin's Lymphoma,Is a Receptor Whose Ligand Defines an Emerging Family of Cytokines with Homology to TNF, Journal :Cell,Year 1993, vol. 73. pp. 1349-1360.
Ellis et al., CD30 is a Signal-Transducing Molecule that Defines a Subset of Human Activated CD45RO T Cells, Journal : Journal of Immunology, Year Sep. 1, 1993 ,vol. 151, No. 5, pp. 2380-2389.
Falini et al, CD30 (Ki-l) Molecule: A New Cytokine Receptor of the Tumor Necrosis Factor Receptor Superfamily as a Tool for Diagnosis and Immunotherapy, Journal :Blood. Year 1995, vol. 85, No. 1, pp. 1-14.
Shimozato et al,Expression of CD30 Ligand (CD153) on Murine Activated T Cells, Journal :Biochemical and Biophysical Research Communications, Year 1999, vol. 256 , pp. 519-526.
Armitage R J.CD153,Journal :Journal of Biological Regulators and Homeostatic Agents, Year 2000, vol. 14. pp. 142-144.
Klein et al.Transcriptional analysis of the B cell germinal center reaction, Journal :Proceedings of the National Academy of Sciences USA, Year 2003, vol. 100, No. 5, pp. 2639-2644.
Kim et al.,CD4CD3 Accessory Cells Costimulate Primed CD4 T Cells through OX40 and CD30 at Sites Where T Cells Collaborate with B Cells, Journal :Immunity,Year 2003, vol. 18, pp. 643-654.
Shanebeck et al,Regulation of murine B cell growth and differentiation by CD30 ligand, Journal :European Journal of Immunology, Year 1995, vol. 25, pp. 2147-2153.
Gaspal et al, Mice Deficient in OX40 and CD30 Signals Lack Memory Antibody Responses because of Deficient CD4 T Cell Memory, Journal:Immunology, Year 2005, vol. 174, pp. 3891-3896.
Mori L et al: "Attenuation of collagen-induced arthritis in 55-kDa TNF receptor type 1 (TNFR1)-IgG1-treated and TNFR1-deficient mice."Journal:Journal of Immunology Year Oct. 1, 1996,vol. 157, No. 7,pp. 3178-3182.
Blom Abet Al: "Immune complexes, but not streptococcal cell walls or zymosan, cause chronic arthritis in mouse strains susceptible for collagen type II auto-immune arthritis."Journal :Cytokine. Year Dec. 1999,vol. 11, No. 12, pp. 1046-1056.
Gruss H et al, Biological roles of CD30 ligand in CD30+ malignant lymphomas and T cell-dependent immune responses. Journal :Experimental Hematology (Charlottesville),Year 1995, vol. 23, No. 8, p. 851.
Peschon J et al: "TNF receptor-deficient mice reveal divergent roles for p55 and p75 in several models of inflammation"Journal :Journal of Immunology, Year Jan. 15, 1998 vol. 160, pp. 943-952.
Wiley et al., "Reverse Signaling via CD30 Ligand," The Journal of Immunology, 1996, vol. 157, No. 8, pp. 3635-3639.
Zhao et al., PLOSone, Structural and Functional Analysis of Multi-Interface Domains, Dec. 2012, vol. 7 (12), pp. 1-13.
Yarlin A.A., "Osnovi Immunologii", Fundamentals of Immunology, M.:Medicine, 1999, pp. 172-174.

\* cited by examiner

HUMAN CD30 LIGAND ANTIGEN BINDING PROTEINS

CROSS-REFERENCE TO RELATED APPLICATIONS

This application is a 35 U.S.C. § 371 National Stage application of International Application PCT/US2013/038135 (WO 2013/163377), filed Apr. 25, 2013, which claims priority under 35 U.S.C. § 119 of U.S. Provisional Application 61/639,637; filed Apr. 27, 2012.

SEQUENCE LISTING

The instant application contains a Sequence Listing which has been submitted in ASCII format via EFS-Web and is hereby incorporated by reference in its entirety. Said ASCII copy, created on Apr. 23, 2013 and amended Mar. 15, 2017, is named 8679US01_SeqListing_ST25.txt and is 53,306 bytes in size.

BACKGROUND

CD30 ligand (CD30L, CD153), the naturally occurring ligand for CD30, is a type II membrane glycoprotein that specifically binds CD30, triggering CD30 to transmit a signal via its cytoplasmic domain. CD30 and CD30L are interacting cell surface glycoproteins that are members of the TNFR and TNF superfamilies, respectively (Durkop et al, Cell, 68:421, 1992; Smith et al, Cell, 73:1349, 1993; U.S. Pat. Nos. 5,480,981; 5,677,430; 6,143,869 and 6,652,854). The expression of CD30 and CD30L is restricted to cells of the immune system and is tightly regulated. CD30 is expressed primarily on activated B cells and subsets of T cells with an activated/memory phenotype (Ellis et al., J. Immun., 151:2380, 1993; Falini et al., Blood, 85:1, 1995). CD30L is expressed at high levels on activated mouse and human T cells (Shimozato et al, Biochem. & Biophys. Res. Comm., 256:519, 1999; Armitage, J. Biological Regulators & Homeostatic Agents, 14:142, 2000). Dramatic changes in the relative gene expression of CD30L occur as B cells transit through germinal centers (Klein et al, Proc. Nat. Acad. Sci., USA, 100:2639, 2003). Thus the expression of CD30L on B cells may be stage and context specific. CD30L also appears to be a marker of a unique population of mouse dendritic cell-like accessory cells that are present in the splenic follicles where T cells interact with B cells (Kim et al., Immunity, 18:643, 2003).

Interactions between cells expressing CD30/CD30L appear to be important for the generation of strong T-cell dependent secondary or class-switched antibody responses. Evidence for such a role includes data from in vitro (Shanebeck et al., Eur. J. Immunol., 25:2147-53, 1995) and in vivo (Gaspal et al., J. Immunol., 174:3891-6, 2005) studies in mouse systems. In addition, it has been shown that in vivo treatment of mice with a blocking, but non-depleting, rat mAb to mouse CD30L inhibits the development or progression of disease in a number of models of T and/or B cell-dependent autoimmune diseases (U.S. Pat. No. 6,667,039). In models with a strong humoral immune component, inhibition of disease correlates with inhibition of the disease-associated antibody response.

Therefore it would be useful to have compositions comprising human antibodies and/or antigen binding regions that bind to CD30L for use in therapeutic and diagnostic applications

SUMMARY OF THE INVENTION

Antigen binding proteins that bind CD30L, particularly human CD30L are provided. The human CD30L antigen binding proteins can reduce, inhibit, interfere with, and/or modulate at least one of the biological responses related to a CD30L/CD30 interaction, and as such, are useful for ameliorating the effects of CD30L-related diseases or disorders. CD30L antigen binding proteins can be used, for example, to reduce, inhibit, interfere with and/or modulate CD30L/CD30 interactions.

In one embodiment an isolated antigen binding proteins that binds a C-terminal region of CD30L including AA 201-234. In a further embodiment is provided an antigen binding protein that binds a C-terminal region of CD30L including AA 201-234 and a further region of CD30L located in the N-terminal part of the extracellular region, which is defined by AA 75-95. In further embodiments of the invention the antigen binding protein has at least one property selected from the group consisting of: a) inhibiting CD30/CD30L interaction; b) inhibiting CD30L-induced IL-8 induction; c) cross-competing with one of antibodies A-F for binding to human CD30L; d) a dissociation constant to human CD30L is at most 70 pM and e) binding to human CD30L with substantially the same or higher affinity (lower $K_D$) as one of antibodies A-F. The affinity (or $K_D$) may be determined as known by the person skilled in the art, such as by SPR or by FACS as described in Example 4 herein.

In a further embodiment the antigen binding protein binds CD30L, and competes with a Fab of one or more of antibodies A, B, C, D, E and F for binding to CD30L. Alternatively said antigen binding protein is characterized as an antigen binding proteins which binding to hCD30L is inhibited by binding of a Fab of one or more of antibodies A, B, C, D, E and F. In a further specified embodiment the Fab is a Fab of antibody A including each of A1, A2, A3, A4, A5 and A6.

In one embodiment is provided an isolated antigen binding protein that binds CD30L, comprising at least one heavy chain variable region comprising a CDRH1, a CDRH2 and a CDRH3 selected from the group consisting of: a) a CDRH1 that differs by no more than four, three, two or one amino acid substitutions, insertions or deletions from a CDRH1 as shown in TABLE 3; b) a CDRH2 that differs by no more than seven, six, five, four, three, two or one amino acid substitutions, insertions and/or deletions from a CDRH2 as shown in TABLE 3; c) a CDRH3 that differs by no more than eleven, ten, nine, eight, seven, six, five, four, three, two or one amino acid substitutions, insertions and/or deletions from a CDRH3 as shown in TABLE 3; and comprising at least one light chain variable region comprising a CDRL1, a CDRL2 and a CDRL3 selected from the group consisting of: d) a CDRL1 that differs by no more than four, three, two or one amino acid substitutions, insertions and/or deletions from a CDRL1 as shown in TABLE 3; e) a CDRL2 that differs by no more than two or one amino acid substitution, insertion or deletion from a CDRL2 as shown in TABLE 3; f) a CDRL3 that differs by no more than two or one amino acid substitution, insertion or deletion from a CDRL3 as shown in TABLE 3. In a related embodiment is provided a CDRH1 selected from the group consisting of SEQ ID NOs:14, 15, 16, 17, 18, and 33; a CDRH2 selected from the group consisting of SEQ ID NOs: 19, 20, 21, 22, 23, 24 and 34; a CDRH3 selected from the group consisting of SEQ ID NOs: 25, 26, 27, 28, 29, and 35; a CDRL1 selected from the group consisting of SEQ ID NOs: 1, 2, 3, 4, 5, 6, and 30; a CDRL2 selected from the group consisting of SEQ ID NOs: 7, 8, 9, 10, and 31; and a CDRL3 selected from the group consisting of SEQ ID NOs: 11, 12, 13, and 32.

Another embodiment provides an isolated antigen binding protein that binds human CD30L comprising at least one light chain variable region comprising a CDR1, CDR2 and CDR3, wherein the CDR1 comprising amino acid residues 23-36, the CDR2 comprising 52-58 and the CDR3 comprising 91-100 of SEQ ID NOs:36, 28, 40, 42, or 44; or b) a light chain variable region comprising a CDR1, CDR2 and CDR3, wherein the CDR1 comprising amino acid residues 25-36, the CDR2 comprising amino acid residues 52-58 and the CDR3 comprising amino acid residues 91-100 of SEQ ID NO:46; and at least one heavy chain variable region comprising a CDR1, CDR2 and CDR3, wherein the CDR1 comprising amino acid residues 31-35, the CDR2 comprising amino acid residues 50-65 and the CDR3 comprising amino acid residues 98-113 of SEQ ID NOs:48, 50, 52, 54, 56, 58, 60, 62, 64, 66, 68, 70 or 72. In a related embodiment is provided an antigen binding protein that comprises at least one heavy chain variable region and at least one light chain variable region. In another embodiment is provided an antigen binding protein that comprises at least two heavy chain variable regions and at least two light chain variable regions.

In another embodiment is provided an isolated antigen binding protein that binds CD30L comprising a heavy chain variable region and a light chain variable region, wherein the heavy chain variable region sequence differs by no more than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions and/or deletions from a heavy chain variable region sequence as shown in TABLE 2; and wherein the light chain variable region sequence differs by no more than 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid substitutions, additions and/or deletions from a light chain variable region sequence as shown in TABLE 1.

Another embodiment provides an isolated antigen binding protein that binds CD30L comprising a heavy chain variable region comprising of an amino acid sequence having at least 80% sequence identity to SEQ ID NO:48, 50, 52, 54, 56, 58, 60, 62, 64, 66, 68, 70, and 72; and a light chain variable region comprising an amino acid sequence having at least 88% sequence identity to SEQ ID NO: 36, 38, 40, 42, 44, and 46.

In one embodiment is provided an isolated antigen binding protein that binds CD30L selected from the group consisting of a) a heavy chain variable region selected from the group consisting of of SEQ ID NOs:48, 50, 52, 54, 56, 58, 60 and 62 and a light chain variable region of SEQ ID NO: 36; b) a heavy chain variable region of SEQ ID NO:64 and a light chain variable region of SEQ ID NO:38; c) a heavy chain variable region of SEQ ID NO:66 and a light chain variable region of SEQ ID NO:40; d) a heavy chain variable region of SEQ ID NO:68 and a light chain variable region of SEQ ID NO:42; e) a heavy chain variable region of SEQ ID NO:70 and a light chain variable region of SEQ ID NO:44; and f) a heavy chain variable region of SEQ ID NO:72 and a light chain variable region of SEQ ID NO:46. In a related embodiment, the isolated antigen binding protein is an antibody. In yet another related embodiment the antibody is a monoclonal antibody, a recombinant antibody, a human antibody, a humanized antibody, a chimeric antibody, a multispecific antibody, or an antibody fragment thereof. In a further embodiment the antibody fragment is a Fab fragment, a Fab' fragment, a F(ab')$_2$ fragment, a Fv fragment, a diabody, or a single chain antibody molecule. In a related embodiment the antigen binding protein is a human antibody. In yet another related embodiment the antigen binding protein is a monoclonal antibody. In a further related embodiment the antigen binding protein is of the IgG1-, IgG2- IgG3- or IgG4-type. In a related embodiment the antigen binding protein is of the IgG1- or IgG2-type.

Another embodiment provides isolated nucleic acid molecules encoding an antigen binding protein as described above. In a related embodiment at least one heavy chain variable region is encoded by an isolated nucleic acid molecule selected from the group consisting of SEQ ID NOs:49, 51, 53, 55, 57, 59, 61, 63, 65, 67, 69, 71 and 73 and at least one light chain variable region is encoded by an isolated nucleic acid molecule selected from the group consisting of SEQ ID NOs: 37, 39, 41, 43, 45, and 47. In another related embodiment the nucleic acid molecule is operably linked to a control sequence. In a further related embodiments are provided vectors comprising a nucleic acid described above and host cells comprising such vectors. Within yet a further embodiment is provided an isolated polynucleotide sufficient for use as a hybridization probe, PCR primer or sequencing primer that is a fragment of the nucleic acid molecule as described above or its complement.

Another embodiment provides a method of making the antigen binding protein as described above comprising the step of preparing the antigen binding protein from a host cell that secretes the antigen binding protein.

Another embodiment provides an isolated antigen binding protein as described above wherein the antigen binding protein has at least one property selected from the group consisting of: a) inhibiting CD30/CD30L interaction; b) inhibiting CD30L-induced IL-8 induction; c) cross-competing with one of antibodies A-F for binding to human CD30L; d) a dissociation constant ≤70 pM and e) binding to human CD30L with substantially the same Kd as one of antibodies A-F.

In yet another embodiment is provided a pharmaceutical composition comprising at least one antigen binding protein as described above and pharmaceutically acceptable excipient. A related embodiment further provides such pharmaceutical compositions further comprising a labeling group or an effector group. In another related embodiment the labeling group is selected from the group consisting of isotopic labels, magnetic labels, redox active moieties, optical dyes, biotinylated groups and predetermined polypeptide epitopes recognized by a secondary reporter. In a further related embodiment the effector group is selected from the group consisting of a radioisotope, radionuclide, a toxin, a therapeutic group and a chemotherapeutic group. In another related embodiment the antigen binding protein is coupled to a labeling group.

Another embodiment provides a method for treating or preventing a condition associated with CD30L in a patient, comprising administering to a patient in need thereof an effective amount of at least one isolated antigen binding protein as described above. In still another related embodiment the isolated antigen-binding protein is administered alone or as a combination therapy.

Another embodiment provides a method of reducing CD30L activity in a patient comprising administering an effective amount of at least one antigen binding protein as described above.

In yet another embodiment is provided an antigen binding proteins that competes with at least one antigen binding protein as described above.

In another embodiment is provided an antigen binding protein as described above that is fully or partially afucosylated.

FIGURES

FIG. 1A Ramos cells and NK effectors, Open squares: Rituxan (IgG1), Closed diamonds: Antibody A1 IgG1f, Closed squares: Antibody A1 IgG1, Open circles: Antibody A1 IgG2.

Figure 1B:
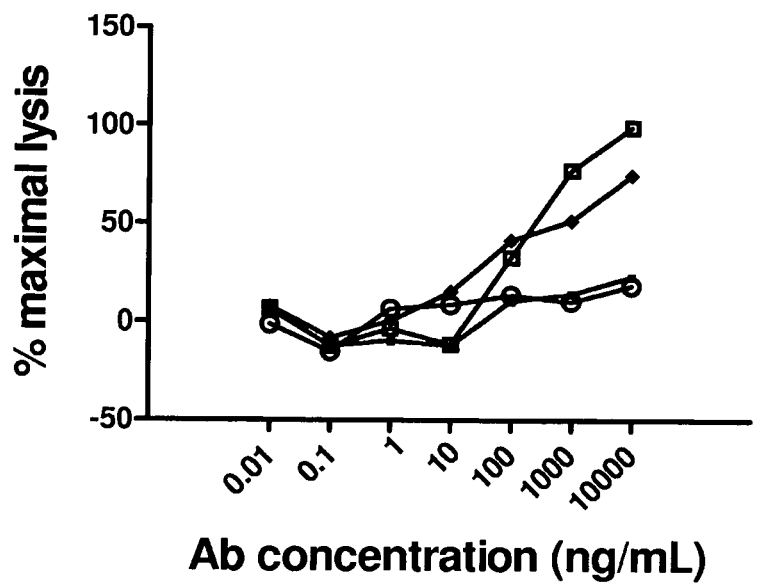

FIG. 1B JD38 cells and NK effectors, Open squares: Rituxan (IgG1), Closed diamonds: Antibody A1 IgG1f, Closed squares: Antibody A1 IgG1, Open circles: Antibody A1 IgG2.

Figure 1C:
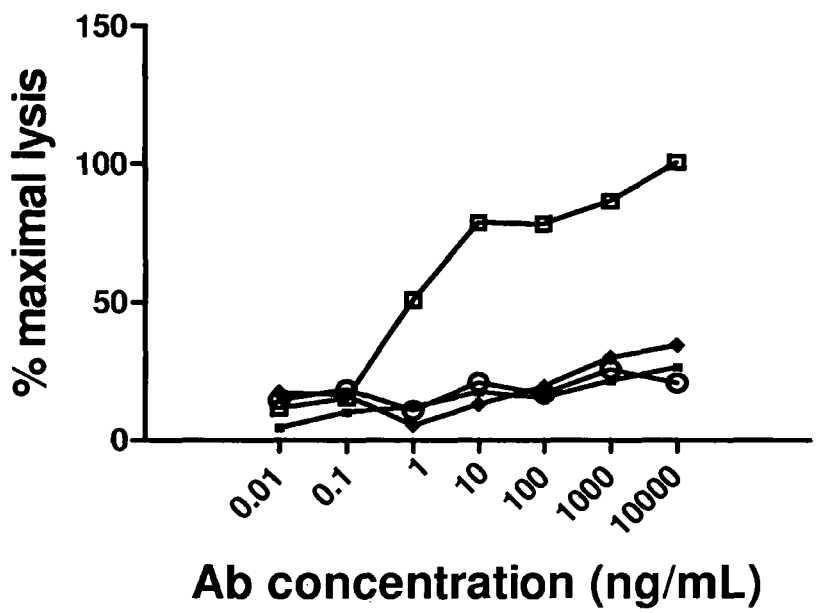

FIG. 1C DS179 cells and NK effectors, Open squares: Rituxan (IgG1), Closed diamonds: Antibody A1 IgG1f, Closed squares: Antibody A1 IgG1, Open circles: Antibody A1 IgG2.

Figure 1D:
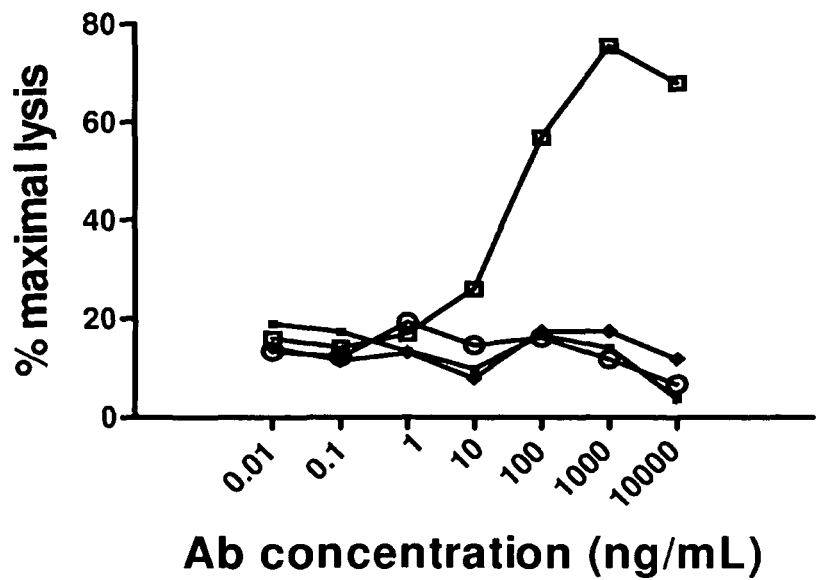

FIG. 1D EW36 cells and NK effectors, Open squares: Rituxan (IgG1), Closed diamonds: Antibody A1 IgG1f, Closed squares: Antibody A1 IgG1, Open circles: Antibody A1 IgG2.

DETAILED DESCRIPTION

The present invention provides compositions, kits, and methods relating to CD30L antigen binding proteins, including antigen binding proteins that block the interaction between CD30L and CD30, such as anti-CD30L antibodies, antibody fragments, and antibody derivatives, e.g., neutralizing anti-CD30L antibodies, antibody fragments, or antibody derivatives. Also provided are polynucleotides, and derivatives and fragments thereof, comprising a sequence of nucleic acids that encodes all or a portion of a polypeptide that binds to CD30L, e.g., a polynucleotide encoding all or part of an anti-CD30L antibody, antibody fragment, or antibody derivative, plasmids and vectors comprising such nucleic acids, and cells or cell lines comprising such polynucleotides and/or vectors and plasmids. The provided methods include, for example, methods of making, identifying, or isolating CD30L antigen binding proteins, such as anti-CD30L antibodies, methods of determining whether a molecule blocks the interaction between CD30L and CD30, methods of determining whether a molecule antagonizes CD30L, methods of making compositions, such as pharmaceutical compositions, comprising a CD30L antigen binding protein, and methods for administering a CD30L antigen binding protein to a subject, for example, methods for treating a condition mediated by CD30L, and for blocking the interaction between CD30L and CD30, in vivo or in vitro.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

All documents, or portions of documents, cited in this application, including but not limited to patents, patent applications, articles, books, and treatises, are hereby expressly incorporated by reference in their entirety for the purpose of describing and disclosing, for example, the methodologies described in such publications that might be used in connection with information described herein.

The term "CD30-ligand" (CD30L) refers to a genus of polypeptides which are capable of binding CD30, as disclosed in Smith et al., *Cell* 73:1349-1360, 1993 and U.S. Pat. No. 5,480,981, including CD30-binding muteins thereof; such polypeptides include membrane-bound proteins (comprising a cytoplasmic domain, a transmembrane region, and an extracellular domain) as well as truncated proteins that retain the CD30-binding property. Such truncated proteins include, for example, soluble CD30L comprising only the extracellular (receptor binding) domain. Also included are CD30L fragments, including portions of a full-length CD30L polypeptide that retains the ability to bind to CD30, or that are capable of eliciting an antibody that binds specifically with a CD30 polypeptide or to a portion of full-length CD30 that is capable of transmitting a biological signal such as activation of NF-κB.

The term "CD30" refers to a receptor that is a member of the TNF/NGF receptor superfamily, the cloning of which is described in Durkop et al. (*Cell* 68:421, 1992). The phrase "soluble CD30" (sCD30) refers to soluble molecules that comprise all or part of the extracellular domain of the CD30 protein, and that retain the capacity to bind specifically with CD30L. Soluble CD30 polypeptides encompass recombinant sCD30 and naturally occurring sCD30 proteins in highly purified form.

As used herein, the phrase "fragment of CD30" refers to a portion of a full-length CD30 polypeptide that retains the ability to bind to CD30L or that is capable of eliciting an antibody that binds specifically with a CD30 polypeptide or to a portion of full-length CD30 that is capable of transmitting a biological signal such as activation of NF-κB.

The phrase "CD30/CD30L interaction" as used herein refers to the specific binding of CD30 to CD30L, resulting in signal transduction by CD30. This includes instances in which at least one binding partner is a fragment of either CD30 or CD30L, that is, the term may refer to the binding interaction of a CD30 fragment to CD30L, CD30 to a CD30L fragment, or a CD30 fragment to a CD30L fragment. In addition, a CD30/CD30L interaction can involve an analog of CD30 (such as an allelic variant or mutein) that is capable of binding specifically to CD30L, or may involve an analog of CD30L (such as an allelic variant or mutein) that can bind specifically with CD30. Moreover, a CD30/CD30L interaction can involve either endogenous CD30 or CD30L proteins or may involve recombinant CD30 or CD30L expressed by a cell transfected with a nucleic acid encoding the recombinant protein.

The term "polynucleotide" includes both single-stranded and double-stranded nucleic acids and includes genomic DNA, RNA, mRNA, cDNA, or synthetic origin or some combination thereof which is not associated with sequences normally found in nature. Isolated polynucleotides comprising specified sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 100 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene.

Oligonucleotides may be sense or antisense oligonucleotides. An oligonucleotide can include a detectable label, such as a radiolabel, a fluorescent label, a hapten or an antigenic label, for detection assays. Oligonucleotides may be used, for example, as PCR primers, cloning primers or hybridization probes.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having one or more deletions from, insertions to, and/or substitutions of the amino acid residues of the native sequence. The term also includes amino acid polymers in which one or more amino acids are chemical analogs of a corresponding naturally-occurring amino acid and polymers. The terms "polypeptide" and "protein" encompass CD30L antigen binding proteins (such as antibodies) and sequences that have one or more deletions from, additions to, and/or substitutions of the amino acid residues of the antigen binding protein sequence. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about five to 500 amino acids long. For example, fragments may be at least 5, 6, 7, 8, 9, 10, 11, 12, 13, 14, 15, 16, 17, 18, 19, 20, 50, 70, 100, 110, 150, 200, 250, 300, 350, 400, or 450 amino acids long. Useful polypeptide fragments include immunologically functional fragments of antibodies, including binding domains. In the case of a CD30L antigen binding protein, such as an antibody, useful fragments include but are not limited to one or more CDR regions, a variable domain of a heavy or light chain, a portion of an antibody chain, a portion of a variable region including less than three CDRs, and the like.

"Amino acid" includes its normal meaning in the art. The twenty naturally-occurring amino acids and their abbreviations follow conventional usage. See, Immunology-A Synthesis, 2nd Edition, (E. S. Golub and D. R. Gren, eds.), Sinauer Associates: Sunderland, Mass. (1991). Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides. Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

The term "isolated protein" refers to a protein, such as an antigen binding protein (an example of which could be an antibody), that is purified from proteins or polypeptides or other contaminants that would interfere with its therapeutic, diagnostic, prophylactic, research or other use. As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In certain embodiments, an essentially homogeneous substance has been purified to such a degree that contaminating species cannot be detected in the composition by conventional detection methods and thus the composition consists of a single detectable macromolecular species.

A "variant" of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins. A "derivative" of a polypeptide is a polypeptide that has been chemically modified in some manner distinct from insertion, deletion, or substitution variants, e.g., via conjugation to another chemical moiety.

The terms "naturally occurring" or "native" as used throughout the specification in connection with biological materials such as polypeptides, nucleic acids, host cells, and the like, refers to materials which are found in nature. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An antibody as such is a species of an antigen binding protein. Unless otherwise indicated, the term "antibody" includes, in addition to antibodies comprising two full-length heavy chains and two full-length light chains, derivatives, variants, fragments, and muteins thereof, examples of which are described below. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies.

The term "functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Fragments include, but are not limited to, immunologically functional fragments such as Fab, Fab', F(ab')2, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., a CD30L protein or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 92:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Different approaches may be taken as known by the skilled person. An alternative option includes having the reference antigen binding protein bound to the plate, optionally via a flexible matrix. Further variation maybe based on the order of addition ie, if the antigen is first mixed with plate bound reference antigen binding protein or test antigen binding protein. In all scenarios saturation of antigen by antigen binding protein is needed to avoid false non-competitive result.

Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97%, 98%, 99% or more.

Competition experiments may be made with different types of molecules which may have different sensitivity. If the antigen binding protein is an antibody the molecule will be bi-valent. If the antigen binding molecule is a Fab, it is monovalent and substantially smaller than a full length antibody resulting in less sterical hinderence. In competitions experiments this may For certain antigen binding protein the binding to hCD30L is inhibited by binding of a Fab of an antibody antigen binding protein as defined herein, such as any one of antibodies A, B, C, D, E and F.

The term "epitope" or "antigenic determinant" refers to a site on an antigen to which an antigen binding protein binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. Epitope determinants may include chemically active surface groupings of molecules such as amino acids, sugar side chains, phosphoryl or sulfonyl groups, and may have specific three dimensional structural characteristics, and/or specific charge characteristics. An epitope typically includes at least 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

The binding of an antigen binding protein may also be described by the region or regions of the antigen that the antigen binding protein interacts with. Such region(s) of interaction may be determined by various methods known in the art, such as by performing binding assays using variant antigen molecules or by HX-MS as exemplified herein (see Example 6), whereby the region(s) of interaction of the antigen with the antigen binding proteins is determined.

The HX-MS technology exploits, that hydrogen exchange (HX) of a protein can readily be followed by mass spectrometry (MS). By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides. HX-MS may be used to probe for sites involved in molecular interactions by identifying regions of reduced hydrogen exchange upon protein-protein complex formation including antibody-antigen interactions. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, i.e. protein and antibody or Fab fragment, and is performed in solution. Thus HX-MS provides the possibility for mimicking the in vivo conditions (for a review on the HX-MS technology, see e.g. Wales and Engen, Mass Spectrom. Rev. 25, 158 (2006)).

Certain antigen binding proteins as described herein interacts with or binds CD30L via a C-terminal region of human CD30L defined by AA201-234. It may be that the antigen binding protein binds a C-terminal region of human CD30L defined by AA 201-234, or a smaller region such as AA 205-230 or AA 211-226. As described above an epitope may be non-contiguous and so may the region of interaction. In one embodiment an antigen binding protein according to the invention binds to at least two regions of CD30L. Such further antigen binding proteins according to the invention may interact with a C-terminal region as defined above and a further region of human CD30L located in the N-terminal part of the extracellular domain, such as a region defined by AA70-100 of full length hCD30L. Such antigen binding proteins may bind to AA 75-95 or a shorter region, such as AA 80-90 or AA 82-88 in addition to the C-terminal region defined by AA 201-234, AA 205-230 or AA 211-226.

CD30L Antigen Binding Proteins

An "antigen binding protein" as used herein means a protein that specifically binds a specified target antigen; the antigen as provided herein is CD30L, particularly human CD30L. Antigen binding proteins include, for example, those that block or inhibit interaction of CD30L and CD30. Such "blocking" antigen binding proteins may be developed towards CD30L, or a fragment, variant or derivative thereof, and screened in conventional assays for the ability to interfere with interaction of CD30L and CD30. Examples of suitable assays are assays that test the antigen binding proteins ability to inhibit interaction of CD30L and CD30 are described herein. Antigen binding proteins also include those that inhibit CD30L or activate CD30L. Such inhibition or neutralization disrupts a biological response in the presence of the antigen binding protein compared to the response in the absence of the antigen binding protein and can be determined using assays known in the art and described herein. Antigen binding proteins provided herein, for example, induce IL-8 production from CD30$^+$ cells. Antigen binding proteins as disclosed herein also do not bind other TNF superfamily members, particularly 4-1BBL, OX-40L, TNFα, TNFβ, RANKL, Trail, CD40L or CD27L.

Different CD30L antigen binding proteins may bind to different domains or epitopes of CD30L or act by different mechanisms of action. A CD30L antigen binding protein need not completely inhibit a CD30L induced activity to find use as described herein; rather, antigen binding proteins that reduce a particular activity of CD30L are contemplated for use as well. Antigen binding proteins also include those that cross-compete for binding with human CD30L; bind to the same epitope of human CD30L; bind to human CD30L with substantially the same Kd; bind to CD30L with substantially the same off rate; as any of the reference antigen binding proteins described herein. Various methods for measuring such characteristics are known in the art and described herein.

Also provided are CD30L antigen binding proteins that deplete CD30L$^+$ cells. With such depleting CD30L antigen binding proteins, the binding of the antigen binding protein to a cell comprising its antigen target results in an inhibition of antigen or cellular function or results in death of the cell. In one embodiment, a depleting antibody of the invention binds CD30L and may or may not block the binding of a CD30L ligand to CD30. Thus, depleting antigen binding proteins specifically include blocking and non-blocking antigen binding proteins. In one aspect, CD30L antigen binding proteins that deplete CD30L$^+$ cells may induce apoptosis or programmed cell death, as determined by apoptosis assays known in the art. Such CD30L antigen binding proteins could have an immune modulatory effect by 1) eliminating cells that interact with CD30L$^+$ cells to induce an immune response and/or 2) eliminating cells in which CD30L is a cell surface marker of a cell type that participates in a certain immune response, but that does not necessarily need to interact with a CD30$^+$ cell to do so. In this case, CD30L would be a marker of cell type associated with a particular disease and the CD30/CD30L interaction may not be involved in the pathogenesis of the disease itself. Another embodiment includes depleting antigen binding proteins that comprise conjugated toxin or cytotoxic agent, wherein the toxin or cytotoxic agent induces depletion of a cell binding the antigen binding protein conjugate.

An antigen binding protein may comprise a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., Proteins: Structure, Function, and Bioinformatics, (2003) Volume 53, Issue 1:121-129; Roque et al., Biotechnol. Prog., 2004, 20:639-654. In addition, peptide antibody mimetics ("PAMs") can be used, as well as scaffolds based on antibody mimetics utilizing fibronection components as a scaffold.

Certain antigen binding proteins described herein are antibodies or are derived from antibodies. Such antigen binding proteins include, but are not limited to, monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, and fragments thereof, respectively. In some instances, the antigen binding protein is an immunological fragment of an antibody (e.g., a Fab, a Fab', a F(ab')2, or a scFv). The various structures are further described and defined herein.

Certain antigen binding proteins that are provided may comprise one or more CDRs as described herein (e.g., 1, 2, 3, 4, 5, 6 or more CDRs). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

Certain of the antigen binding proteins as provided herein specifically bind to human CD30L. "Specifically bind" as used herein means that the equilibrium dissociation constant ($K_D$) is <$10^{-8}$ to <$10^{-10}$ M, alternatively <$10^{-9}$ to <$10^{-10}$ M, more particularly <$10^{-11}$ M to <$10^{-12}$M. In one embodiment the antigen binding proteins bind with a high affinity expressed by the equilibrium dissociation constant ($K_D$) being $10^{-8}$, or such as $5.0 \times 10^{-9}$ or such as $10^{-9}$ or even $5.0 \times 10^{-10}$. The equilibrium dissociation constant may be determined as known in the art. In such embodiments $K_D$ is typically determined by immobilizing a species at low density (this species can be multivalent) and injecting a titration series of a monovalent species (association phase), and then allowing for a dissociation phase where the complexes fall apart. The rate constants corresponding to the association and the dissociation of a monovalent complex are referred to as the association rate constant $k_a$ and dissociation rate constant $k_d$, respectively. The resulting data are then fit to a 1:1 binding model that fits 3 parameters: association rate constant $k_a$, dissociation rate constant $k_d$, and Rmax, which is related to surface density & stoichiometry. The ratio of $k_d/k_a$ is equal to the equilibrium dissociation constant $K_D$.

$K_D$ may also be determined using FACS analysis as described in Example 4 herein, where antibodies are bound to CD30L express on a Ramos cells.

One embodiment relates to an isolated antigen binding protein as described herein, wherein said antigen binding protein has an affinity (or $K_D$) to human CD30L of at least 75 pM, such as 50 pM, such as 40 pM. In further embodiments the dissociation constant ($K_D$) of the antigen binding protein to human CD30L is at most 35 pM, such as at most 25 pM, such as at most 20 pM, such as at most 15 pM. The affinity (or $K_D$) may in such embodiment be determined by FACS as described in Example 4 herein.

Another aspect provides an antigen binding protein having a half-life of at least one day in vitro or in vivo (e.g., when administered to a human subject). In one embodiment, the antigen binding protein has a half-life of at least three days. In another embodiment, the antibody or portion thereof has a half-life of four days or longer. In another embodiment, the antibody or portion thereof has a half-life of eight days or longer. In another embodiment, the antibody or antigen binding portion thereof is derivatized or modified such that it has a longer half-life as compared to the underivatized or unmodified antibody. In another embodiment, the antigen binding protein contains point mutations to increase serum half life, such as described in WIPO Publication No. WO 00/09560.

In embodiments where the antigen binding protein is used for therapeutic applications, an antigen binding protein can reduce, inhibit, interfere with or modulate one or more biological activities of CD30L, such as induction of IL-8 production from CD30+ cells.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable region that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable region and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain constant region (CH) typically comprises one or more domains that may be responsible for effector function. The number of heavy chain constant region domains will depend on the isotype. IgG heavy chains, for example, each contains three CH region domains known as CH1, CH2 and CH3. The antigen binding proteins that are provided can have any of these isotypes and subtypes, for example, the CD30L antigen binding protein is of the IgG1, IgG2, or IgG4 subtype. If an IgG4 is desired, it may also be desired to introduce a point mutation (CPSCP→CPPCP) in the hinge region as described in Bloom et al., 1997, Protein Science 6:407) to alleviate a tendency to form intra-H chain disulfide bonds that can lead to heterogeneity in the IgG4 antibodies. Antibodies provided herein that are of one type can be changed to a different type using subclass switching methods. See, e.g., Lantto et al., 2002, Methods Mol. Biol. 178:303-316.

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press. The variable regions of each light/heavy chain pair typically form the antigen binding site.

Variable Regions

Various heavy chain and light chain variable regions (or domains) provided herein are depicted in TABLES 1 and 2. Each of these variable regions may be attached, for example, to heavy and light chain constant regions described above. Further, each of the so generated heavy and light chain sequences may be combined to form a complete antigen binding protein structure.

TABLE 1

Exemplary Variant Light Chain Region Sequences

| | |
|---|---|
| VL1 SEQ ID NO: 36 | QSALTQPASVSGSPGQSITISCTGTSSDVGVYDYVS WYQQHPGKAPKLMIYEVSNRPSGVSNRFSGSKSGNTAS LTISGLQTEDEADYYCSSYTSRSTWVFGGGTKLTVL |

TABLE 1-continued

Exemplary Variant Light Chain Region Sequences

VL2
SEQ ID
NO: 38
QSALTQPASVSGSPGQSITISCTGTSSDVGLYNYVSW
YQQHPDKAPKLMIFEVNNRPSGVSNRFSGSNSGNTASL
TISGLQAEDEADYYCSSYTSSSTWVFGGGTKLTVL

VL3
SEQ ID
NO: 40
QSALTQPASVSGSPGQSITISCTGTSSDIGLYDYVS
WYQQHPDRAPKLIIFEVNNRPSGVSYRFSGSNSGNTA
SLTISGLQAEDEADYYCSSYTSSSTWVFGGGTKLTVL

VL4
SEQ ID
NO: 42
QSALTQPASVSGSPGQSITISCTGTSSDIGLYNYVS
WYQQHPDKAPKLIIYEVINRPSGVSNRFSGSESGNTA
SLTISGLQAEDEANYYCSSYTSSSTWVFGGGTKLTVL

TABLE 1-continued

Exemplary Variant Light Chain Region Sequences

VL5
SEQ ID
NO: 44
QSALTQPASVSGSPGQSITISCTGSSSDIGTYNYVSWY
QQYPGKAPELMIYEVNNRPSGVSDRFSGSTSGNTASL
TISGLQANDEADYYCSSYSSSSTWVFGGGTKLTVL

VL6
SEQ ID
NO: 46
QSALTQPASVSGSPGQSITISCTGTSSDVGLYNYVS
WYQQQPGKAPKLMIYEVSKRPSGVSNRFSGSTSGNTA
SLTISGLQADDEADYSCSSYTSSSTWVFGGGTKLTVL

Complementarity determining regions (CDR) are in bold italics, framework regions (FR) are in plain type. The order of the elements is: FR1, CDR1, FR2, CDR2, FR3, CDR3 and FR4.

TABLE 2

Exemplary Variant Heavy Chain Region Sequences

VH1
SEQ ID
NO: 48
QVQLQESGPGLVKPSETLSLICTVSGGSISSYIWSWIRQPAGKGLEWIG**RIYASGNTNY
NPSLKSRVTISVDTSKNQFSLKLSSMTAADTAVYYCARDYRVAGTYYYYYGLDV**WGQG
TTVTVSS

VH2
SEQ ID
NO: 50
QVQLQESGPGLVKPSETLSLTCTVSGGSISSYIWSWIRQPAGKGLEWIG**RIYASGNTNY
NPSLKSRVTMSVDTSKNQFSLKLSSMTAADTAVYYCARDYRVAGTYYYYYGLDV**WGQ
GTTVTVSS

VH3
SEQ ID
NO: 52
QVQLQESGPGLVKPSETLSLTCTVSGGSISSYIWSWIRQPAGKGLEWIG**RIYASGNTNY
NPSLKSRVTMSVDTSKNQFSLKLSSVTAADTAVYYCARDYRVAGTYYYYYGLDV**WGQG
GTTVTVSS

VH4
SEQ ID
NO: 54
QVQLQESGPGLVKPSETLSLTCTVSGGSISSYIWSWIRQPAGKGLEWIG**RIYASGNTNY
NPSLKSRVTMSVDTSKNQFSLKLSSMTAADTAVYYCARDYRVAGTYYYYYGLDV**WGQG
GTTVTVSS

VH5
SEQ ID
NO: 56
QVQLQESGPGLVKPSETLSLTCTVSGGSISSSYIWSWIRQPAGKGLEWIG**RIYASGNTNY
NPSLKSRVTISVDTSKNQFSLKLSSVTAADTAVYYCARDYRVAGTYYYYYGLDV**WGQG
TTVTVSS

VH6
SEQ ID
NO: 58
QVQLQESGPGLVKPSETLSLTCTVSGGSISSYIWSWIRQPAGKGLEWIG**RIYASGNTNY
NPSLKSRVTISVDTSKNQFSLKLSSVTAADTAVYYCARDYRVAGTYYYYYGLDV**WGQG
TTVTVSS

VH7
SEQ ID
NO: 60
QVQLQESGPGLVKPSETLSLICTVSGGSISSYIWSWIRQPAGKGLEWIG**RIYASGNTNY
NPSLKSRVTISVDTSKNQFSLKLSSMTAADTAVYYCARDYRVAGTYYYYYGLDV**WGQG
TTVTVSS

VH8
SEQ ID
NO: 62
QVQLQESGPGLVKPSETLSLICTVSGGSISSYIWSWIRQPAGKGLEWIG**RIYASGQTNY
NPSLKSRVTMSVDTSKNQFSLKLSSVTAADTAVYYCARDYRVAGTYYYYYGLDV**WGQG
TTVTVSS

VH9
SEQ ID
NO: 64
QVQLQESGPGLVKPSETLSLTCTVSGGSISSYYWTWIRQPAGKGLEWIG**RIYTSGITNYN
PSLKSRVTMSVDTSKNQFSLKLSSVTAADTAVYYCARERVVGASRYYYYGVDV**WGQG
TTVTVSS

VH10
SEQ ID
NO: 66
QVQLQESGPGLVKPSETLSLTCTVSGGSISSYYWTWIRQPAGKGLEWIG**RIYTSGITNYN
PSLKSRVTMSVDTSKNQFSLKLSSVTAADTAVYYCARERVVGASRYYYYGVDV**GQG
TTVTVSS

VH11
SEQ ID
NO: 68
QVQLQESGPGLVKPSETLSLTCTVSGGSISSYSWSWIRQPAGKGLEWIG**RTSTSGRNN
YNPSLKSRVTMSVDTSKNQFSLKLNSVTAADTAVYYCARDFTIAARRYYYYGMD**WGQ
GTTVTVSS

VH12
SEQ ID
NO: 70
QVQLQESGPRLVKPSETLSLICTVSGGSITNNYWSWIRQPAGKGLEWIG**RVYSSGLTN
YKPSLKSRVTMSVDTSKNQFSLRLNSVTAADTAVYYCARERATVTTRYHYDGMD**WG
QGTSVTVSS

VH13
SEQ ID
NO: 72
QVQLQESGPGLVKPSETLSLTCTVSGGSISSYYWSWIRQPAGKGLEWIG**RIFASGSTNY
NPSLRSRVTMSRDTSKNQFSLKLSSVTAADTAVYYCAKERVGVQDYYHYSGMDV**WGQ
GTTVTVSS

Complementarity determining regions (CDR) are in bold italics, framework regions (FR) are in plain type. The order of the elements is: FR1, CDR1, FR2, CDR2, FR3, CDR3 and FR4. Provided are antigen binding proteins that contain at least one heavy chain variable region (VH) selected from the group consisting of VH1, VH2, VH3, VH4, VH5, VH6, VH7, VH8, VH9, VH11, VH12 and VH13 and/or at least one light chain variable region (VL) selected from the group consisting of VL1, VL2, VL3, VL4, VL5, VL6 as shown in TABLES 1 and 2.

Provided are antigen binding proteins that contain at least one heavy chain variable region (VH) selected from the group consisting of VH1, VH2, VH3, VH4, VH5, VH6, VH7, VH8, VH9, VH10, VH11, VH12 and VH13 and/or at least one light chain variable region (VL) selected from the group consisting of VL1, VL2, VL3, VL4, VL5, VL6 as shown in TABLES 1 and 2.

Each of the heavy chain variable regions listed in TABLE 2 may be combined with any of the light chain variable regions shown in TABLE 1 to form an antigen binding protein. In some instances, the antigen binding protein includes at least one heavy chain variable region and/or one light chain variable region from those listed in TABLES 1 and 2. In some instances, the antigen binding protein includes at least two different heavy chain variable regions and/or light chain variable regions from those listed in TABLES 1 and 2. The various combinations of heavy chain variable regions may be combined with any of the various combinations of light chain variable regions.

In other instances, the antigen binding protein contains two identical light chain variable regions and/or two identical heavy chain variable regions. As an example, the antigen binding protein may be an antibody or immunologically functional fragment that comprises two light chain variable regions and two heavy chain variable regions in combinations of pairs of light chain variable regions and pairs of heavy chain variable regions as listed in TABLES 1 and 2. Examples of such antigen binding proteins comprising two identical heavy chain and light chain variable regions include: Antibody A VH2/VL1; Antibody A1 VH1/VL1; Antibody A2 VH3/VL1; Antibody A3 VH4/VL1; Antibody A4 VH5/VL1; Antibody A5 VH6/VL1; Antibody A6 VH7/VL1; Antibody A7 VH8/VL1; Antibody B VH9/VL2; Antibody C VH10/VL3; Antibody D VH11/VL4; Antibody E VH12/VL5 and Antibody F VH13/VL6.

Some antigen binding proteins that are provided comprise a heavy chain variable region and/or a light chain variable region comprising a sequence of amino acids that differs from the sequence of a heavy chain variable region and/or a light chain variable region selected from TABLES 1 and 2 at only 1, 2, 3, 4, 5, 6, 7, 8, 9, 10, 11, 12, 13, 14, 15, 20, 25, 30, 31 or more amino acid residues, wherein each such sequence difference is independently either a deletion, insertion or substitution of one amino acid. The light and heavy chain variable regions, in some antigen binding proteins, comprise sequences of amino acids that have at least 70%, 75%, 80%, 85% 86%, 87%, 88%, 89%, 90%, 91%, 92%, 93%, 94%, 95%, 96%, 97%, 98% or 99% sequence identity to the amino acid sequences provided in TABLES 1 and 2. Still other antigen binding proteins, e.g., antibodies or immunologically functional fragments, also include variant heavy chain region forms and/or variant light chain region forms as described herein.

The term "identity" refers to a relationship between the sequences of two or more polypeptide molecules or two or more polynucleotides, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, *Sequence Analysis in Molecular Biology*, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following: Algorithm: Needleman et al., 1970, *J. Mol. Biol.* 48:443-453; Comparison matrix: BLOSUM 62 from Henikoff et al., 1992, supra; Gap Penalty: 12 (but with no penalty for end gaps), Gap Length Penalty: 4, Threshold of Similarity: 0. Certain alignment schemes for aligning two amino acid sequences may result in matching of only a short region of the two sequences and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

Complementarity Determining Regions

Complementarity determining regions or "CDRs" are embedded within a framework in the heavy and light chain variable regions where they constitute the regions responsible for antigen binding and recognition. Variable domains of immunoglobulin chains of the same species, for example, generally exhibit a similar overall structure; comprising relatively conserved framework regions (FR) joined by hypervariable CDR regions. An antigen binding protein can have 1, 2, 3, 4, 5, 6 or more CDRs. The variable regions discussed above, for example, typically comprise three CDRs. The CDRs from heavy chain variable regions and light chain variable regions are typically aligned by the framework regions to form a structure that binds specifically on a target antigen (e.g., CD30L). From N-terminal to C-terminal, naturally-occurring light and heavy chain variable regions both typically conform to the following order of these elements: FR1, CDR1, FR2, CDR2, FR3, CDR3 and FR4. The CDR and FR regions of exemplary light chain variable domains and heavy chain variable domains are highlighted in TABLES 1 and 2. It is recognized that the boundaries of the CDR and FR regions can vary from those highlighted. Numbering systems have been devised for assigning numbers to amino acids that occupy positions in each of these domains. Complementarity determining regions and framework regions of a given antigen binding protein may be identified using these systems. Numbering systems are defined in Kabat et al., Sequences of Proteins of Immunological Interest, 5$^{th}$ Ed., US Dept. of Health and Human Services, PHS, NIH, NIH Publication No. 91-3242, 1991, or Chothia & Lesk, 1987, *J. Mol. Biol.* 196:901-917; Chothia et al., 1989, *Nature* 342:878-883. Other numbering systems for the amino acids in immunoglobulin chains include IMGT® (the international ImMunoGeneTics information system; Lefranc et al, *Dev. Comp. Immunol.* 2005, 29:185-203); and AHo (Honegger and Pluckthun, *J. Mol. Biol.* 2001, 309(3):657-670). The CDRs provided herein may not only be used to define the antigen binding domain of a traditional antibody structure, but may be embedded in a variety of other polypeptide structures, as described herein.

The antigen binding proteins disclosed herein are polypeptides into which one or more CDRs may be grafted, inserted, embedded and/or joined. An antigen binding protein can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific embodiments generally utilize combinations of CDRs that are non-repetitive, e.g., antigen binding proteins are generally not made with two CDRH2 regions in one variable heavy chain region, etc. Antigen binding proteins may comprise one or more amino acid sequences that are identical to or that differ from to the amino acid sequences of one or more of the CDRs presented in TABLE 3 at only 1, 2, 3, 4, 5, 6, 7, 8, 9, 10, 11, 12, 13, 14, 15, 16 or more amino acid residues, wherein each such sequence difference is independently either a deletion, insertion or substitution of one amino acid. The CDRs in some antigen binding proteins comprise sequences of amino acids that have at least 80%, 85%, 90%, 91%, 92, 93%, 94%, 95%, 96%, 97%, 98%, or 99% sequence identity to CDRs sequence listed in TABLE 3. In some antigen binding proteins, the CDRs are embedded into a "framework" region, which orients the CDR(s) such that the proper antigen binding properties of the CDR(s) is achieved.

TABLE 3

| Exemplary Variant Heavy Chain Region Sequences | |
| --- | --- |
| SEQ ID NO: 1 | TGTSSDVGVYDYVS |
| SEQ ID NO: 2 | TGTSSDVGLYNYVS |
| SEQ ID NO: 3 | TGTSSDIGLYDYVS |
| SEQ ID NO: 4 | TGTSSDIGLYNYVS |
| SEQ ID NO: 5 | TGSSSDIGTYNYVS |
| SEQ ID NO: 6 | TGTSSDVGLYNYVS |
| SEQ ID NO: 7 | EVSNRPS |
| SEQ ID NO: 8 | EVNNRPS |
| SEQ ID NO: 9 | EVINRPS |

TABLE 3-continued

| Exemplary Variant Heavy Chain Region Sequences | |
| --- | --- |
| SEQ ID NO: 10 | EVSKRPS |
| SEQ ID NO: 11 | SSYTSRSTWV |
| SEQ ID NO: 12 | SSYTSRSTWV |
| SEQ ID NO: 13 | SSYSSSSTVVV |
| SEQ ID NO: 14 | SYIWS |
| SEQ ID NO: 15 | SYYWT |
| SEQ ID NO: 16 | SYSWS |
| SEQ ID NO: 17 | NNYWS |
| SEQ ID NO: 18 | SYYWS |
| SEQ ID NO: 19 | RIYASGNTNYNPSLKS |
| SEQ ID NO: 20 | RIYASGQTNYNPSLKS |
| SEQ ID NO: 21 | RIYTSGITNYNPSLKS |
| SEQ ID NO: 22 | RTSTSGRNNYNPSLKS |
| SEQ ID NO: 23 | RVYSSGLTNYKPSLKS |
| SEQ ID NO: 24 | RIFASGSTNYNPSLRS |
| SEQ ID NO: 25 | DYRVAGTYYYYGLDV |
| SEQ ID NO: 26 | ERVVGASRYYYYGVDV |
| SEQ ID NO: 27 | DFTIAARRYYYYGMDV |
| SEQ ID NO: 28 | ERATVTTRYHYDGMDV |
| SEQ ID NO: 29 | ERVGVQDYYHYSGMDV |

Provided herein are CDR1 regions comprising amino acid residues 23-36 of SEQ ID NOs: 36, 38, 40, 42 and 44; amino acid residues 25-36 of SEQ ID NO:46 and amino acid residues 31-35 of SEQ ID NOs: 48, 50, 52, 54, 56, 58, 60, 62, 64, 66, 68, 70 and 72. CDR2 regions are provided comprising amino acid residues 52-58 of SEQ ID NOs: 36, 38, 40, 42, 44 and 46 and amino acid residues 50-65 of SEQ ID NOs: 48, 50, 52, 54, 56, 58, 60, 62, 64, 66, 68, 70 and 72. CDR3 regions comprising amino acid residues 91-100 of SEQ ID NOs: 36, 38, 40, 42, 44 and 46 and amino acid residues 98-113 of SEQ ID NOs: 48, 50, 52, 54, 56, 58, 60, 62, 64, 66, 68, 70 and 72.

The CDRs disclosed herein include consensus sequences derived from groups of related sequences. The CDRL1 consensus sequence consists of TGX1SSDX2GX3YX4YVS (SEQ ID NO:30) where X1 is threonine or serine, X2 is valine or isoleucine, X3 is valine, threonine or leucine, and X4 is aspartic acid or asparagine.

The CDRL2 consensus sequence consists of EVX1X2RPS (SEQ ID NO:31) wherein X1 is serine, asparagine or isoleucine and X2 is asparagine or lysine.

The CDRL3 consensus sequence include SSYX1SX2STWV (SEQ ID NO:32) wherein X1 is threonine or serine and X2 is arginine or serine.

The CDRH1 consensus sequence consists of X1X2X3WX4 (SEQ ID NO:33) wherein X1 is serine or asparagine, X2 is tyrosine or asparagine, X3 is isoleucine, tyrosine or serine and X4 is threonine or serine. In a different embodiment the CDRH1 consensus sequence consists of SYX3WX5 (SEQ ID NO:75) wherein X3 is I, S or Y and X5 is T or S.

The CDRH2 consensus sequence consists of RX1X2X3SGX4X5NYX6PSLX7S (SEQ ID NO:34) wherein X1 is isoleucine, valine or threonine, X2 is tyrosine, phenylanaline, or serine, X3 is threonine, serine or alanine, X4 is isoleucine, leucine, asparagine, serine, arginine or glutamine, X5 is threonine or asparagine, X6 is asparagine or lysine and X7 is lysine or arginine.

The CDRH3 consensus sequence consists of X1X2X3X4X5X6X7X8YX9YX10GX11DV (SEQ ID NO:35) wherein X1 is glutamic acid or aspartic acid, X2 is arginine, tyrosine or phenylaline, X3 is valine, alanine, arginine or threonine, X4 is valine, threonine, glycine or isoleucine, X5 is valine, alanine or glycine, X6 is alanine, theorine, glycine, or glutamine, X7 is threonine, aspartic acid, argine or serine, X8 is arginine or tyrosine, X9 is tyrosine or histidine, X10 is tyrosine, aspartic acid or serine and X11 is methionine, leucine or valine.

Monoclonal Antibodies

The antigen binding proteins that are provided include monoclonal antibodies that bind to CD30L. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a CD30L immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a CD30L polypeptide. Such hybridoma cell lines, and anti-CD30L monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to reduce, inhibit, interfere with or modulate CD30L interaction with CD30.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855. CDR grafting is described, for example, in U.S. Pat. Nos. 6,180,370, 5,693,762, 5,693,761, 5,585,089, and 5,530,101.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and U.S. Pat. No. 5,693,762; Jones et al., 1986, *Nature* 321:522-525; Riechmann et al., 1988, *Nature* 332:323-27; Verhoeyen et al., 1988, *Science* 239:1534-1536), In certain embodiments, constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WIPO patent publications WO96/33735 and WO94/02602. Additional methods relating to transgenic mice for making human antibodies are described in U.S. Pat. Nos. 5,545,807;

6,713,610; 6,673,986; 6,162,963; 5,545,807; 6,300,129; 6,255,458; 5,877,397; 5,874,299 and 5,545,806; in WIPO patent publications WO91/10741, WO90/04036, and in EP 546073B1 and EP 546073A1.

The transgenic mice described above contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, Nature 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, Intern. Rev. Immunol. 13: 65-93; Harding and Lonberg, 1995, Ann. N.Y Acad. Sci. 764:536-546). The preparation of such mice is described in detail in Taylor et al., 1992, Nucleic Acids Research 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg and Huszar, 1995, Intern. Rev. Immunol. 13:65-93; Harding and Lonberg, 1995, Ann. N.Y Acad. Sci. 764:536-546; Fishwild et al., 1996, Nature Biotechnology 14:845-85. See, further U.S. Pat. No. 5,545,806; U.S. Pat. No. 5,569,825; U.S. Pat. No. 5,625,126; U.S. Pat. No. 5,633,425; U.S. Pat. No. 5,789,650; U.S. Pat. No. 5,877,397; U.S. Pat. No. 5,661,016; U.S. Pat. No. 5,814,318; U.S. Pat. No. 5,874,299; and U.S. Pat. No. 5,770,429; as well as U.S. Pat. No. 5,545,807; WIPO Publication Nos. WO 93/1227; WO 92/22646; and WO 92/03918. Technologies utilized for producing human antibodies in these transgenic mice are disclosed also in WIPO Publication No. WO 98/24893, and Mendez et al., 1997, Nature Genetics 15:146-156. For example, the HCo7 and HCo12 transgenic mice strains can be used to generate anti-CD30L antibodies.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (such as disclosed in Hoogenboom et al., 1991, J. Mol. Biol. 227:381; Marks et al., 1991, J. Mol. Biol. 222:581; WIPO Publication No. WO 99/10494). Phage display techniques mimic immune selection through the display of antibody repertoires on the surface of filamentous bacteriophage, and subsequent selection of phage by their binding to an antigen of choice.

Bispecific or Bifunctional Antigen Binding Proteins

A "bispecific," "dual-specific" or "bifunctional" antigen binding protein or antibody is a hybrid antigen binding protein or antibody, respectively, having two different antigen binding sites, such as one or more CDRs or one or more variable regions as described above. In some instances they are an artificial hybrid antibody having two different heavy/light chain pairs and two different binding sites. Multispecific antigen binding protein or "multispecific antibody" is one that targets more than one antigen or epitope. Bispecific antigen binding proteins and antibodies are a species of multispecific antigen binding protein antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553.

Immunological Fragments

Antigen binding proteins also include immunological fragments of an antibody (e.g., a Fab, a Fab', a F(ab')$_2$, or a scFv). A "Fab fragment" is comprised one light chain (the light chain variable region ($V_L$) and its corresponding constant domain ($C_L$)) and one heavy chain (the heavy chain variable region ($V_H$) and first constant domain ($C_H1$)). The heavy chain of a Fab molecule cannot form a disulfide bond with another heavy chain molecule. A "Fab' fragment" contains one light chain and a portion of one heavy chain that also contains the region between the $C_H1$ and $C_H2$ domains, such that an interchain disulfide bond can be formed between the two heavy chains of two Fab' fragments to form an F(ab')$_2$ molecule. A "F(ab')$_2$ fragment" thus is composed of two Fab' fragments that are held together by a disulfide bond between the two heavy chains. A "Fv fragment" consists of the variable light chain region and variable heavy chain region of a single arm of an antibody. Single-chain antibodies "scFv" are Fv molecules in which the heavy and light chain variable regions have been connected by a flexible linker to form a single polypeptide chain, which forms an antigen binding region. Single chain antibodies are discussed in detail in WIPO Publication No. WO 88/01649, U.S. Pat. No. 4,946,778 and U.S. Pat. No. 5,260,203; Bird, 1988, Science 242:423; Huston et al., 1988, Proc. Natl. Acad. Sci. U.S.A. 85:5879; Ward et al., 1989, Nature 334: 544, de Graaf et al., 2002, Methods Mol Biol. 178:379-387; Kortt et al., 1997, Prot. Eng. 10:423; Kortt et al., 2001, Biomol. Eng. 18:95-108 and Kriangkum et al., 2001, Biomol. Eng. 18:31-40. A "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

Also included are domain antibodies, immunologically functional immunoglobulin fragments containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens. Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., Proc. Natl. Acad. Sci. USA 90:6444-48, 1993 and Poljak et al., Structure 2:1121-23, 1994). Similarly, tribodies and tetrabodies are antibodies comprising three and four polypeptide chains, respectively, and forming three and four antigen binding sites, respectively, which can be the same or different. Maxibodies comprise bivalent scFvs covalently attached to the Fc region of IgG$_1$, (see, e.g., Fredericks et al, 2004, Protein Engineering, Design & Selection, 17:95-106; Powers et al., 2001, Journal of Immunological Methods, 251:123-135; Shu et al., 1993, Proc. Natl. Acad. Sci. USA 90:7995-7999; Hayden et al., 1994, Therapeutic Immunology 1:3-15).

Various Other Forms

Also provided are variant forms of the antigen binding proteins disclosed above, some of the antigen binding proteins having, for example, one or more conservative amino acid substitutions in one or more of the heavy or light chains, variable regions or CDRs listed in TABLES 1 and 2.

Naturally-occurring amino acids may be divided into classes based on common side chain properties: hydrophobic (norleucine, Met, Ala, Val, Leu, Ile); neutral hydrophilic (Cys, Ser, Thr, Asn, Gln); acidic (Asp, Glu); basic (His, Lys, Arg); residues that influence chain orientation (Gly, Pro); and aromatic (Trp, Tyr, Phe).

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. Such substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within +1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within +1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in TABLE 4.

TABLE 4

| Conservative Amino Acid Substitutions | |
|---|---|
| Residue | Sub |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |
| Thr | Ser |

Residue = Original Residue
Sub = Exemplary Substitution

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for CD30L activity, (see Example section below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides, such as maintaining the structure of the molecular backbone in the area of the substitution, for example, as a sheet or helical conformation; maintaining or altering the charge or hydrophobicity of the molecule at the target site, or maintaining or altering the bulkiness of a side chain.

For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, Nature 354:105.

Additional variants include cysteine variants wherein one or more cysteine residues in the parent or native amino acid sequence are deleted from or substituted with another amino acid (e.g., serine). Cysteine variants are useful, inter alia when antibodies (for example) must be refolded into a biologically active conformation. Cysteine variants may have fewer cysteine residues than the native protein, and typically have an even number to minimize interactions resulting from unpaired cysteines.

The heavy and light chain variable region and CDRs that are disclosed can be used to prepare antigen binding proteins that contain an antigen binding region that can specifically bind to a CD30L polypeptide. "Antigen binding region" means a protein, or a portion of a protein, that specifically binds a specified antigen, such as the region that contains the amino acid residues that interact with an antigen and confer on the antigen binding protein its specificity and affinity for the target antigen. An antigen binding region may include one or more CDRs and certain antigen binding regions also include one or more "framework" regions. For example, one or more of the CDRs listed in TABLE 3 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., a CD30L polypeptide).

Other antigen binding proteins include mimetics (e.g., "peptide mimetics" or "peptidomimetics") based upon the variable regions and CDRs that are described herein. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antigen binding protein displaying a desired biological activity, such as the ability to inhibit or block the interaction of CD30 and CD30L, but peptidomimetics have one or more peptide linkages optionally replaced by a linkage selected from, for example: $—CH_2NH—$, $—CH_2S—$, $—CH_2—CH_2—$, $—CH=CH-$(cis and trans), $—COCH_2—$, $—CH(OH)CH_2—$, and $—CH_2SO—$, by methods well known in the art.

Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antigen binding protein or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or Streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of CD30L antigen binding proteins with other proteins or polypeptides, such as by expression of recombinant fusion proteins comprising heterologous polypeptides fused to the N-terminus or C-terminus of a CD30L antigen binding protein. For example, the conjugated peptide may be a heterologous signal (or leader) polypeptide, e.g., the yeast alpha-factor leader, or a peptide such as an epitope tag. CD30L antigen binding protein-containing fusion proteins can comprise peptides added to facilitate purification or identification of the CD30L antigen binding protein (e.g., poly-His). A CD30L antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more CD30L antigen binding proteins may be employed as CD30L antagonists. Oligomers may be in the form of covalently-linked or non-covalently-linked dimers, trimers, or higher oligomers. Oligomers comprising two or more CD30L antigen binding proteins are contemplated for use, with one example being a homodimer. Other oligomers include heterodimers, homotrimers, heterotrimers, homotetramers, heterotetramers, etc. Oligomers comprising multiple CD30L binding proteins joined via covalent or non-covalent interactions between peptide moieties fused to the CD30L antigen binding proteins, are also included. Such peptides may be peptide linkers (spacers), or peptides that have the property of promoting oligomerization. Among the suitable peptide linkers are those described in U.S. Pat. Nos. 4,751,180 and 4,935,233. Leucine zippers and certain polypeptides derived from antibodies are among the peptides that can promote oligomerization of CD30L antigen binding proteins attached thereto. Examples of leucine zipper domains suitable for producing soluble oligomeric proteins are described in WIPO Publication No. WO 94/10308; Hoppe et al., 1994, *FEBS Letters* 344:191; and Fanslow et al., 1994, *Semin. Immunol.* 6:267-278. In one approach, recombinant fusion proteins comprising a CD30L antigen binding protein fragment or derivative fused to a leucine zipper peptide are expressed in suitable host cells, and the soluble oligomeric CD30L antigen binding protein fragments or derivatives that form are recovered from the culture supernatant.

Such oligomers may comprise from two to four CD30L antigen binding proteins. The CD30L antigen binding protein moieties of the oligomer may be in any of the forms described above, e.g., variants or fragments. Preferably, the oligomers comprise CD30L antigen binding proteins that have CD30L binding activity. Oligomers may be prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

Also included are dimers comprising two fusion proteins created by fusing a CD30L antigen binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer. Such Fc polypeptides include native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns. One suitable Fc polypeptide, described in WIPO Publication No. WO 93/10151 and U.S. Pat. Nos. 5,426,048 and 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in WIPO Publication No. WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Glycosylation The antigen binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. Themethods are described in PCT Publication No. WO 87/05330, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antigen binding protein variants comprise a greater or a lesser number of N-linked glycosylation sites than the parent polypeptide. Substitutions that eliminate or alter this sequence will prevent addition of an N-linked carbohydrate chain present in the parent polypeptide. For example, the glycosylation can be reduced by the deletion of an Asn or by substituting the Asn with a different amino acid. Antibodies typically have a N-linked glycosylation site in the Fc region.

Labels And Effector Groups

Antigen binding proteins may comprise one or more labels. The term "label" or "labeling group" refers to any detectable label. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, 3-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art. Examples of suitable labeling groups include, but are not limited to, the following: radioisotopes or radionuclides (e.g., $^{3}H$, $^{14}$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^{3}H$, $^{14}O$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

Polynucleotides Encoding CD30L Antigen Binding Proteins

Polynucleotides that encode the antigen binding proteins described herein, or portions thereof, are also provided, including polynucleotides encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The polynucleotides can be any length. They can be, for example, 5, 10, 15, 20, 25, 30, 35, 40, 45, 50, 75, 85, 95, 100, 125, 150, 175, 200, 250, 300, 350, 400, 450, 500, 750, 1,000, 1,500, 3,000, 5,000 or more nucleic acids in length, including all values in between, and/or can comprise one or more additional sequences, for example, regulatory sequences, and/or be part of a larger polynucleotide, for example, a vector. The polynucleotides can be single-stranded or double-stranded and can comprise RNA and/or DNA nucleic acids and artificial variants thereof (e.g., peptide nucleic acids).

Polynucleotides encoding certain antigen binding proteins, or portions thereof (e.g., full length antibody, heavy or light chain, variable domain, or a CDRH1, CDRH2, CDRH3, CDRL1, CDRL2, or CDRL3) may be isolated from B-cells of mice that have been immunized with CD30L or an immunogenic fragment thereof. The polynucleotide may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding protein molecules. Phage display is also used to derive antigen binding proteins having different properties (i.e., varying affinities for the antigen to which they bind) via chain shuffling, see Marks et al., 1992, *BioTechnology* 10:779.

Due to the degeneracy of the genetic code, each of the polypeptide sequences depicted herein are also encoded by a large number of other polynucleotide sequences besides those provided. For example, heavy chain variable domains provided herein in may be encoded by polynucleotide sequences SEQ ID NOs: 49, 51, 53, 55, 57, 59, 61, 63, 65, 67, 69, 71 and 73. Light chain variable domains may be encoded by polynucleotide sequences SEQ ID NOs: 37, 39, 41, 43, 45, and 47. One of ordinary skill in the art will appreciate that the present application thus provides adequate written description and enablement for each degenerate nucleotide sequence encoding each antigen binding protein.

An aspect further provides polynucleotides that hybridize to other polynucleotide molecules under particular hybridization conditions. Methods for hybridizing nucleic acids, basic parameters affecting the choice of hybridization conditions and guidance for devising suitable conditions are well-known in the art. See, e.g., Sambrook, Fritsch, and Maniatis (2001, Molecular Cloning: A Laboratory Manual, Cold Spring Harbor Laboratory Press, Cold Spring Harbor, N.Y. and Current Protocols in Molecular Biology, 1995, Ausubel et al., eds., John Wiley & Sons, Inc. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that polynucleotides comprising nucleic acid sequences that are at least 65%, 70%, 75%, 80%, 85%, 90%, 91%, 92, 93%, 94%, 95%, 96%, 97%, 98% or 99% identical to each other, including all values in between, typically remain hybridized to each other.

Changes can be introduced by mutation into a polynucleotide, thereby leading to changes in the amino acid sequence of a polypeptide (e.g., an antigen binding protein or antigen binding protein derivative) that it encodes. Mutations can be introduced using any technique known in the art, such as site-directed mutagenesis and random mutagenesis. Mutant polypeptides can be expressed and selected for a desired property. Mutations can be introduced into a polynucleotide without significantly altering the biological activity of a polypeptide that it encodes. For example, substitutions at non-essential amino acid residues. Alternatively, one or more mutations can be introduced into a polynucleotide that selectively change the biological activity of a polypeptide that it encodes. For example, the mutation can quantitatively or qualitatively change the biological activity, such as increasing, reducing or eliminating the activity and changing the antigen specificity of an antigen binding protein.

Another aspect provides polynucleotides that are suitable for use as primers or hybridization probes for the detection of nucleic acid sequences. A polynucleotide can comprise only a portion of a nucleic acid sequence encoding a full-length polypeptide, for example, a fragment that can be used as a probe or primer or a fragment encoding an active portion (e.g., a CD30L binding portion) of a polypeptide. Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Methods of Expressing Antigen Binding Proteins

The antigen binding proteins provided herein may be prepared by any of a number of conventional techniques. For example, CD30L antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Expression systems and constructs in the form of plasmids, expression vectors, transcription or expression cassettes that comprise at least one polynucleotide as described above are also provided herein, as well host cells comprising such expression systems or constructs. As used herein, "vector" means any molecule or entity (e.g., nucleic acid, plasmid, bacteriophage or virus) suitable for use to transfer protein coding information into a host cell. Examples of vectors include, but are not limited to, plasmids, viral vectors, non-episomal mammalian vectors and expression vectors, for example, recombinant expression vectors. Expression vectors, such as recombinant expression vectors, are useful for transformation of a host cell and contain nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto. "Operably linked" means that the components to which the term is applied are in a relationship that allows them to carry out their inherent functions. For example, a control sequence, e.g., a promoter, in a vector that is "operably linked" to a protein coding sequence are arranged such that normal activity of the control sequence leads to transcription of the protein coding sequence resulting in recombinant expression of the encoded protein.

Another aspect provides host cells into which an expression vector, such as a recombinant expression vector, has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced polynucleotide can be identified by drug selection (e.g., cells that have incorporated the selectable marker gene will survive, while the other cells die), among other methods.

Antigen binding proteins can be expressed in hybridoma cell lines (e.g., in particular antibodies may be expressed in hybridomas) or in cell lines other than hybridomas. Expression constructs encoding the antigen binding proteins can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a polynucleotide encoding a polypeptide. The polypeptide may comprise one or more of the following: one or more CDRs such as provided herein; a light chain variable region; a heavy chain variable region; a light chain constant region; a heavy chain constant region (e.g., $C_H1$, $C_H2$ and/or $C_H3$); and/or another scaffold portion of a CD30L antigen binding protein. These nucleic acid sequences are inserted into an appropriate expression vector using standard ligation techniques. In one embodiment, the heavy or light chain constant region is appended to the C-terminus of a heavy or light chain variable region provided herein and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors can be purchased, for example, from Invitrogen Life Technologies (Carlsbad, Calif.) or BD Biosciences (San Jose, Calif.). Other useful vectors for cloning and expressing the antibodies and fragments include those described in Bianchi and McGrew, 2003, *Biotech. Biotechnol. Bioeng.* 84:439-44. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the polynucleotide encoding the polypeptide to be expressed, and a selectable marker element. The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Optionally, the vector may contain a "tag"-encoding sequence, i.e., an oligonucleotide molecule located at the 5' or 3' end of the CD30L antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the CD30L antigen binding protein from the host cell. Affinity purification can be accomplished, for example, by column chromatography using antibodies against the tag as an affinity matrix. Optionally, the tag can subsequently be removed from the purified CD30L antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Qiagen, Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds to CD30L. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding a CD30L antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding a heavy chain variable region or a light chain variable region of a CD30L antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene (Prinster et al., 1982, *Nature* 296:39-42); and prokaryotic promoters such as the beta-lactamase promoter (Villa- Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-fetoprotein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

After the vector has been constructed, the completed vector may be inserted into a suitable host cell for amplification and/or polypeptide expression. The transformation of an expression vector for an antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., Molecular Cloning: A Laboratory Manual, 3rd ed., Cold Spring Harbor Laboratory Press, Cold Spring Harbor, N.Y. (2001).

A host cell, when cultured under appropriate conditions, synthesizes protein that can be subsequently collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with CD30L binding properties. In another embodiment, a cell line from the B cell lineage that does not make its own antibody but has a capacity to make and secrete a heterologous antibody can be also selected. In another embodiment, fucosyltransferase knock-out cell lines that produce full or partial afucolylated antibodies (U.S. Pat. No. 6,946,292, U.S. Pat. No. 7,425,446, U.S. Pat. No. 7,846,725, U.S. Pat. No. 8,067,232, Potelligent® cells, BioWa, Princeton, N.J.

CD30L In Vitro Bioassays

Also provided are methods for identifying antagonists that inhibit CD30/CD30L interaction. These methods make use of induction of a marker cytokine produced from $CD30_+$ cells in response to CD30L. The method comprises the steps of combining a test compound of interest with a source of CD30L; adding the test compound/CD30L combination to $CD30^+$ cells that are capable of expressing a marker cytokine in response to the interaction of CD30 and CD30L; harvesting the cell supernatant; and determining the whether the test compound inhibits CD30/CD30L interaction by measuring the amount of a marker cytokine produced and/or released into the cell supernatant. For example, such a CD30L-dependent in vitro bioassay may exploit human Anaplastic Large Cell Lymphoma (ALCL) cell line, Karpas-299 (K299) expression of endogenous CD30 and release of IL-8 from these cells in response to the interaction of CD30 and CD30L. These methods are further exemplified in the Examples provided herein.

Test compounds include CD30L antigen binding proteins, including but not limited to antibodies, antigen binding fragments thereof and their derivatives. Test compounds could also include recombinant soluble CD30 compounds (such as CD30 extracellular domain fused with an Fc tag, poly-HIS tag, FLAG®-tag and the like) as well as small molecules. Suitable CD30+ cell lines express a marker cytokine in response to the interaction of CD30 and CD30L; such cell lines include human CD30$^+$ Anaplastic Large Cell Lymphoma cell line K299 (Karpas-299, DSMZ, Germany).

Sources for CD30L include soluble CD30L constructs and membrane associated CD30L. Soluble CD30L includes chimeric compositions comprising a CD30L fragment, preferably a fragment of the extracellular region of CD30L. Such soluble constructs include multimeric leucine or isoleucine zipper constructs. Such constructs comprise a 33 amino acid leucine zipper motif attached to the N-terminus of the extracellular domain of human or cynomolgus CD30L. Soluble recombinant CD30L constructs are also available commercially (R&D Systems, Minneapolis, Minn.). Other soluble CD30L also include CD30L extracellular domain fused to a FLAG®-tag (Axxora LLC, San Diego, Calif.). Membrane associated CD30L includes native and transfected CD30L expressing cells and cell lines. Such cell lines include, but are not limited to, such human cells as the CD30L$^+$ human B cell line Ramos (ATCC, Manassas, Va.). Also contemplated are cynomologous monkey blood T cells and mouse dendritic cell lines.

Provided herein is a method for determining CD30L induction of IL-8 production from CD30+ cells comprising the steps of: combining a test compound with a source of CD30L; adding the test compound-CD30L combination to irradiated CD30$^+$ cells; harvesting the cell supernatant; and determining the amount of IL-8 released into the cell supernatant. This CD30L-dependent in vitro bioassay exploits human Anaplastic Large Cell Lymphoma (ALCL) cell line, Karpas-299 (K299) expression of endogenous CD30 and release of IL-8 from these cells in response to the interaction of CD30 and CD30L. The released IL-8 can be quantified, for example, by an IL-8 ELISA. CD30L antagonists, such as antigen binding proteins described herein, are incubated with either soluble CD30L (single cell assay) or with a membrane associated CD30L (dual cell assay) and then cultured with K299 cells. The cell supernatants are then harvested and the inhibition of IL8 release from K299 cells in response to blocking by CD30L antagonists, such as the antigen binding proteins described herein, is determined using an IL-8 sandwich ELISA.

For the single cell assay, CD30L antagonists are titered into 96-well microtiterplates, such as Costar® 96 well plates (Corning; Acton, Mass.) to give a desired range of final concentrations, for example, from 1 µg/ml to 10 pg/ml. CD30L antigen binding proteins, such as those described herein, can be used as positive controls. The plates were incubated for about 45 minutes at room temperature. To each well was then added the CD30+ cell source. The plates were incubated for 24 hours at 37° C. 5% CO$_2$.

For the dual cell assay, the CD30L source is membrane bound and irradiated. CD30L expressing cells include, but are not limited to such cells as the human CD30L$^+$ human B cell line Ramos (ATCC, Manassas, Va.), activated cynomologous monkey blood T cells or mouse murine DC cell lines. The CD30L expressing cells may be subjected to FACS sorting prior to use to select those cells with the highest level of cell surface CD30L expression. The CD30L expressing cells are combined with the CD30L antagonist and incubated for 45 minutes prior to adding to the CD30+ cell source. Again, the plates are incubated for 24 hours at 37° C., 5% CO$_2$.

For both assays released IL8 may be determined and quantified by any method for detecting IL-8, such as, for example, an IL-8 sandwich ELISA. Such assays are commercially available, such as those provided by R&D Systems (Minneapolis, Minn.). IL-8 levels may be interpolated from the ELISA standard curve and IC$_{50}$ values determined using commercially available software, such as DeltaSoft (DeltaSoft, Inc., Hillsborough, N.J.) and GraphPad PRISM (GraphPad Software Inc., San Diego, Calif.).

Use of Human CD30L Antigen Binding Proteins for Diagnostic and Therapeutic Purposes Antigen binding proteins provided herein are useful for detecting CD30L in biological samples and identification of cells or tissues that produce CD30L. Antigen binding proteins that specifically bind to CD30L may be used in diagnosis and/or treatment of diseases related to CD30L in a patient in need thereof, for example, CD30L antigen binding proteins can be used in diagnostic assays, e.g., induction of IL-8 from CD30$^+$ cells. Antigen binding proteins that bind to CD30L may have therapeutic use in ameliorating diseases related to CD30L.

Indications

The present invention also relates to the use of CD30L antigen binding proteins for use in the prevention or therapeutic treatment of medical disorders, such as those disclosed herein. The CD30L antigen binding proteins are useful to treat a variety of conditions in which CD30L is associated with or plays a role in contributing to the underlying disease or disorder or otherwise contributes to a negative symptom.

Provided are methods for treating a variety of diseases, such as autoimmune and chronic inflammatory diseases and cancer by administering to a patient in need thereof an effective amount of a composition comprising one or more of the CD30L antigen binding proteins described herein. Such compositions are useful for modulating immune responses in vivo by blocking interactions between CD30$^+$ and CD30L$^+$ cells; depleting CD30L$^+$ cells; or by agonistic activity on CD30L$^+$ cells.

CD30L may exhibit "reverse signaling," CD30L expressed on neutrophils and peripheral blood T cells can be activated by cross-linking to stimulate metabolic activities in those cells (Wiley et al., *J Immunol* 157: 3235-39, 1996; Cerutti et al., *J. Immunol.* 165: 786, 2000; Cerutti et al., *Nat. Immunol.* 2: 150, 2001). As such, the antigen binding proteins described herein that bind CD30L could be used to block reverse CD30L signaling or stimulate CD30L$^+$ cells.

CD30$^+$ cells are strongly associated with Hodgkin's Disease and CD30 is a widely used clinical marker for a number of hematologic malignancies (for review, see Horie and Watanabe, *Immuno.* 10:457-470, 1998). Compositions comprising one or more of the CD30L antigen binding proteins described herein, either alone or in combination with other therapies, may be useful in treating such conditions.

CD30L is expressed on activated T cells and certain B cell and dendritic cell populations. CD30 is expressed on a proportion of activated T and B cells. This expression pattern suggests that targeting CD30L would be useful to modulate the interaction between T cells, B cells and dendritic cells. CD30L has been shown to affect humoral immunity. Antigen binding proteins described herein would be of use in therapeutic regimes related to inflammatory diseases, particularly those driven by T cell-dependent B cell responses.

Arthritis may be treated by the methods and compositions disclosed herein. As used here, the term "arthritis" refers to chronic inflammatory conditions that primarily affect joints, or the connective tissue surrounding joints, although various body organs may also become affected.

Arthritis may be autoimmune or traumatic in origin, or it may be triggered by exposure to a foreign antigen, thereafter leading to a chronic condition that is no longer dependent on the continued presence of the triggering antigen. The term "arthritis," as used herein, includes: arthritis deformans; osteoarthritis; rheumatoid arthritis (adult and juvenile); Lyme disease arthritis; reactive arthritis including Reiter's disease; psoriatic arthritis; arthritis nodosa; seronegative spondylarthropathies, including but not limited to ankylosing spondylitis.

The antigen binding proteins described herein are useful in treating a variety of rheumatic disorders, which are defined herein as any chronic disorder involving painful and often multiple localized inflammations of the joints, muscles, nerves, tendons, skin, eyes, connective tissues or various other organ systems. These include but are not limited to: arthritis; scleroderma; gout; systemic lupus erythematosus; polymyalgia rheumatica; Still's disease; chronic uveitis; disorders resulting in inflammation of the voluntary muscle, including dermatomyositis and polymyositis, including sporadic inclusion body myositis. Systemic lupus erythematosus can cause inflammation of the joints, skin, kidneys, heart, lungs, blood vessels and brain. In its advanced forms, systemic lupus erythematosus this condition can result in kidney failure.

Provided also are methods for using the antigen binding proteins described herein in therapies to treat various disorders of the endocrine system, including but not limited to: juvenile or maturity onset diabetes (including autoimmune, insulin-dependent types of diabetes; non-insulin dependent types and obesity-mediated diabetes); idiopathic adrenal atrophy; Addison's disease; hypothyroidism; Grave's disease; autoimmune thyroiditis, such as Hashimoto's thyroiditis; and polyglandular autoimmune syndromes (types I and II).

Antigen binding proteins described herein are also useful in therapies to treat conditions of the gastrointestinal system, including but not limited to: autoimmune sclerosing cholangitis; coeliac disease; inflammatory bowel diseases, including Crohn's disease and ulcerative colitis; autoimmune pancreatitis, including chronic pancreatitis; idiopathic gastroparesis; and idiopathic ulcers, including gastric and duodenal ulcers.

Included also are methods for using the antigen binding proteins described herein in therapies for treating disorders of the genitourinary system, such as autoimmune and idiopathic glomerulonephritis; and chronic idiopathic prostatitis (non-bacterial), including benign prostatic hypertrophy.

Also provided herein are methods for using the antigen binding proteins described herein in therapies to treat various hematologic disorders, including but not limited to: anemias and hematologic disorders, including pernicious anemia and aplastic anemia, and Fanconi's aplastic anemia; autoimmune hemolytic anemia; idiopathic thrombocytopenic purpura (ITP); myelodysplastic syndromes (including refractory anemia, refractory anemia with ringed sideroblasts, refractory anemia with excess blasts, refractory anemia with excess blasts in transformation); and autoimmune lymphoproliferative syndrome (ALPS).

The disclosed antigen binding proteins are furthermore useful to treat conditions that affect the liver such as autoimmune or chronic inflammatory hepatitis.

In addition, the disclosed antigen binding proteins and combination used to treat various autoimmune or chronic inflammatory disorders that involve hearing loss. One of these is inner ear or cochlear nerve-associated hearing loss that is thought to result from an autoimmune process, i.e., autoimmune hearing loss. This condition currently is treated with steroids, methotrexate and/or cyclophosphamide, which may be administered concurrently with an inhibitor or blocker of the CD30/CD30L interaction.

A number of inflammatory pulmonary disorders also can be treated with the disclosed antigen binding proteins, including: idiopathic lymphangioleiomyomatosis; chronic obstructive pulmonary disease (COPD) associated with chronic non-infectious bronchitis or with emphysema; and fibrotic lung diseases, such as cystic fibrosis and idiopathic pulmonary fibrosis.

Disorders associated with transplantation also are treatable with the disclosed antigen binding proteins, including graft-versus-host disease. To prevent or ameliorate graft-versus-host disease, compositions comprising one or more of the disclosed antigen binding proteins may be administered prior to, concomitantly with, or following bone marrow or solid organ transplantation, including transplantation of heart, liver, lung, skin, kidney or other organs.

The disclosed antigen binding proteins also are useful for treating chronic inflammatory eye diseases, including autoimmune uveitis.

Such compounds would also be useful for treating diseases associated with airway inflammation, such as asthma.

The antigen binding proteins described herein also are useful for treating inflammatory disorders that affect the female reproductive system, including: multiple implant failure/infertility; fetal loss syndrome or IV embryo loss (spontaneous abortion); and endometriosis.

Other medical disorders treatable with the antigen binding proteins described herein include chronic inflammation and/or degenerative diseases of the central nervous system. This includes, for example, diseases associated with demyelination, such as multiple sclerosis, systemic sclerosis and the Guillain-Barre syndromes (including acute inflammatory demyelinating polyneuropathy, acute motor axonal neuropathy, acute motor sensory axonal neuropathy and Fisher syndrome). Multiple sclerosis is representative of a chronic, degenerative disease of the central nervous system which may be treated with an agent capable of inhibiting or blocking the interaction of CD30 and CD30L.

See for example, U.S. Pat. No. 6,652,854.

Other chronic inflammatory conditions treatable with the disclosed antigen binding proteins include cold agglutinin disease; Behcet's syndrome; Sjogren's syndrome; and idiopathic tenosynovitis, as well as various chronic inflammatory disorders associated with hereditary deficiencies. The subject inhibitors, compositions and combination therapies furthermore are useful for treating Bell's palsy (idiopathic facial paralysis); chronic fatigue syndrome (not associated with ongoing infection); chronic degenerative vertebral disc disease; Gulf war syndrome; and myasthenia gravis, which may be treated concurrently with corticosteroids.

Disorders involving the skin or mucous membranes also are treatable using antigen binding proteins described herein. These include: acantholytic diseases, including discoid lupus, subacute cutaneous lupus erythematosus, cutaneous vasculitis, Darier's disease, keratosis follicularis, pemphigus vulgaris and paraneoplastic pemphigus; acne rosacea; alopecia areata; bullous pemphigoid; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; neutrophilic dermatitis (Sweet's syndrome); *pityriasis rubra* pilaris; psoriasis; pyoderma gangrenosum; loss of skin elasticity; and toxic epidermal necrolysis.

Other diseases that can be treated with the disclosed antigen binding proteins include: autoimmune-associated chronic mucocutaneous candidiasis; allergies; sarcoidosis; multicentric reticulohistiocytosis; Wegener's granulomatosis; arteritis, including giant cell arteritis; vasculitis and chronic autoimmune myocarditis.

To treat a medical disorder using the antigen binding proteins described herein, a therapeutically effective amount of a therapeutic agent is administered to a mammal in need thereof. The agent is administered according to a regimen of dose and frequency of administration that is adequate to induce a sustained improvement in at least one indicator that reflects the severity of the disorder. An improvement is considered "sustained" if the patient exhibits the improvement on at least two occasions separated by at least one day, but preferably that are separated by one week, two weeks, three weeks or four or more weeks. The severity of the disorder is determined based on signs or symptoms, or may be determined by questionnaires that are administered to the patient, such as the quality-of-life questionnaires often used by physicians to assess the status of chronic disease conditions.

One or more indicators that reflect the severity of a patient's illness may be assessed for determining whether the frequency and duration of drug treatment is sufficient. The baseline value for a chosen indicator is established by examination of the patient prior to administration of the first dose of the therapeutic agent. Preferably, the baseline examination is done within about 60 days of administering the first dose.

If the condition being treated is systemic lupus erythematosus, the indicator for determining sufficiency of treatment may consist of an observed improvement in one of the following: fatigue; fever; ulcers of the mouth and nose; facial rash ("butterfly rash"); photosensitivity (SLE often flares up after exposure to sunlight); pleuritis; pericarditis; Raynaud's phenomenon (reduced circulation to fingers and toes with exposure to cold); kidney function; and white blood cell count (SLE patients often have decreased numbers of white blood cells).

Pharmaceutical compositions comprising antigen binding proteins disclosed herein formulated with a pharmaceutically acceptable carrier are provided. In some embodiments, the pharmaceutically acceptable carrier is suitable for administration in human subjects.

Diagnostic Methods

The antigen binding proteins of the described can be used for diagnostic purposes to detect, diagnose, or monitor diseases and/or conditions associated with the CD30/CD30L interaction. Examples of methods useful in the detection of the presence of CD30L include immunoassays, such as the enzyme linked immunosorbant assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$O, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used.

Other diagnostic methods are provided for identifying a cell or cells that express CD30L. In a specific embodiment, the antigen binding protein is labeled with a labeling group and the binding of the labeled antigen binding protein to CD30L is detected. In a further specific embodiment, the binding of the antigen binding protein to CD30L is detected in vivo. In a further specific embodiment, the CD30L antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Other methods provide for detecting the presence of a test molecule that competes for binding to CD30L with the antigen binding proteins provided. An example of one such assay would involve detecting the amount of free antigen binding protein in a solution containing an amount of CD30L in the presence or absence of the test molecule. An increase in the amount of free antigen binding protein (i.e., the antigen binding protein not bound to CD30L) would indicate that the test molecule is capable of competing for CD30L binding with the antigen binding protein. In one embodiment, the antigen binding protein is labeled with a labeling group. Alternatively, the test molecule is labeled and the amount of free test molecule is monitored in the presence and absence of an antigen binding protein.

Methods of Treatment: Pharmaceutical Formulations, Routes of Administration

Pharmaceutical compositions that comprise a therapeutically effective amount of one or a plurality of the antigen binding proteins and a pharmaceutically acceptable excipient, diluent, carrier, solubilizer, emulsifier, preservative, and/or adjuvant are provided. In addition, methods of treating a patient by administering such pharmaceutical composition are included. The term "patient" includes human patients. The terms "treat" and "treatment" encompass alleviation or prevention of at least one symptom or other aspect of a disorder, or reduction of disease severity, and the like. The term "therapeutically effective amount" or "effective amount" refers to the amount of a CD30L antigen binding protein determined to produce any therapeutic response in a mammal. Such therapeutically effective amounts are readily ascertained by one of ordinary skill in the art. For purposes of this disclosure, the terms "illness," "disease," "medical condition," "abnormal condition," "malady," "medical disorder", "disorder" and the like are used interchangeably.

An antigen binding protein need not affect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. Certain methods provided herein comprise administering to a patient a CD30L antagonist (such as the antigen binding proteins disclosed herein) in an amount and for a time sufficient to induce a sustained improvement over baseline of an indicator that reflects the severity of the particular disorder.

As is understood in the pertinent field, pharmaceutical compositions comprising the molecules of the invention are administered to a patient in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds CD30L ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents for combination therapy. A pharmaceutical composition may comprise a CD30L antigen binding protein together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in any Remington's Pharmaceutical Sciences including the $21^{st}$ Ed. (2005), Mack Publishing Company, Easton, Pa.

Kits for use by medical practitioners include a CD30L antigen binding protein and a label or other instructions for use in treating any of the conditions discussed herein. In one embodiment, the kit includes a sterile preparation of one or more CD30L binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A typical dosage may range from about 0.1 μg/kg to up to about 30 mg/kg or more, depending on the factors mentioned above. In specific embodiments, the dosage may range from 0.1 μg/kg up to about 30 mg/kg, optionally from 1 μg/kg up to about 30 mg/kg, optionally from 10 μg/kg up to about 10 mg/kg, optionally from about 0.1 mg/kg to 5 mg/kg, or optionally from about 0.3 mg/kg to 3 mg/kg.

Dosing frequency will depend upon the pharmacokinetic parameters of the particular CD30L antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. A CD30L antigen binding protein of the invention may be administered, for example, once or more than once, e.g., at regular intervals over a period of time. In particular embodiments, a CD30L antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

It is contemplated that a CD30L antigen binding protein be administered to the patient in an amount and for a time sufficient to induce an improvement, preferably a sustained improvement, in at least one indicator that reflects the severity of the disorder that is being treated. Various indicators that reflect the extent of the patient's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionaires that are administered to the subject, such as quality-of-life questionaires developed for a given disease. Particular embodiments of methods and compositions of the invention involve the use of a CD30L antigen binding protein and one or more additional CD30L antagonists, for example, two or more antigen binding proteins of the invention, or an antigen binding protein of the invention and one or more other CD30L antagonists. Also provided are CD30L antigen binding proteins administered alone or in combination with other agents useful for treating the condition with which the patient is afflicted. Examples of such agents include both proteinaceous and non-proteinaceous drugs. Such agents include, for example, antagonists of TNFα, IL-1, IL-2, RANK or other cytokines that may contribute to autoimmunity or chronic inflammation. Cytokine antagonists include those that target the cytokine and/or its receptor. An antagonist that targets a cytokine may comprise a soluble receptor against the cytokine and usually includes part or all of the extracellular domain of a receptor for the cytokine. The soluble cytokine receptor may be used as a monomer, or as a dimer or higher multimer (for example, as a fusion molecule wherein the soluble receptor is attached to the dimer-promoting Fc portion of human immunoglobulin). In other embodiments, the soluble cytokine receptor is PEGylated to increase its serum half-life. In some embodiments, the soluble cytokine antagonist comprises a soluble TNF receptor (type I or II). Small organic molecules that inhibit inflammatory cytokines may also be used in combination with the subject therapeutic agents. More than one CD30 ligand antigen binding proteins and/or antigen binding regions thereof may be administered concurrently for treating autoimmune or chronic inflammatory diseases, and may be administered alone or together with other drugs that are effective against the same autoimmune or chronic inflammatory condition or that are being administered to treat a different condition in the same patient.

When multiple therapeutics are co-administered, dosages may be adjusted accordingly, as is recognized or known in the pertinent art. Such agents can be administered simultaneously, consecutively, alternately, or according to any other regimen that allows the total course of therapy to be effective.

In addition to human patients, CD30L antigen binding proteins are useful in the treatment of non-human animals, such as domestic pets (dogs, cats, birds, primates, etc.), domestic farm animals (horses cattle, sheep, pigs, birds, etc). In such instances, an appropriate dose may be determined according to the animal's body weight. For example, a dose of 0.2-1 mg/kg may be used.

Alternatively, the dose is determined according to the animal's surface area, an exemplary dose ranging from 0.1-20 mg/m2, or more preferably, from 5-12 mg/m2. For small animals, such as dogs or cats, a suitable dose is 0.4 mg/kg. CD30L antigen binding protein (preferably constructed from genes derived from the recipient species) is administered by injection or other suitable route one or more times per week until the animal's condition is improved, or it may be administered indefinitely.

The following Embodiments and Examples, including the experiments conducted and the results achieved, are provided for illustrative purposes only and are not to be construed as limiting the scope of the appended claims.

EMBODIMENTS

1. An isolated antigen binding protein that binds CD30L, comprising at least one heavy chain variable region comprising a CDRH1, a CDRH2 and a CDRH3 selected from the group consisting of:
    a) a CDRH1 that differs by no more than four amino acid substitution, insertion or deletion from a CDRH1 as shown in TABLE 3;
    b) a CDRH2 that differs by no more than seven amino acid substitutions, insertions and/or deletions from a CDRH2 as shown in TABLE 3;
    c) a CDRH3 that differs by no more than eleven amino acid substitutions, insertions and/or deletions from a CDRH3 as shown in TABLE 3; and
    comprising at least one light chain variable region comprising a CDRL1, a CDRL2 and a CDRL3 selected from the group consisting of:
    d) a CDRL1 that differs by no more than four amino acid substitutions, insertions and/or deletions from a CDRL1 as shown in TABLE 3;
    e) a CDRL2 that differs by no more than two amino acid substitution, insertion or deletion from a CDRL2 as shown in TABLE 3;
    f) a CDRL3 that differs by no more than two amino acid substitution, insertion or deletion from a CDRL3 as shown in TABLE 3.

2. An isolated antigen binding protein of embodiment 1 comprising:
    a CDRH1 selected from the group consisting of SEQ ID NOs:14, 15, 16, 17, 18, and 33;
    a CDRH2 selected from the group consisting of SEQ ID NOs: 19, 20, 21, 22, 23, 24 and 34;
    a CDRH3 selected from the group consisting of SEQ ID NOs: 25, 26, 27, 28, 29, and 35;
    a CDRL1 selected from the group consisting of SEQ ID NOs: 1, 2, 3, 4, 5, 6, and 30;
    a CDRL2 selected from the group consisting of SEQ ID NOs: 7, 8, 9, 10, and 31; and
    a CDRL3 selected from the group consisting of SEQ ID NOs: 11, 12, 13, and 32.

3. An isolated antigen binding protein that binds human CD30L comprising at least one light chain variable region selected from the group consisting of:
    a) a light chain variable region comprising a CDR1, CDR2 and CDR3, wherein the CDR1 comprising amino acid residues 23-36, the CDR2 comprising amino acid residues 52-58 and the CDR3 comprising amino acid residues 91-100 of SEQ ID NOs:36, 28, 40, 42, or 44; or
    b) a light chain variable region comprising a CDR1, CDR2 and CDR3, wherein the CDR1 comprising amino acid residues 25-36, the CDR2 comprising amino acid residues 52-58 and the CDR3 comprising amino acid residues 91-100 of SEQ ID NO:46; and
    at least one heavy chain variable region comprising a CDR1, CDR2 and CDR3, wherein the CDR1 comprising amino acid residues 31-35, the CDR2 comprising amino acid residues 50-65 and the CDR3 comprising amino acid residues 98-113 of SEQ ID NOs:48, 50, 52, 54, 56, 58, 60, 62, 64, 66, 68, 70 or 72.

4. An isolated antigen-binding protein of claim 1 that comprises at least one heavy chain variable region and at least one light chain variable region.

5. An isolated antigen-binding protein of embodiment 1 that comprises at least two heavy chain variable regions and at least two light chain variable regions.

6. An isolated antigen binding protein that binds CD30L comprising a heavy chain variable region and a light chain variable region, wherein the heavy chain variable region sequence differs by no more than 31 amino acid substitutions, additions and/or deletions from a heavy chain variable region sequence as shown in TABLE 2; and wherein the light chain variable region sequence differs by no more than 30 amino acid substitutions, additions and/or deletions from a light chain variable region sequence as shown in TABLE 1.

7. An isolated antigen binding protein that binds CD30L comprising
    a heavy chain variable region comprising of an amino acid sequence having at least 80% sequence identity to SEQ ID NO:48, 50, 52, 54, 56, 58, 60, 62, 64, 66, 68, 70, and 72; and
    a light chain variable region comprising an amino acid sequence having at least 88% sequence identity to SEQ ID NO: 36, 38, 40, 42, 44, and 46.

8. An isolated antigen binding protein that binds CD30L selected from the group consisting of
    a) an isolated antigen binding protein comprising a heavy chain variable region selected from the group consisting of of SEQ ID NOs:48, 50, 52, 54, 56, 58, 60 and 62 and a light chain variable region of SEQ ID NO: 36;

b) an isolated antigen binding protein comprising a heavy chain variable region of SEQ ID NO:64 and a light chain variable region of SEQ ID NO:38;
c) an isolated antigen binding protein comprising a heavy chain variable region of SEQ ID NO:66 and a light chain variable region of SEQ ID NO:40;
d) an isolated antigen binding protein comprising a heavy chain variable region of SEQ ID NO:68 and a light chain variable region of SEQ ID NO:42;
e) an isolated antigen binding protein comprising a heavy chain variable region of SEQ ID NO:70 and a light chain variable region of SEQ ID NO:44; and
f) an isolated antigen binding protein comprising a heavy chain variable region of SEQ ID NO:72 and a light chain variable region of SEQ ID NO:46.

9. An isolated antigen binding protein of any of the previous embodiments 1-8, wherein said antigen binding protein is an antibody.

10. An isolated antigen binding protein of embodiment 9, wherein said antibody is a monoclonal antibody, a recombinant antibody, a human antibody, a humanized antibody, a chimeric antibody, a multispecific antibody, or an antibody fragment thereof.

11. An isolated antigen binding protein of embodiment 10, wherein said antibody fragment is a Fab fragment, a Fab' fragment, a F(ab')$_2$ fragment, a Fv fragment, a diabody, or a single chain antibody molecule.

12. An isolated antigen binding protein of embodiment 10, wherein said antigen binding protein is a human antibody.

13. An isolated antigen binding protein of embodiment 10, wherein said antigen binding protein is a monoclonal antibody.

14. An isolated antigen binding protein of embodiment 9, wherein said antigen binding protein is of the IgG1-, IgG2- IgG3- or IgG4-type.

15. An isolated antigen binding protein of embodiment 14, wherein said antigen binding protein is of the IgG1- or IgG2-type.

16. An isolated antigen binding protein of any of the previous embodiments, wherein said antigen binding protein has at least one property selected from the group consisting of:
a) inhibiting CD30/CD30L interaction;
b) inhibiting CD30L-induced IL-8 induction;
c) cross-competing with one of antibodies A-F for binding to human CD30L;
d) a dissociation constant ≤70 pM and
e) binding to human CD30L with substantially the same $K_D$ as one of antibodies A-F.

17. An isolated antigen binding protein that binds CD30L, wherein the antigen binding protein binds a C-terminal region of CD30L defined by AA 201-234, or such as AA 205-230 or AA 211-226.

18. An isolated antigen binding protein of embodiment 17, wherein the antigen binding protein binds a further region of CD30L defined by AA 75-95 such as AA 80-90 or AA 82-88.

19. An isolated antigen binding protein of embodiment 17 or 18, wherein said antigen binding protein has at least one property selected from the group consisting of:
a) inhibiting CD30/CD30L interaction;
b) inhibiting CD30L-induced IL-8 induction;
c) cross-competing with one of antibodies A-F for binding to human CD30L;
d) a dissociation constant to human CD30L is at most 70 pM and
e) binding to human CD30L with substantially the same or lower Kd as one of antibodies A-F.

20. An isolated antigen binding protein of any of the previous embodiments 17-19, wherein binding of the antigen binding protein to hCD30L is inhibited by binding of a Fab of one or more of antibodies A, B, C, D, E and F.

21. An isolated antigen binding protein of any of the previous embodiments 17-19, wherein the antigen binding protein competes with a Fab of one or more of antibodies A, B, C, D, E and F for binding to CD30L.

22. An isolated antigen binding protein of any of embodiments 20-21, wherein the Fab is a Fab of antibody A1.

23. An isolated antigen binding protein of any of the previous embodiments 17-22, wherein said antigen binding protein has a dissociation constant ($K_D$) to human CD30L of at most 75 pM, such as at most 50 pM, such as 40 pM.

24. An isolated antigen binding protein of any of the previous embodiments 17-23, comprising a CDRH1, a CDRH2 and a CDRH3 and a CDRL1, a CDRL2 and a CDRL3,
wherein CDRL1 is the CDRL1 consensus sequence of SEQ ID NO:30,
wherein CDRL2 is the CDRL2 consensus sequence of SEQ ID NO:31,
wherein CDRL3 is the CDRL3 consensus sequence of SEQ ID NO:32,
wherein CDRH1 is the CDRH1 consensus sequence of SEQ ID NO:33,
wherein CDRH2 is the CDRH2 consensus sequence of SEQ ID NO:34 and
wherein CDRH3 is the CDRH3 consensus sequence of SEQ ID NO:35.

25. An isolated antigen binding protein of any of the previous embodiments 17-23, comprising a CDRH1, a CDRH2 and a CDRH3 and a CDRL1, a CDRL2 and a CDRL3,
wherein CDRL1 is the CDRL1 consensus sequence of SEQ ID NO:30,
wherein CDRL2 is the CDRL2 consensus sequence of SEQ ID NO:31,
wherein CDRL3 is the CDRL3 consensus sequence of SEQ ID NO:32,
wherein CDRH1 is the sequence of SEQ ID NO: 17 or the CDRH1 consensus sequence of SEQ ID NO:75,
wherein CDRH2 is the CDRH2 consensus sequence of SEQ ID NO:34 and
wherein CDRH3 is the CDRH3 consensus sequence of SEQ ID NO:35.

26. An isolated antigen binding protein of any of the previous embodiments 17-23, comprising a CDRH1, a CDRH2 and a CDRH3
wherein CDRL1 is the CDRL1 consensus sequence of SEQ ID NO:30,
wherein CDRL2 is the CDRL2 consensus sequence of SEQ ID NO:31,
wherein CDRL3 is the CDRL3 consensus sequence of SEQ ID NO:32,
and a CDRL1, a CDRL2 and a CDRL3,
wherein CDRH1 is the sequence of SEQ ID NO: 17 or the CDR1 consensus sequence of SEQ ID NO:75,
wherein CDRH2 is selected from sequence ID NO: 19, 20, 21, 22, 23 and 24 and
wherein CDRH3 is the CDRH3 consensus sequence of SEQ ID NO:35.

27. An isolated antigen binding protein of any of the previous embodiments 17-23, comprising a CDRH1, a CDRH2 and a CDRH3
   wherein CDRL1 is the CDRL1 consensus sequence of SEQ ID NO:30,
   wherein CDRL2 is the CDRL2 consensus sequence of SEQ ID NO:31,
   wherein CDRL3 is the CDRL3 consensus sequence of SEQ ID NO:32,
   and a CDRL1, a CDRL2 and a CDRL3,
   wherein CDRH1 is the sequence of SEQ ID NO: 17 or the CDRH1 consensus sequence of SEQ ID NO:75,
   wherein CDRH2 is selected from the group consisting of SEQ ID NO: 19, 20, 21, 22, 23 and 24 and
   wherein CDRH3 is selected from the group consisting of SEQ ID NO: 25, 26, 27, 28 and 29.

28. An isolated antigen binding protein of any of the previous embodiments 17-23 comprising:
   a CDRH1 selected from the group consisting of SEQ ID NOs:14, 15, 16, 17 and 18;
   a CDRH2 selected from the group consisting of SEQ ID NOs: 19, 20, 21, 22, 23 and 24;
   a CDRH3 selected from the group consisting of SEQ ID NOs: 25, 26, 27, 28 and 29;
   a CDRL1 selected from the group consisting of SEQ ID NOs: 1, 2, 3, 4, 5 and 6;
   a CDRL2 selected from the group consisting of SEQ ID NOs: 7, 8, 9 and 10; and
   a CDRL3 selected from the group consisting of SEQ ID NOs: 11, 12 and 13.

29. An isolated antigen binding protein of any of the previous embodiments 17-23 comprising:
   a) CDRH1, CDRH2 and CDRH3 identified by SEQ ID NOs: 14, 19, 25 and CDRL1, CDRL2 and CDRL3 identified by SEQ ID NO: 1, 7 and 11,
   b) CDRH1, CDRH2 and CDRH3 identified by SEQ ID NOs:15, 21, 26 and CDRL1, CDRL2 and CDRL3 identified by SEQ ID NO: 2, 8 and 12,
   c) CDRH1, CDRH2 and CDRH3 identified by SEQ ID NOs:15, 21, 26 and CDRL1, CDRL2 and CDRL3 identified by SEQ ID NO: 3, 8 and 12,
   d) CDRH1, CDRH2 and CDRH3 identified by SEQ ID NOs:16, 22, 27 and CDRL1, CDRL2 and CDRL3 identified by SEQ ID NO: 4, 9 and 12,
   e) CDRH1, CDRH2 and CDRH3 identified by SEQ ID NOs:17, 23, 28 and CDRL1, CDRL2 and CDRL3 identified by SEQ ID NO: 5, 8 and 13 or
   f) CDRH1, CDRH2 and CDRH3 identified by SEQ ID NOs:18, 24, 29 and CDRL1, CDRL2 and CDRL3 identified by SEQ ID NO: 6, 10 and 12.

30. An antigen binding protein that competes with at least one antigen binding protein of any of embodiments 1 to 29.

31. An antigen binding protein of any of embodiments 1 to 29 that is fully or partially afucosylated 32. An isolated nucleic acid molecule encoding an antigen binding protein of any of the previous embodiments.

33. An isolated nucleic acid molecule of embodiment 32, wherein at least one heavy chain variable region is encoded by an isolated nucleic acid molecule selected from the group consisting of SEQ ID NOs:49, 51, 53, 55, 57, 59, 61, 63, 65, 67, 69, 71 and 73 and at least one light chain variable region is encoded by an isolated nucleic acid molecule selected from the group consisting of SEQ ID NOs: 37, 39, 41, 43, 45, and 47.

34. A nucleic acid molecule according to embodiment 33, wherein said nucleic acid molecule is operably linked to a control sequence.

35. A vector comprising a nucleic acid molecule according to embodiment 32.

36. A host cell comprising the nucleic acid molecule according to embodiment 32.

37. A host cell comprising the vector according to embodiment 35.

38. An isolated polynucleotide sufficient for use as a hybridization probe, PCR primer or sequencing primer that is a fragment of the nucleic acid molecule of embodiment 33 or 34 or its complement.

39. A method of making the antigen binding protein of any of embodiments 1 to 31, comprising the step of preparing said antigen binding protein from a host cell that secretes said antigen binding protein.

40. A pharmaceutical composition comprising at least one antigen binding protein of any of embodiments 1 to 31 and pharmaceutically acceptable excipient.

41. A pharmaceutical composition of embodiment 40, further comprises a labeling group or an effector group.

42. A pharmaceutical composition of embodiment 41, wherein said labeling group is selected from the group consisting of isotopic labels, magnetic labels, redox active moieties, optical dyes, biotinylated groups and predetermined polypeptide epitopes recognized by a secondary reporter.

43. A pharmaceutical composition of embodiment 42, wherein said effector group is selected from the group consisting of a radioisotope, radionuclide, a toxin, a therapeutic group and a chemotherapeutic group.

44. A method for treating or preventing a condition associated with CD30L in a patient, comprising administering to a patient in need thereof an effective amount of at least one isolated antigen binding protein of any of embodiments 1 to 31.

45. A method of embodiment 44, wherein the isolated antigen-binding protein is administered alone or as a combination therapy.

46. A method of reducing CD30L activity in a patient comprising administering an effective amount of at least one antigen binding protein of any of embodiments 1 to 31.

47. An antigen binding protein according to any of the previous embodiments 1 to 31 for use in a method of treatment.

48. An antigen binding protein according to any of the previous embodiments 1 to 31 for treatment of flammatory diseases.

49. An antigen binding protein according to any of the previous embodiments 1 to 31 for treatment of autoimmune diseases, such as arthritis (including rheumatoid arthritis (RA), and Systemic Lupus Erythematosus (SLE), inflammatory bowel diseases (IBD), including Crohn's disease and ulcerative colitis.

EXAMPLES

Example 1

Generation of Human CD30L Antibodies

XenoMouse™ technology (Amgen, Thousand Oaks, Calif.) was used to develop human monoclonal antibodies that recognize and inhibit recombinant human CD30L activity. The antibodies selected were cross reactive with human and cynomologous CD30L, but not with mouse CD30L.

Hybridoma supernatants were screened by fluorometric microvolume assay technology (FMAT) for binding to recombinant human CD30L expressed on 293T cells as well as being screened by fluorescence-activated cell sorting (FACs) analysis for binding to native human CD30L on Ramos cells. In the FMAT assay, plates are coated with 293T cells expressing CD30L, hybridoma supernatant was added, and a secondary anti-human Ig antibody was then added for detection via standard ELISA techniques. Negative controls were the corresponding non-transfected 293T cells that did not express CD30L.

The supernatants were purified and recombinant antibodies were expressed as IgG1 and IgG2 constructs. The antibodies were rescreened for binding to native human and cynomologous monkey CD30L. Briefly, human Burkitt's lymphoma Ramos cells ($3\times10^5$/well) were incubated in round-bottomed 96-well microtiter plates (Costar® 96 well plate (Corning; Acton, Mass.) with a titration (10 μg/mL to 3.2 ng/mL final concentration) of anti-CD30L IgG antibodies in blocking buffer (PBS containing 0.02% sodium azide, 2% normal goat serum and 1% normal rabbit serum). Human CD30.Fc fusion protein was included as a positive control for binding. Cells were incubated for 30 minutes at 4° C. then washed X2 with PBS and incubated for a further 30 minutes at 4° C. with 30 μL/well of anti-hu IgG-biotin (1:50 in blocking buffer; Jackson Immunoresearch, West Grove, Pa.). After washing X2 with PBS, cells were incubated for 30 minutes at 4° C. with 30 μL/well (1:50 dilution in PBS) of Streptavidin-Phycoerythrin (PE; Molecular Probes, Eugene, Oreg.). Cells were washed 2× with PBS and prepared for FACs analysis. Results can be found in Table 5.

Cynomologous activated T cells were prepared by isolating peripheral blood mononuclear cells (PBMC) from heparinized cynomolgus monkey blood by density centrifugation over Isolymph (2000 rpm. for 20 minutes). PBMC were resuspended in 25 mLs of PBS, added to 300 μl of a 50% solution of 2-Aminoethylisothiouronium bromide (AET)-treated sheep erythrocytes and centrifuged at ~700 rpm at 4° C. for 10 minutes. Pelleted cells were incubated at 4° C. for a further 20 minutes, gently resuspended and centrifuged over Isolymph. Supernatant was removed down to the T cell/erythrocyte pellet. The pellet was then resuspended in 25 mL of lyses buffer (0.85% ammonium chloride in water) and incubated at 37° C. for 10 minutes. The resultant T cells were pelleted and washed ×2 in culture medium (RPMI-1640 medium+10% heat-inactivated fetal bovine serum) and then cultured ($1\times10^6$/mL) at 37° C. for 18 hr in the presence of 10 ng/mL Phorbol Myristate Acetate (PMA; Sigma Chemicals, St Louis, Mo.) and 500 ng/mL Ionomycin (Calbiochem, San Francisco, Calif.). At the end of the culture period, cynomolgus T cells were counted and washed 1× with PBS and incubated with 2% Goat serum, 1% Rabbit serum and 0.1% Human serum in PBS for 30 minutes at 4° C. Cells were then stained with anti-huCD30L antibodies as described above for human Ramos cells. Results can be found in Table 5.

The antibodies were also screened for ability to block binding of human CD30L to a soluble human CD30.Fc molecule. Briefly, human Ramos cells or activated cynomolgus monkey T cells were incubated with anti-CD30L IgGs at 50 g/mL in blocking buffer for 30 minutes at 4° C. Soluble huCD30.Fc-His was then added at a final concentration of 2.5 ug/mL (30 μL/well) and incubated for 30 minutes at 4° C. Cells were washed X2 with PBS and incubated with 5 μg/mL of a mouse anti-His monoclonal antibody (30 μL/well in blocking buffer) and incubated for 30 minutes at 4° C. After washing X2 with PBS, cells were incubated with anti-mouse IgG-PE (1:50 in PBS; BD Pharmingen, San Diego, Calif.) for a further 30 minutes at 4° C. Cells were then washed X2 with PBS and prepared for FACs analysis. The results can be found in Table 5.

Example 2

CD30L Antibody Functional Screen

The antibodies were characterized for their ability to block CD30L/CD30 interactions using two IL-8 release assays. These assays exploit the human Anaplastic Large Cell Lymphoma (ALCL) cell line Karpas-299 (K299), which expresses endogenous CD30 and releases IL-8 in response to CD30L. Briefly, purified anti-human CD30L IgG antibodies were incubated with either recombinant CD30L (single cell assay) or Ramos cells expressing native CD30L (dual cell assay) and cultured with K299 cells. After a defined incubation period, the cell supernatants were harvested and analyzed for IL-8 content using a sandwich ELISA to determine inhibition of IL-8 release from K299 cells in response to CD30L by antibody candidates.

Single Cell Assay

Anti-CD30L IgG antibodies were titrated into culture diluent (RPMI-1640 medium+10% heat-inactivated fetal bovine serum) and placed into round-bottomed 96-well microtiter plates (Costar® 96 well plate (Corning; Acton, Mass.) to give a range of final concentrations from 1 μg/ml to 10 pg/ml. As a positive control, a mouse anti-human CD30L monoclonal antibody was prepared as described in U.S. Pat. No. 5,480,981. The final volume of diluent and CD30L IgG was 100 μl/well. To each well was then added 50 μl of recombinant human CD30L isoleucine zipper (huCD30L LZ). The huCD30L LZ construct consists of the extracellular domain of human CD30L (see U.S. Pat. No. 5,480,981) linked at its N-terminus to an isoleucine zipper motif modified by replacing the leucine residues with isoleucine residues. The single cell assay was also used to determine cyno cross-reactivity using a cyno CD30L LZ instead of the huCD30L LZ. CynoCD30L LZ was prepared as described for the human LZ molecule.

The plates were incubated for 45 minutes at room temperature. To each well was added 50 μl of K299 cells ($4\times10^5$ cells/ml). The plates were then incubated for 24 hours at 37° C. 5% $CO_2$.

The amount of IL-8 in the cell supernatants was determined by sandwich ELISA, using a CDCL8/IL-8 ELISA DuoSet kit according to the manufacturer's instructions (R&D Systems, Minneapolis, Minn.). IL-8 levels were interpolated from the ELISA standard curve using DeltaSoft 3 version 2.2 software (DeltaSoft, Inc. Hillsborough, N.J.). All results were expressed as the mean±standard error of the mean (SEM) for 3 replicate cultures calculated by GraphPad PRISM software v. 4.01 (GraphPad Software Inc., San Diego, Calif.) as were the $IC_{50}$ values. The $IC_{50}$ value derived using the huCD30L LZ for Antibody A1 was 2700 pM. The results using the cynoCD30L LZ can be found in Table 5.

Dual Cell Assay

As described above, anti-CD30L IgG antibodies were titrated into culture diluent and placed into round-bottomed 96-well microtiter plates to give a range of final concentrations from 1 μg/ml to 10 pg/ml. The final volume of diluent and CD30L IgG was 100 μl/well. To each well was added 50 μl irradiated (5000 RADS) $CD30L^+$ Ramos cells ($4\times10^6$/ml, ATCC). The Ramos cells were subjected to FACS sorting to select those cells with the highest level of cell surface CD30L expression.

The plates were incubated for 45 minutes at room temperature. To each well was added 50 µl of K299 cells ($4 \times 10^5$ cells/ml). The plates were incubated for 24 hours at 37° C. 5% $CO_2$.

The amount of IL-8 in the culture supernatants was determined by sandwich ELISA, using a CDCL8/IL-8 ELISA DuoSet kit according to the manufacturer's instructions (R&D Systems, Minneapolis, Minn.). The amount of IL-8 and $IC_{50}$ values were calculated as described above, see Table 5.

Antibody leads were selected based on their ability to inhibit CD30L-induced IL-8 induction compared with the mouse anti-human CD30L monoclonal antibody control.

twice with ice cold FACS buffer (1× D-PBS+2% FBS). The cells were then incubated with a secondary antibody goat anti-human Fc Cy5 (Jackson Immuno Research, West Grove, Pa.,) and with 7AAD (BD-Biosciences, Rockville, Md.) for 1 h on ice in the dark. Following the incubation, the cells were washed twice with ice-cold FACS buffer before flow cytometry analysis. The GeoMean values of FL4 shift gated on live cell population measure the bound [Ab]. The inverse of the GeoMean values that reflects theoretical free [Ag] in the equilibrium solution was then calculated. The inverse values of the GeoMean read were used in KinExA software for analysis and Kd calculation for each antibody. The free [Ag] measure was plotted against the starting

TABLE 5

Table of mean $IC_{50}$ (pM) and % inhibiton for CD30L antibodies in various functional assays

| Assays | Antibodies | | | | | | | |
|---|---|---|---|---|---|---|---|---|
| | A | E | F | C | D | B | A1 | A1 IgG1 |
| Native huCD30L (K299/Ramos dual cell, $IC_{50}$) Native Binding (FACS, $EC_{50}$) | 28 pM | 45 pM | 60 pM | 36 pM | 62 pM | 72 pM | 33 pM | 32 pM |
| Hu Cyno CD30L LZ Blocking (Binding to K299, $IC_{50}$) | 1.7 nM 2.2 nM | 3.3 nM 2.7 nM | 2.3 nM 2.9 nM | 1.7 nM 1.0 nM | 3.3 nM 2.7 nM | 3.1 nM 4.0 nM | | |
| Hu Cyno Native Blocking (CD30Fc binding, % inhibition) | 1.5 nM 1.4 nM | 2.1 nM 1.3 nM | 2.0 nM 0.45 nM | 1.9 nM | | | 2.5 nM | 1.4 nM |
| Hu Cyno Cyno CD30L LZ (K299/Single Cell, $IC_{50}$) | 68% 77% 2.0 nM | 80% 87% 5.4 nM | ND 97% 5.5 nM | 88% 83% 3.9 nM | 55% 84% 5.4 nM | 70% 88% 5.6 nM | 2.4 nM | 1.5 nM |
| Theoretical isoelectric point | 8.89 | 8.86 | 8.96 | 8.74 | 9.01 | 8.84 | | |

Example 3

Binning of CD30L Antibodies by Binding Competition

Binning was performed using a binding competition assay in which one labeled CD30L antibody competed with excess amounts of other unlabeled CD30L antibodies for binding to rhCD30L. Antibodies which competed with one another were assigned to the same bin. Antibodies A-F competed with each other for binding to rhCD30L.

Example 4

Determining the On-Cell Equilibrium Dissociation Constant (Kd) for CD30L Antibodies Binding affinity of CD30L antibodies to CD30L expressed on Ramos cells were determined by FACS Kd method. The Ramos cells were cultured in RMP11640 media+10% FBS+L-glut+0.05% azide. Two equilibrium reactions were set up where the antibodies were titrated 1:3 from 60 nM to 338 fM using cell culture media and incubated with two different constant cell concentrations (25000 and 250000 cells). The plates were sealed with parafilm and incubated at 37° C., 20 h, shaking. The equilibrium plates were centrifuged and cell pellets were washed concentration of titrating component and from these plots at two different cell concentrations the Kd was obtained from curve fitting using n-curve analysis in KinExA™ Pro software. The 95% confidence interval is given as Kd low and Kd high.

As seen in the Table 6, the antibodies have high affinity to CD30L expressed on Ramos cells. All had Kd values in the low pM range.

TABLE 6

Table of $K_D$ (pM) rates

| Antibody | Kd (pM) | Kd low (pM) | Kd high (pM) |
|---|---|---|---|
| B | 7.43 | 4.58 | 11.70 |
| A | 25.46 | 18.15 | 33.10 |
| D | 11.90 | 8.44 | 16.14 |
| E | 52.08 | 38.29 | 69.56 |
| F | 35.75 | 26.92 | 46.64 |
| C | 43.99 | 34.15 | 56.02 |

Example 5

ADCC Assay

The variable domains from A1 were attached to a human IgG1 constant domain (A1 IgG1). This antibody was expressed in a Fut-8 knock-out CHO cell line resulting in an afucosylated antibody, A1 IgG1f.

CD30L antibody mediated killing of target cells was assessed in an antibody dependent cytotoxicity (ADCC) assay. Target cell Ramos (CD30L expression level high), JD38 (CD30L expression level moderate), DS179 (CD30L expression level low) and EW36 (no CD30L expression), were harvested and resuspended at $2 \times 10^6$ cells/ml in cRPMI-10 media (RPMI (Life Technologies, Carlsberg, Calif.)+10% fetal bovine serum). Calcein-AM, 4 MM in anhydrous DMSO (Sigma-Aldrich, St. Louis, Mo.) was added to final concentration of 10 μM (1:400 dilution). Cells were incubated for 30 minutes at 37° C. followed by two washes in PBS (1500 rpm, 5 minutes at 4° C. each). Pellets were resuspended in cRPMI-10 and adjusted to a concentration of $0.2 \times 10^6$ cells/mL placed on ice for the use in the next step.

Antibody A1 IgG1 and Antibody A1 IgG1f were first added to U-bottom 96-well plates (BD, Franklin Lakes, N.J.) at 10 fold serial titration starting from 10 ug/ml. Rituximab (Genentech, South San Francisco, Calif.) was used as a positive antibody control. Antibody A1 (IgG2) was added as a negative control. Calcein-AM-labeled target cells, described above, were then added to each well (10,000 cells/well) and incubated with antibodies for 20 minutes at 37° C. Following incubation, each well was added 50 μl of NK cells at a concentration of $4 \times 10^6$ cells/ml and incubated for 4 hours at 37° C. NK cells were pelleted (1500 rpm, 5 minutes at 4° C.) and resuspended in cRPMI-10, adjusting the cell concentration to $4 \times 10^6$ cells/mL.

Following incubation controls wells were prepared by adding 20 μl/well 9% NP-40 (IGEPAL CA 630, Sigma-Aldrich) to stimulate 100% lysis. All other wells received 20 μl/well of cRPMI-10 media alone. The plates were spun at 800 RPM for 4 minutes at 4° C. Supernatant (150 μl) was removed and transferred to a clear bottom, black 96 well plate (Corning, Lowell, Mass.) and fluorescence read on plate reader (Molecular Devices, Spectra max GEMINI), excitation 485, emission 535.

Percent maximum lysis was calculated as (sample value−spontaneous lysis)/(100% lysis−spontaneous lysis)*100.

The results of CD30L antibody mediated killing of the four target cells are shown in FIG. 1 (A-D). Antibody A1 IgG1 did not mediate cell killing on any of the CD30L expressing cells (see FIGS. 1A-D). Antibody A1 IgG1f induced cell death on target cells with both high CD30L expression (see FIG. 1A) and on target cells with moderate CD30L expression (see FIG. 1B). Antibody A1 IgG1f mediated a greater level of depletion on target cells with higher CD30L expression than on targets cells with moderate levels of CD30L (see FIGS. 1A and 1B). Antibody A1 IgG1f did not kill target cells with low (C) or no (D) CD30L expression

Example 6

Epitope Mapping by HX-MS of Anti-CD30L mAbs

The CD30L binding regions of anti-CD30L antibodies were evaluated by HX-MS to identify region or regions of human CD30L involved in the molecular interaction with the antibodies A to F described herein.

Materials hCD30L: Two different versions of the extracellular domain of hCD30L were used His-hCD30L-EC contains residues 63-234 of hCD30L as identified by SEQ ID NO: 74 and as the name indicates the protein is produced with an N-terminal His-tag (RnD Systems). FLAG-hCD30L-EC contains residues 66-234 of SEQ ID NO: 74 and was obtained from mammalian cells with an N-terminal FLAG-His-tag.

The cDNA of extracellular domain of human CD30L was purchased from Origene. FLAG-His6 tag and a TEV protease cleavage site was fused to the N-terminus of the coding sequence for amino acids 66-234 by a two-step extension PCR and cloned between EcoRI and BamHI sites of pJSV001 plasmid in frame with a CD33 signal peptide.

The FLAG-hCD30L-EC used below includes an N153Q point mutation that abolishes an N-glycosylation. The N153Q mutant was generated with Qiagen quick-change point mutagenesis Kit (QIAGEN).

HEK293 6E cells were used for protein production. The cells were cultured with FreeStyle™ medium (Gibco) supplemented with 25 ug/ml Geneticin 418 (Gibco) and 0.1% F-68(Gibco). On the day of transfection, cells were kept at a density of $1 \times 10^6$ cell/ml and transfected with 293 Fectin (Invitrogen) according to manufacturer's instruction. 24 hr posttransfection, peptone (Promega) was added to the culture to a final concentration of 0.5%. Cells were continued to grow for 5 days before the supernatant was collected.

The culture supernatant was harvested by centrifugation (15,000 rpm×20 min, 4° C.) and then cleared by the filtration with 0.22 μm cellulose nitrate membrane. The cleared supernatant was applied to Ni-chelated sepharose XK60 column (20 ml) (GE healthcare), followed by a 10 column volume wash with 20 mM NaH2PO4 pH7.4, 0.5M NaCl. The protein was then eluted with a 5 column volume of 20 mM NaH2PO4 pH7.4, 0.5M NaCl, 0.5M imidazole. The eluted proteins were pooled, concentrated to 5 ml by Amicon ultra 15 centrifugal units (10,000 Da MWCO, Millipore) and loaded onto a Hiload 26/60 Superdex 200 318 ml column (GE Healthcare) to remove aggregates and buffer-exchange to PBS. After concentrating, the final protein concentrations were determined by measuring 280 nm absorbance with a NANODROP UV spectrometer. Protein purity was assessed by SDS-PAGE.

Deglycosylations were performed for approximately 16 h at 37° C. using 1U PNGaseF (Roche) per 5 ug hCD30L. The deglycosylated protein was stored at 4 C and used for experiments within one week. All proteins were buffer exchanged into PBS pH 7.4 before HX-MS experiments.

HX-MS Experiments

Instrumentation and Data Recording

The HX experiments were performed on a nanoACQUITY UPLC System with HDX Technology (Waters Inc.) coupled to a Synapt G2 mass spectrometer (Waters Inc.). The Waters HDX system contained a Leap robot (H/D-x PAL; Waters Inc.) operated by the LeapShell software (Leap Technologies Inc/Waters Inc.), which performed initiation of the deuterium exchange reaction, reaction time control, quench reaction, injection onto the UPLC system and digestion time control. The Leap robot was equipped with two temperature controlled stacks maintained at 20° C. for buffer storage and HX reactions and maintained at 2° C. for storage of protein and quench solution, respectively. The Waters HDX system furthermore contained a temperature controlled chamber holding the pre- and analytical columns, and the LC tubing and switching valves at 1° C. A separately temperature controlled chamber holds the pepsin column at 25° C. For the inline pepsin digestion, 100 μL quenched sample containing 300 pmol hCD30L was loaded and passed over a Poroszyme® Immobilized Pepsin Cartridge (2.1×30 mm (Applied Biosystems)) placed at 25° C. using a isocratic flow rate of 100 μL/min (0.1% formic acid:$CH_3CN$ 95:5). The resulting peptides were trapped and desalted on a VanGuard pre-column BEH C18 1.7 μm (2.1×5 mm (Waters Inc.)). Subsequently, the valves were switched to place the pre-column inline with the analytical column, UPLC-BEH C18 1.7 μm (1×100 mm (Waters Inc.)), and the peptides separated using a 9 min gradient of 10-50% B delivered at 40 μl/min from the nanoAQUITY UPLC system (Waters Inc.). The mobile phases consisted of A: 0.1% formic acid and B: 0.1% formic acid in $CH_3CN$. The ESI MS data, and the separate elevated energy ($MS^E$) experiments were acquired in positive ion mode using a Synapt G2 mass spectrometer (Waters Inc.). Leucine-enkephalin was used as the lock mass ($[M+H]^+$ ion at m/z 556.2771) and data was collected in continuum mode (For further description, see Andersen and Faber, Int. J. Mass Spec., 302, 139-148 (2011)).

Data Analysis

Peptic peptides were identified in separate experiments using standard $MS^E$ methods where the peptides and fragments are further aligned utilizing the ion mobility properties of the Synapt G2 (Waters Inc.). $MS^E$ data were processed using ProteinLynx Global Server version version 2.5 (Waters Inc.). The HX-MS raw data files were processed in the DynamX 2.0 software (Waters Inc.). DynamX automatically performs the lock mass-correction and deuterium incorporation determination, i.e., centroid determination of deuterated peptides. Furthermore, all peptides were inspected manually to ensure correct peak and deuteration assignment by the software.

Epitope Mapping Experiment

Amide hydrogen/deuterium exchange (HX) was initiated by a 6-fold dilution of hCD30L in the presence or absence of mAb A, B, C, D, E or F into the corresponding deuterated buffer (i.e. PBS prepared in $D_2O$, 96% $D_2O$ final, pH 7.4 (uncorrected value)). All HX reactions were carried out at 20° C. and contained 6 μM hCD30L (monomeric Mw used) in the absence or presence of 6.6 μM mAb thus giving a 2.2 fold molar excess of mAb. At time intervals 0.25, 0.5, 1, 3 and 10 minutes, 50 μl aliquots of the HX reaction were quenched by 50 μl ice-cold quenching buffer (1.35M TCEP) resulting in a final pH of 2.5 (uncorrected value).

Results hCD30L Proteins

The presence of glycosylations in hCD30L would hamper an HXMS analysis. Because of the unknown mass and often heterogeneous nature of protein glycosylations, the resulting peptic peptides cannot be identified and analyzed in MS. However, removing of the glycosylations from hCD30L could create a well-defined amino acid sequence suitable for HXMS as it can be identified and analyzed in MS.

The hCD30L extracellular domain contains five potential N-glycosylation sites as listed in the first column of Table 7 below. The glycosylations were attempted removed both by treatment with PNGaseF and by point mutation to obtain a protein better suited for HXMS analysis.

MS and SEC-MALS analyses of His-hCD30L-EC showed that four out of the five potential N-glycosylation sites was indeed glycosylated (Table 7; data not shown). Upon treating this protein with PNGaseF under native conditions, only two of the glycosylations could be enzymatically removed by PNGaseF and thus two N-glycosylations remained on the protein.

Upon treating FLAG-hCD30L-EC with PNGaseF under native conditions, both MS and SEC-MALS demonstrated that this protein could be fully deglycosylated. In conclusion the N153Q mutation abolishes an N-glycosylation site that could not be enzymatically removed from His-hCD30L-EC and this protein was considered optimal for HXMS. An overview of the glycosylation site(s) evaluation is included in Table 7.

TABLE 7

Status of glycosylations in the different versions of hCD30L protein

| Potential N-glycosylation site of CD30L | His-hCD30L-EC | His-hCD30L-EC + PNGaseF | FLAG-hCD30L-EC (N153Q) | FLAG-hCD30L-EC + PNGaseF |
|---|---|---|---|---|
| N81 | Glyc | D | Glyc | D |
| N109 | Glyc | D | Glyc | D |
| N153 | Glyc | Glyc | Q | Q |
| N189 | N | N | N | N |
| N201 | Glyc | Glyc | Glyc | D |

D, N, Q denotes the presence of the unmodified amino acid at the sequence position.
Glyc denotes the presence of N-glycosylations HX-MS Analysis After deuterium exchange reaction, hCD30L-EC is digested with pepsin yielding the peptic peptide regions described in Table 8. Numbering of hCD30L residues follows SEQ ID NO 74, however the N-terminal FLAG-His tag DYKDDDDKHHHHHHENLYFQG (SEQ ID NO: 76) is not part of the hCD30L sequence. The HX time-course of 40 peptic peptides, covering 83% of the primary structure of FLAG-hCD30L-EC were monitored in the absence or presence of mAb A, B, C, D, E or F and data included in Table 8.

The remaining sequence not analyzed in the present study was covered with peptic peptides; however the signal intensity was insufficient for data analysis. The observed exchange pattern in the early time-points (<10 min) in the presence or absence of mAbs A1, B, C, D, E or F can be divided into two different groups: One group of hCD30L-EC peptic peptides display an exchange pattern that is unaffected by the binding of mAbs. In contrast, another group of peptides in hCD30L show protection from exchange upon mAb binding (Table 8). In the case of overlapping peptic peptides, the exchange protection information is attempted sub-localized to specific residues or stretches within the peptide assuming full back-exchange of the peptide N-terminus and first peptide bond. Exchange protection in a peptide is indicative of this region being involved in mAb binding. Thus the epitope is partly or fully located within the region defined by the specific peptides. However, since the resolution of HX-MS is based on pepsin digestion of the deuterated protein, exchange protection within a given region does not imply that every residue within the region defined by the peptic peptides necessarily is involved in mAb binding.

Epitope Mapping of mAb A 1

The epitope of mAb A1 was mapped in four different experiments using FLAG-hCD30L-EC three times and using His-hCD30L-EC once. Both proteins were treated with PNGaseF before HX-MS experiments. The outcomes of these studies were highly similar independent of the hCD30L protein used and all yielded the same epitope information. However, the sequence coverage was obviously lower in the His-hCD30L-EC experiment due to the lack of detectable peptides in the glycosylated regions.

Epitope signal for mAb A1 was observed in the N-terminal region of hCD30L (Table 8) up until residue Cys88. The exchange protection became stronger the longer the peptides extended from the starting points (residues 45, 62 or 66) thus indicating exchange protection in the more C-terminal region of the peptides and also in residue 88. In contrast the peptides 45-65, 45-81 and 66-81 did not show exchange protection. Furthermore, residue D81 is the glycosylation site where glycosylated N becomes D upon the action of PNGaseF. Thus N/D81 is probably not involved in mAb binding. Therefore the epitope signal seems to arise from residues within the region 82-88 CSEDLLC (SEQ ID NO: 117).

Epitope signal for mAb A1 was also observed in the C-terminal region of hCD30L (table 8) in six different peptides covering the region F211 to S226. Based on the level of exchange protection observed, all parts of the region seem to be involved in binding or affected by the binding of mAb A to a smaller or larger extent. Regions bound by the antibody are marked by bold font in Table 8.

In conclusion, the regions of hCD30L involved in binding mAb A is detected as region 82-88 CSEDLLC (SEQ ID NO: 117) and region 211-226 FQYIDTSTFPLENVLS(SEQ ID NO: 77).

Epitope Mapping of mAb B, C, D, E and F

The epitopes of mAb B, C, D, E and F were mapped using FLAG-hCD30L-EC treated with PNGaseF before HX-MS experiments. The epitope results of these studies were highly similar to mAb A (table 8) also with respect to the magnitude of the exchange protection Epitope mapping on mAb E was performed two times while A, B, C and D were mapped once each.

TABLE 8

HXMS analysis of human hCD30L yielding epitope information for antibody molecules A-F

| hCD30L peptide | | | Antibody | | | | | |
|---|---|---|---|---|---|---|---|---|
| Start | End | Sequence | A1 | B | C | D | E | F |
| 45 | 65 | DYKDDDDKHHHHHHENLYFQG (SEQ ID NO: 76) | N | N | N | N | N | N |
| 45 | 81 | DYKDDDDKHHHHHHENLYFQGDSIPNSPDNVPLKGGD (SEQ ID NO: 78) | N | na | na | na | N | na |
| 45 | 84 | DYKDDDDKHHHHHHENLYFQGDSIPNSPDNVPLKGGDCSE (SEQ ID NO: 79) | EX | EX | na | EX | EX | EX |
| 45 | 86 | DYKDDDDKHHHHHHENLYFQGDSIPNSPDNVPLKGGDCSEDL (SEQ ID NO: 80) | EX | EX | na | EX | EX | EX |
| 45 | 87 | DYKDDDDKHHHHHHENLYFQGDSIPNSPDNVPLKGGDCSEDLL (SEQ ID NO: 81) | EX | EX | na | EX | EX | EX |
| 62 | 81 | YFQGDSIPNSPDNVPLKGGD (SEQ ID NO: 82) | N | W | W | N | N | W |
| 62 | 84 | YFQGDSIPNSPDNVPLKGGDCSE (SEQ ID NO: 83) | W | W | W | W | W | W |
| 62 | 85 | YFQGDSIPNSPDNVPLKGGDCSED (SEQ ID NO: 84) | na | W | na | na | na | W |
| 62 | 86 | YFQGDSIPNSPDNVPLKGGDCSEDL (SEQ ID NO: 85) | EX | EX | EX | EX | EX | EX |
| 62 | 87 | YFQGDSIPNSPDNVPLKGGDCSEDLL (SEQ ID NO: 86) | EX | EX | EX | EX | EX | EX |
| 62 | 88 | YFQGDSIPNSPDNVPLKGGDCSEDLLC (SEQ ID NO: 87) | EX | EX | EX | EX | EX | EX |
| 66 | 81 | DSIPNSPDNVPLKGGD (SEQ ID NO: 88) | N | na | na | N | N | na |
| 66 | 86 | DSIPNSPDNVPLKGGDCSEDL (SEQ ID NO: 89) | W | W | W | W | W | W |
| 66 | 87 | DSIPNSPDNVPLKGGDCSEDLL (SEQ ID NO: 90) | EX | EX | EX | EX | EX | EX |
| 87 | 102 | LCILKRAPFKKSWAYL (SEQ ID NO: 91) | N | N | N | N | N | N |
| 88 | 102 | CILKRAPFKKSWAYL (SEQ ID NO: 92) | N | N | N | N | N | N |
| 89 | 102 | ILKRAPFKKSWAYL (SEQ ID NO: 93) | N | N | N | N | N | N |
| 91 | 102 | KRAPFKKSWAYL (SEQ ID NO: 94) | N | N | N | N | N | N |

TABLE 8-continued

HXMS analysis of human hCD30L yielding epitope information for antibody molecules A-F

| hCD3OL peptide | | | Antibody | | | | | |
|---|---|---|---|---|---|---|---|---|
| Start | End | Sequence | A1 | B | C | D | E | F |
| 103 | 131 | QVAKHLDKTKLSWNKDGILHGVRYQDGNL (SEQ ID NO: 95) | N | N | N | N | N | N |
| 105 | 131 | AKHLDKTKLSWNKDGILHGVRYQDGNL (SEQ ID NO: 96) | N | na | na | N | N | na |
| 114 | 121 | SWNKDGIL (SEQ ID NO: 97) | N | na | na | N | N | na |
| 114 | 129 | SWNKDGILHGVRYQDG (SEQ ID NO: 98) | na | N | N | na | na | N |
| 114 | 131 | SWNKDGILHGVRYQDGNL (SEQ ID NO: 99) | N | N | N | N | N | N |
| 132 | 138 | VIQFPGL (SEQ ID NO: 100) | N | N | N | N | N | N |
| 132 | 139 | VIQFPGLY (SEQ ID NO: 101) | N | N | N | N | N | N |
| 132 | 140 | VIQFPGLYF (SEQ ID NO: 102) | N | N | N | N | N | N |
| 148 | 157 | LVQCPQNSVD (SEQ ID NO: 103) | N | N | N | N | N | N |
| 158 | 162 | LKLEL (SEQ ID NO: 104) | N | N | N | N | N | N |
| 163 | 173 | LINKHIKKQAL (SEQ ID NO: 105) | N | N | N | N | N | N |
| 163 | 175 | LINKHIKKQALVT (SEQ ID NO: 106) | N | N | N | N | N | N |
| 174 | 190 | VTVCESGMQTKHVYQNL (SEQ ID NO: 107) | N | N | N | N | N | N |
| 174 | 192 | VTVCESGMQTKHVYQNLSQ (SEQ ID NO: 108) | N | N | N | N | N | N |
| 174 | 193 | VTVCESGMQTKHVYQNLSQF (SEQ ID NO: 109) | N | N | N | N | N | N |
| 176 | 190 | VCESGMQTKHVYQNL (SEQ ID NO: 110) | N | na | na | N | N | na |
| 211 | 222 | FQYIDTSTFPLE (SEQ ID NO: 111) | EX | EX | EX | EX | EX | EX |
| 211 | 225 | FQYIDTSTFPLENVL (SEQ ID NO: 112) | EX | na | na | na | EX | na |
| 213 | 222 | YIDTSTFPLE (SEQ ID NO: 113) | EX | EX | EX | EX | EX | EX |
| 213 | 225 | YIDTSTFPLENVL (SEQ ID NO: 114) | EX | EX | EX | EX | EX | EX |
| 213 | 226 | YIDTSTFPLENVLS (SEQ ID NO: 115) | EX | EX | na | na | EX | EX |
| 217 | 225 | STFPLENVL (SEQ ID NO: 116) | W | W | W | W | W | W |

EX: exchange protection upon antibody binding indicating epitope region (>0.4 Da on at least three-points)
W: Weak exchange protection upon antibody binding (0.2-0.4 Da on at least three time-points).
N: No exchange protection upon antibody binding (<0.2 Da).
na: Not analyzable in respective experiment.

In conclusion, the regions of hCD30L involved in binding mAb B, C, D, E and F is similar to to the regions involved in binding of mAb A1 and is detected as region 82-88 CSEDLLC (SEQ ID NO: 117) and region 211-226 FQYIDTSTFPLENVLS (SEQ ID NO: 77).

Example 7

Binning of CD30 L Antibodies Using an Immobilize Anti-CD30L A-F$_{AB}$

Anti-human CD30L monoclonal antibodies were epitope binned on a Biacore T200 (GE Healthcare 28-9750-01) using a classical sandwich approach.

To reduce steric hindrance the immobilized antibody was used in a monovalent format. To determine if the antigen binding region of the anti-hCD30L antibodies bound overlapping epitopes the ability of the antibodies A-F to bind CD30L already bound by the Fab of antibody A1 was tested.

Fab fragments may be obtained by digesting whole antibodies with papain which cleaves up-stream of the cysteines of the hinge region or by recombinant expression of the heavy and light chain variable regions. The Fab fragment of Anti-hCD30L A1 (A1-F$_{AB}$) was prepared using immobilized papain in the presence of cysteine to enzymatically cleave the whole IgG right above the hinge region creating two Fab fragments and one Fc fragment per antibody molecule. The Fab was separated from the Fc using Protein A affinity chromatography and then buffer exchanged into PBS. The procedure was performed according to manufactures instructions (Pierce Fab Preparation Kit #44985, US).

The anti-human CD30L $F_{AB}$ (Fab of antibody A1) was immobilized and human CD30L-His$_{10}$ trimer (R&D Systems 1028-CL) captured hereon. Subsequently soluble anti-hCD30L A-F was injected. Binding of the second antibody implies that the two antibodies are in different epitope bins.

Anti-hCD30L A1-$F_{AB}$ was diluted to 40 µg/mL in 10 mM acetate buffer, pH 5.0 and amine coupled to a CM5 chip (GE healthcare BR-1000-12, BR-1000-50) to a level of 3566 RU, using standard procedures. Human CD30L-His$_{10}$ trimer (R&D Systems 1028-CL) was diluted to 10 nM in HBS-P+ (GE healthcare BR-1006-71) and injected over the A-$F_{AB}$ surface to capture 175 RU of CD30L. The second antibody was injected at 75 nM over the captured hCD30L. Controls included null capture (buffer only) and injections of buffer instead of soluble antibody. All experiments were performed at 25° C.

Coating of hCD30L with A-FAB blocked binding of a sub-group of the antibodies A-F. The controls using A-Fab and A where both blocked as expected. In addition also antibodies F and B were prevented from binding to the captured hCD30L, whereas the antibodies E, C and D were capable of binding to hCD30L demonstrating that there binding epitope can be distinguished from the binding epitope of A, B and F. In conclusion the antibodies A, F and B competes with the Fab of antibody A1 for binding to hCD30L.

What is claimed is:

1. An isolated antibody that binds CD30L, comprising:
 a) CDRH1, CDRH2 and CDRH3 identified by SEQ ID NOs: 14, 19, 25, and CDRL1, CDRL2 and CDRL3 identified by SEQ ID NO: 1, 7 and 11;
 b) CDRH1, CDRH2 and CDRH3 identified by SEQ ID NOs: 15, 21, 26, and CDRL1, CDRL2 and CDRL3 identified by SEQ ID NO: 2, 8 and 12;
 c) CDRH1, CDRH2 and CDRH3 identified by SEQ ID NOs: 15, 21, 26, and CDRL1, CDRL2 and CDRL3 identified by SEQ ID NO: 3, 8 and 12;
 d) CDRH1, CDRH2 and CDRH3 identified by SEQ ID NOs: 16, 22, 27, and CDRL1, CDRL2 and CDRL3 identified by SEQ ID NO: 4, 9 and 12;
 e) CDRH1, CDRH2 and CDRH3 identified by SEQ ID NOs: 17, 23, 28, and CDRL1, CDRL2 and CDRL3 identified by SEQ ID NO: 5, 8 and 13; or
 f) CDRH1, CDRH2 and CDRH3 identified by SEQ ID NOs: 18, 24, 29, and CDRL1, CDRL2 and CDRL3 identified by SEQ ID NO: 6, 10 and 12.

2. An isolated antibody that binds CD30L selected from a group consisting of:
 a) an isolated antibody comprising a heavy chain variable region selected from the group consisting of SEQ ID NOs:48, 50, 52, 54, 56, 58, 60 and 62, and a light chain variable region of SEQ ID NO: 36;
 b) an isolated antibody comprising a heavy chain variable region of SEQ ID NO:64 and a light chain variable region of SEQ ID NO:38;
 c) an isolated antibody comprising a heavy chain variable region of SEQ ID NO:66 and a light chain variable region of SEQ ID NO:40;
 d) an isolated antibody comprising a heavy chain variable region of SEQ ID NO:68 and a light chain variable region of SEQ ID NO:42;
 e) an isolated antibody comprising a heavy chain variable region of SEQ ID NO:70 and a light chain variable region of SEQ ID NO:44; and
 f) an isolated antibody comprising a heavy chain variable region of SEQ ID NO:72 and a light chain variable region of SEQ ID NO:46.

3. The isolated antibody of claim 1, wherein said antibody is of the IgG1-, IgG2-, IgG3 or IgG4-type.

4. A pharmaceutical composition comprising at least one antibody of claim 1 and a pharmaceutically acceptable excipient.

5. The isolated antibody of claim 1, wherein CDRH1, CDRH2 and CDRH3 are identified by SEQ ID NOs: 14, 19, 25, respectively, and CDRL1, CDRL2 and CDRL3 are identified by SEQ ID NO: 1, 7 and 11, respectively.

6. The isolated antibody of claim 1, comprising a heavy chain variable region of SEQ ID NO: 48 and a light chain variable region of SEQ ID NO: 36.

* * * * *

SEQUENCE LISTING

```
<160> NUMBER OF SEQ ID NOS: 117

<210> SEQ ID NO 1
<211> LENGTH: 14
<212> TYPE: PRT
<213> ORGANISM: Homo sapiens

<400> SEQUENCE: 1

Thr Gly Thr Ser Ser Asp Val Gly Val Tyr Asp Tyr Val Ser
1               5                   10

<210> SEQ ID NO 2
<211> LENGTH: 14
<212> TYPE: PRT
<213> ORGANISM: Homo sapiens

<400> SEQUENCE: 2

Thr Gly Thr Ser Ser Asp Val Gly Leu Tyr Asn Tyr Val Ser
1               5                   10

<210> SEQ ID NO 3
<211> LENGTH: 14
<212> TYPE: PRT
<213> ORGANISM: Homo sapiens

<400> SEQUENCE: 3

Thr Gly Thr Ser Ser Asp Ile Gly Leu Tyr Asp Tyr Val Ser
1               5                   10

<210> SEQ ID NO 4
<211> LENGTH: 14
<212> TYPE: PRT
<213> ORGANISM: Homo sapiens

<400> SEQUENCE: 4

Thr Gly Thr Ser Ser Asp Ile Gly Leu Tyr Asn Tyr Val Ser
1               5                   10

<210> SEQ ID NO 5
<211> LENGTH: 14
<212> TYPE: PRT
<213> ORGANISM: Homo sapiens

<400> SEQUENCE: 5

Thr Gly Ser Ser Ser Asp Ile Gly Thr Tyr Asn Tyr Val Ser
1               5                   10
```

<210> SEQ ID NO 6
<211> LENGTH: 14
<212> TYPE: PRT
<213> ORGANISM: Homo sapiens

<400> SEQUENCE: 6

Thr Gly Thr Ser Ser Asp Val Gly Leu Tyr Asn Tyr Val Ser
1               5                   10

<210> SEQ ID NO 7
<211> LENGTH: 7
<212> TYPE: PRT
<213> ORGANISM: Homo sapiens

<400> SEQUENCE: 7

Glu Val Ser Asn Arg Pro Ser
1               5

<210> SEQ ID NO 8
<211> LENGTH: 7
<212> TYPE: PRT
<213> ORGANISM: Homo sapiens

<400> SEQUENCE: 8

Glu Val Asn Asn Arg Pro Ser
1               5

<210> SEQ ID NO 9
<211> LENGTH: 7
<212> TYPE: PRT
<213> ORGANISM: Homo sapiens

<400> SEQUENCE: 9

Glu Val Ile Asn Arg Pro Ser
1               5

<210> SEQ ID NO 10
<211> LENGTH: 7
<212> TYPE: PRT
<213> ORGANISM: Homo sapiens

<400> SEQUENCE: 10

Glu Val Ser Lys Arg Pro Ser
1               5

<210> SEQ ID NO 11
<211> LENGTH: 10
<212> TYPE: PRT
<213> ORGANISM: Homo sapiens

<400> SEQUENCE: 11

Ser Ser Tyr Thr Ser Arg Ser Thr Trp Val
1               5                   10

<210> SEQ ID NO 12
<211> LENGTH: 10
<212> TYPE: PRT
<213> ORGANISM: Homo sapiens

<400> SEQUENCE: 12

Ser Ser Tyr Thr Ser Ser Ser Thr Trp Val
1               5                   10

<210> SEQ ID NO 13
<211> LENGTH: 10

```
<212> TYPE: PRT
<213> ORGANISM: Homo sapiens

<400> SEQUENCE: 13

Ser Ser Tyr Ser Ser Ser Ser Thr Trp Val
1               5                   10

<210> SEQ ID NO 14
<211> LENGTH: 5
<212> TYPE: PRT
<213> ORGANISM: Homo sapiens

<400> SEQUENCE: 14

Ser Tyr Ile Trp Ser
1               5

<210> SEQ ID NO 15
<211> LENGTH: 5
<212> TYPE: PRT
<213> ORGANISM: Homo sapiens

<400> SEQUENCE: 15

Ser Tyr Tyr Trp Thr
1               5

<210> SEQ ID NO 16
<211> LENGTH: 5
<212> TYPE: PRT
<213> ORGANISM: Homo sapiens

<400> SEQUENCE: 16

Ser Tyr Ser Trp Ser
1               5

<210> SEQ ID NO 17
<211> LENGTH: 5
<212> TYPE: PRT
<213> ORGANISM: Homo sapiens

<400> SEQUENCE: 17

Asn Asn Tyr Trp Ser
1               5

<210> SEQ ID NO 18
<211> LENGTH: 5
<212> TYPE: PRT
<213> ORGANISM: Homo sapiens

<400> SEQUENCE: 18

Ser Tyr Tyr Trp Ser
1               5

<210> SEQ ID NO 19
<211> LENGTH: 16
<212> TYPE: PRT
<213> ORGANISM: Homo sapiens

<400> SEQUENCE: 19

Arg Ile Tyr Ala Ser Gly Asn Thr Asn Tyr Asn Pro Ser Leu Lys Ser
1               5                   10                  15

<210> SEQ ID NO 20
<211> LENGTH: 16
<212> TYPE: PRT
<213> ORGANISM: Homo sapiens
```

<400> SEQUENCE: 20

Arg Ile Tyr Ala Ser Gly Gln Thr Asn Tyr Asn Pro Ser Leu Lys Ser
1               5                   10                  15

<210> SEQ ID NO 21
<211> LENGTH: 16
<212> TYPE: PRT
<213> ORGANISM: Homo sapiens

<400> SEQUENCE: 21

Arg Ile Tyr Thr Ser Gly Ile Thr Asn Tyr Asn Pro Ser Leu Lys Ser
1               5                   10                  15

<210> SEQ ID NO 22
<211> LENGTH: 16
<212> TYPE: PRT
<213> ORGANISM: Homo sapiens

<400> SEQUENCE: 22

Arg Thr Ser Thr Ser Gly Arg Asn Asn Tyr Asn Pro Ser Leu Lys Ser
1               5                   10                  15

<210> SEQ ID NO 23
<211> LENGTH: 16
<212> TYPE: PRT
<213> ORGANISM: Homo sapiens

<400> SEQUENCE: 23

Arg Val Tyr Ser Ser Gly Leu Thr Asn Tyr Lys Pro Ser Leu Lys Ser
1               5                   10                  15

<210> SEQ ID NO 24
<211> LENGTH: 16
<212> TYPE: PRT
<213> ORGANISM: Homo sapiens

<400> SEQUENCE: 24

Arg Ile Phe Ala Ser Gly Ser Thr Asn Tyr Asn Pro Ser Leu Arg Ser
1               5                   10                  15

<210> SEQ ID NO 25
<211> LENGTH: 16
<212> TYPE: PRT
<213> ORGANISM: Homo sapiens

<400> SEQUENCE: 25

Asp Tyr Arg Val Ala Gly Thr Tyr Tyr Tyr Tyr Gly Leu Asp Val
1               5                   10                  15

<210> SEQ ID NO 26
<211> LENGTH: 16
<212> TYPE: PRT
<213> ORGANISM: Homo sapiens

<400> SEQUENCE: 26

Glu Arg Val Val Gly Ala Ser Arg Tyr Tyr Tyr Gly Val Asp Val
1               5                   10                  15

<210> SEQ ID NO 27
<211> LENGTH: 16
<212> TYPE: PRT
<213> ORGANISM: Homo sapiens

<400> SEQUENCE: 27

```
Asp Phe Thr Ile Ala Ala Arg Arg Tyr Tyr Tyr Gly Met Asp Val
1               5                   10                  15

<210> SEQ ID NO 28
<211> LENGTH: 16
<212> TYPE: PRT
<213> ORGANISM: Homo sapiens

<400> SEQUENCE: 28

Glu Arg Ala Thr Val Thr Thr Arg Tyr His Tyr Asp Gly Met Asp Val
1               5                   10                  15

<210> SEQ ID NO 29
<211> LENGTH: 16
<212> TYPE: PRT
<213> ORGANISM: Homo sapiens

<400> SEQUENCE: 29

Glu Arg Val Gly Val Gln Asp Tyr Tyr His Tyr Ser Gly Met Asp Val
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (7)..(7)
<223> OTHER INFORMATION: Val or Ile
<220> FEATURE:
<221> NAME/KEY: MOD_RES
<222> LOCATION: (9)..(9)
<223> OTHER INFORMATION: Val, Thr or Leu
<220> FEATURE:
<221> NAME/KEY: MOD_RES
<222> LOCATION: (11)..(11)
<223> OTHER INFORMATION: Asp or Asn

<400> SEQUENCE: 30

Thr Gly Xaa Ser Ser Asp Xaa Gly Xaa Tyr Xaa Tyr Val Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Asn or Ile
<220> FEATURE:
<221> NAME/KEY: MOD_RES
<222> LOCATION: (4)..(4)
<223> OTHER INFORMATION: Asn or Lys

<400> SEQUENCE: 31

Glu Val Xaa Xaa Arg Pro Ser
1               5
```

-continued

```
<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (6)..(6)
<223> OTHER INFORMATION: Arg or Ser

<400> SEQUENCE: 32

Ser Ser Tyr Xaa Ser Xaa Ser Thr Trp Val
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (2)..(2)
<223> OTHER INFORMATION: Tyr or Asn
<220> FEATURE:
<221> NAME/KEY: MOD_RES
<222> LOCATION: (3)..(3)
<223> OTHER INFORMATION: Ile, Tyr or Ser
<220> FEATURE:
<221> NAME/KEY: MOD_RES
<222> LOCATION: (5)..(5)
<223> OTHER INFORMATION: Thr or Ser

<400> SEQUENCE: 33

Xaa Xaa Xaa Trp Xaa
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Thr
<220> FEATURE:
<221> NAME/KEY: MOD_RES
<222> LOCATION: (3)..(3)
<223> OTHER INFORMATION: Tyr, Phe or Ser
<220> FEATURE:
<221> NAME/KEY: MOD_RES
<222> LOCATION: (4)..(4)
<223> OTHER INFORMATION: Thr, Ser or Ala
<220> FEATURE:
<221> NAME/KEY: MOD_RES
<222> LOCATION: (7)..(7)
<223> OTHER INFORMATION: Ile, Leu, Asn, Ser, Arg or Gln
<220> FEATURE:
<221> NAME/KEY: MOD_RES
<222> LOCATION: (8)..(8)
<223> OTHER INFORMATION: Thr or Asn
```

```
<220> FEATURE:
<221> NAME/KEY: MOD_RES
<222> LOCATION: (11)..(11)
<223> OTHER INFORMATION: Asn or Lys
<220> FEATURE:
<221> NAME/KEY: MOD_RES
<222> LOCATION: (15)..(15)
<223> OTHER INFORMATION: Lys or Arg

<400> SEQUENCE: 34

Arg Xaa Xaa Xaa Ser Gly Xaa Xaa Asn Tyr Xaa Pro Ser Leu Xaa Ser
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Arg, Thr or Phe
<220> FEATURE:
<221> NAME/KEY: MOD_RES
<222> LOCATION: (3)..(3)
<223> OTHER INFORMATION: Val, Ala, Arg or Thr
<220> FEATURE:
<221> NAME/KEY: MOD_RES
<222> LOCATION: (4)..(4)
<223> OTHER INFORMATION: Val, Thr, Gly or Ile
<220> FEATURE:
<221> NAME/KEY: MOD_RES
<222> LOCATION: (5)..(5)
<223> OTHER INFORMATION: Val, Ala or Gly
<220> FEATURE:
<221> NAME/KEY: MOD_RES
<222> LOCATION: (6)..(6)
<223> OTHER INFORMATION: Ala, Thr, Gly or Gln
<220> FEATURE:
<221> NAME/KEY: MOD_RES
<222> LOCATION: (7)..(7)
<223> OTHER INFORMATION: Thr, Asp, Arg or Ser
<220> FEATURE:
<221> NAME/KEY: MOD_RES
<222> LOCATION: (8)..(8)
<223> OTHER INFORMATION: Arg or Tyr
<220> FEATURE:
<221> NAME/KEY: MOD_RES
<222> LOCATION: (10)..(10)
<223> OTHER INFORMATION: Thr or His
<220> FEATURE:
<221> NAME/KEY: MOD_RES
<222> LOCATION: (12)..(12)
<223> OTHER INFORMATION: Thr, Asp or Ser
<220> FEATURE:
<221> NAME/KEY: MOD_RES
<222> LOCATION: (14)..(14)
<223> OTHER INFORMATION: Met, Leu or Val

<400> SEQUENCE: 35

Xaa Xaa Xaa Xaa Xaa Xaa Xaa Xaa Tyr Xaa Tyr Xaa Gly Xaa Asp Val
1               5                   10                  15

<210> SEQ ID NO 36
<211> LENGTH: 110
<212> TYPE: PRT
<213> ORGANISM: Homo sapiens

<400> SEQUENCE: 36
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Val Tyr
            20                  25                  30

Asp Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Thr Glu Asp Glu Ala Asp Tyr Tyr Cys Ser Ser Tyr Thr Ser Arg
                85                  90                  95

Ser Thr Trp Val Phe Gly Gly Gly Thr Lys Leu Thr Val Leu
            100                 105                 110

<210> SEQ ID NO 37
<211> LENGTH: 326
<212> TYPE: DNA
<213> ORGANISM: Homo sapiens

<400> SEQUENCE: 37
cagtctgccc tgactcagcc tgcctccgtg tctgggtctc ctggacagtc gatcaccatc      60
tcctgcactg gaaccagcag tgacgttggt gtttatgact atgtctcctg gtatcaacag     120
cacccaggca agcccccaa actcatgatt tatgaggtca gtaatcggcc ctcaggggtt     180
tctaatcgct tctctggctc caagtctggc aacacggcct ccctgaccat ctctgggctc    240
caaactgagg acgaggctga ttattactgc agctcatata caagcaggag cacttgggtg    300
ttcggcggag ggaccaagct gaccgt                                          326

<210> SEQ ID NO 38
<211> LENGTH: 110
<212> TYPE: PRT
<213> ORGANISM: Homo sapiens

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln His Pro Asp Lys Ala Pro Lys Leu
        35                  40                  45

Met Ile Phe Glu Val Asn Asn Arg Pro Ser Gly Val Ser Asn Arg Phe
    50                  55                  60

Ser Gly Ser Asn Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 39
<211> LENGTH: 330
<212> TYPE: DNA
<213> ORGANISM: Homo sapiens

<400> SEQUENCE: 39

```
cagtctgccc tgactcagcc tgcctccgtg tctgggtctc ctggacagtc gatcaccatc    60
tcctgcactg gaaccagcag tgacgttggt ctttataact atgtctcctg gtaccaacag   120
cacccagaca aagcccccaa actcatgatt tttgaggtca ataatcggcc ctcaggggtt   180
tctaatcgct tctctggctc caactctggc aacacggcct ccctgaccat ctctgggctc   240
caggctgagg acgaggctga ttattactgc agctcatata caagcagcag cacttgggtg   300
ttcggcggag ggaccaagtt gaccgtccta                                    330
```

<210> SEQ ID NO 40
<211> LENGTH: 110
<212> TYPE: PRT
<213> ORGANISM: Homo sapiens

<400> SEQUENCE: 40

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asp Tyr Val Ser Trp Tyr Gln Gln His Pro Asp Arg Ala Pro Lys Leu
        35                  40                  45

Ile Ile Phe Glu Val Asn Asn Arg Pro Ser Gly Val Ser Tyr Arg Phe
    50                  55                  60

Ser Gly Ser Asn Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 41
<211> LENGTH: 326
<212> TYPE: DNA
<213> ORGANISM: Homo sapiens

<400> SEQUENCE: 41

```
cagtctgccc tgactcagcc tgcctccgtg tctgggtctc ctggacagtc gatcaccatc    60
tcctgcactg gaaccagcag tgacattggt ctttatgact atgtctcctg gtaccaacag   120
cacccagaca gagcccccaa actcataatt tttgaggtca ataatcggcc ctcaggggtt   180
tcttatcgct tctctggctc caactctggc aacacggcct ccctgaccat ctctgggctc   240
caggctgagg acgaggctga ttattactgc agctcatata caagcagcag cacttgggtg   300
ttcggcggag ggaccaagtt gaccgt                                        326
```

<210> SEQ ID NO 42
<211> LENGTH: 110
<212> TYPE: PRT
<213> ORGANISM: Homo sapiens

<400> SEQUENCE: 42

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asn Tyr Val Ser Trp Tyr Gln Gln His Pro Gly Lys Ala Pro Lys Leu
        35                  40                  45

Ile Ile Tyr Glu Val Ile Asn Arg Pro Ser Gly Val Ser Asn Arg Phe
```

```
                50                   55                   60
Ser Gly Ser Glu Ser Gly Asn Thr Ala Ser Leu Thr Ile Ser Gly Leu
 65                  70                  75                  80

Gln Ala Glu Asp Glu Ala Asn Tyr Tyr Cys Ser Ser Tyr Thr Ser Ser
                 85                  90                  95

Ser Thr Trp Val Phe Gly Gly Gly Thr Lys Leu Thr Val Leu
            100                 105                 110

<210> SEQ ID NO 43
<211> LENGTH: 330
<212> TYPE: DNA
<213> ORGANISM: Homo sapiens

<400> SEQUENCE: 43
cagtctgccc tgactcagcc tgcctccgtg tctgggtctc ctggacagtc gatcaccatc      60
tcctgcactg gaaccagcag tgacattggt ctttataact atgtctcctg gtaccaacag     120
cacccaggca aagcccccaa actcataatt tatgaggtca ttaatcggcc ctcaggggtt     180
tctaatcgct tctctggctc cgagtctggc aacacggcct ccctgaccat ctctggactc     240
caggctgagg acgaggctaa ttattactgc agttcatata caagcagcag cacttgggtg     300
ttcggcggag ggaccaagct gaccgtcctg                                      330

<210> SEQ ID NO 44
<211> LENGTH: 110
<212> TYPE: PRT
<213> ORGANISM: Homo sapiens

<400> SEQUENCE: 44

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Ile Gly Thr Tyr
                20                  25                  30

Asn Tyr Val Ser Trp Tyr Gln Gln Tyr Pro Gly Lys Ala Pro Glu Leu
             35                  40                  45

Met Ile Tyr Glu Val Asn Asn Arg Pro Ser Gly Val Ser Asp Arg Phe
 50                  55                  60

Ser Gly Ser Thr Ser Gly Asn Thr Ala Ser Leu Thr Ile Ser Gly Leu
 65                  70                  75                  80

Gln Ala Asn Asp Glu Ala Asp Tyr Tyr Cys Ser Ser Tyr Ser Ser Ser
                 85                  90                  95

Ser Thr Trp Val Phe Gly Gly Gly Thr Lys Leu Thr Val Leu
            100                 105                 110

<210> SEQ ID NO 45
<211> LENGTH: 326
<212> TYPE: DNA
<213> ORGANISM: Homo sapiens

<400> SEQUENCE: 45
cagtctgccc tgactcagcc tgcctccgtg tctgggtctc ctggacagtc gatcaccatc      60
tcctgcactg gaagcagcag tgacattggt acttataact atgtctcctg gtaccaacag     120
tacccaggca aagcccccga actcatgatt tatgaggtca ataatcggcc ctcaggggtt     180
tctgatcgct tctctggctc cacgtctggc aatacggcct ccctgaccat ctctgggctc     240
caggctaacg acgaggctga ttattactgc agctcatatt caagcagcag cacttgggtg     300
ttcggcggag ggactaagct gaccgt                                          326
```

<210> SEQ ID NO 46
<211> LENGTH: 110
<212> TYPE: PRT
<213> ORGANISM: Homo sapiens

<400> SEQUENCE: 46

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Thr Ser Gly Asn Thr Ala Ser Leu Thr Ile Ser Gly Leu
65                  70                  75                  80

Gln Ala Asp Asp Glu Ala Asp Tyr Ser Cys Ser Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 47
<211> LENGTH: 322
<212> TYPE: DNA
<213> ORGANISM: Homo sapiens

<400> SEQUENCE: 47

```
cagtctgccc tgactcagcc tgcctccgtg tctgggtctc ctggacagtc gatcaccatc    60
tcctgcactg gaactagcag tgacgttggt ctttataact atgtctcctg gtaccaacag   120
cagccaggca agccccccaa actcatgatt tatgaggtca gtaagcggcc ctcaggagtt   180
tctaatcgct tctctggctc cacgtctggc aacacggcct ccctgaccat ctctgggctc   240
caggctgacg acgaggctga ttattcctgc agctcatata caagcagcag cacttgggtc   300
ttcggcggag ggaccaagct ga                                           322
```

<210> SEQ ID NO 48
<211> LENGTH: 124
<212> TYPE: PRT
<213> ORGANISM: Homo sapiens

<400> SEQUENCE: 48

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Tyr Tyr Tyr Tyr Tyr Gly Leu Asp
            100                 105                 110
```

```
Val Trp Gly Gln Gly Thr Thr Val Thr Val Ser Ser
        115                 120
```

<210> SEQ ID NO 49
<211> LENGTH: 372
<212> TYPE: DNA
<213> ORGANISM: Homo sapiens

<400> SEQUENCE: 49

```
caggtgcagc tgcaggagtc gggcccagga ctggtgaagc cttcggagac cctgtccctc    60
acctgcactg tctctggtgg ctccatcagt agttacatct ggagctggat ccggcagccc   120
gccggaaagg gactggagtg gattgggcgt atctatgcca gtgggaacac caactacaac   180
ccctccctca gagtcgagt caccatatca gtagacacgt ccaagaacca gttctccctg   240
aagctgagct ctatgaccgc cgcggacacg gccgtatatt actgtgcgag agattatagg   300
gtggctggca cttactacta ctactacggt ttggacgtct ggggccaagg gaccacggtc   360
accgtctcct ca                                                        372
```

<210> SEQ ID NO 50
<211> LENGTH: 124
<212> TYPE: PRT
<213> ORGANISM: Homo sapiens

<400> SEQUENCE: 50

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 51
<211> LENGTH: 372
<212> TYPE: DNA
<213> ORGANISM: Homo sapiens

<400> SEQUENCE: 51

```
caggtgcagc tgcaggagtc gggcccagga ctggtgaagc cttcggagac cctgtccctc    60
acctgcactg tctctggtgg ctccatcagt agttacatct ggagctggat ccggcagccc   120
gccggaaagg gactggagtg gattgggcgt atctatgcca gtgggaacac caactacaac   180
ccctccctca gagtcgagt caccatgtca gtagacacgt ccaagaacca gttctccctg   240
aagctgagct ctatgaccgc cgcggacacg gccgtatatt actgtgcgag agattatagg   300
gtggctggca cttactacta ctactacggt ttggacgtct ggggccaagg gaccacggtc   360
accgtctcct ca                                                        372
```

<210> SEQ ID NO 52
<211> LENGTH: 124
<212> TYPE: PRT
<213> ORGANISM: Homo sapiens

<400> SEQUENCE: 52

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
            115                 120
```

<210> SEQ ID NO 53
<211> LENGTH: 372
<212> TYPE: DNA
<213> ORGANISM: Homo sapiens

<400> SEQUENCE: 53

```
caggtgcagc tgcaggagtc gggcccagga ctggtgaagc cttcggagac cctgtccctc    60
acctgcactg tctctggtgg ctccatcagt agttacatct ggagctggat ccggcagccc   120
gccggaaagg gactggagtg gattgggcgt atctatgcca gtgggaacac caactacaac   180
ccctccctca agagtcgagt caccatgtca gtagacacgt ccaagaacca gttctccctg   240
aagctgagct ctgtaaccgc cgcggacacg gccgtatatt actgtgcgag agattatagg   300
gtggctggca cttactacta ctactacggt ttggacgtct ggggccaagg gaccacggtc   360
accgtctcct ca                                                       372
```

<210> SEQ ID NO 54
<211> LENGTH: 124
<212> TYPE: PRT
<213> ORGANISM: Homo sapiens

<400> SEQUENCE: 54

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95
```

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
            115                 120

<210> SEQ ID NO 55
<211> LENGTH: 366
<212> TYPE: DNA
<213> ORGANISM: Homo sapiens

<400> SEQUENCE: 55
cagctgcagg agtcgggccc aggactggtg aagccttcgg agaccctgtc cctcacctgc    60
actgtctctg gtggctccat cagtagttac atctggagct ggatccggca gcccgccgga   120
aagggactgg agtggattgg gcgtatctat gccagtgggc aaaccaacta caaccccctcc  180 ctcaagagtc gagtcaccat gtcagtagac acgtccaaga accagttctc cctgaagctg   240
agctctatga ccgccgcgga cacggccgta tattactgtg cgagagatta tagggtggct   300
ggcacttact actactacta cggtttggac gtctggggcc aagggaccac ggtcaccgtc   360
tcctca                                                              366

<210> SEQ ID NO 56
<211> LENGTH: 124
<212> TYPE: PRT
<213> ORGANISM: Homo sapiens

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
            115                 120

<210> SEQ ID NO 57
<211> LENGTH: 366
<212> TYPE: DNA
<213> ORGANISM: Homo sapiens

<400> SEQUENCE: 57
cagctgcagg agtcgggccc aggactggtg aagccttcgg agaccctgtc cctcacctgc    60
actgtctctg gtggctccat cagtagttac atctggagct ggatccggca gcccgccgga   120
aagggactgg agtggattgg gcgtatctat gccagtgggc aaaccaacta caaccccctcc  180 ctcaagagtc gagtcaccat atcagtagac acgtccaaga accagttctc cctgaagctg   240
agctctgtaa ccgccgcgga cacggccgta tattactgtg cgagagatta tagggtggct   300

```
ggcacttact actactacta cggtttggac gtctggggcc aagggaccac ggtcaccgtc      360
tcctca                                                                 366
```

<210> SEQ ID NO 58
<211> LENGTH: 124
<212> TYPE: PRT
<213> ORGANISM: Homo sapiens

<400> SEQUENCE: 58

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 59
<211> LENGTH: 372
<212> TYPE: DNA
<213> ORGANISM: Homo sapiens

<400> SEQUENCE: 59

```
caggtgcagc tgcaggagtc gggcccagga ctggtgaagc cttcggagac cctgtccctc      60
acctgcactg tctctggtgg ctccatcagt agttacatct ggagctggat ccggcagccc     120
gccggaaagg gactggagtg gattgggcgt atctatgcca gtgggaacac caactacaac     180
ccctccctca agagtcgagt caccatatca gtagacacgt ccaagaacca gttctccctg     240
aagctgagct ctgtaaccgc cgcggacacg gccgtatatt actgtgcgag agattatagg     300
gtggctggca cttactacta ctactacggt ttggacgtct ggggccaagg gaccacggtc     360
accgtctcct ca                                                         372
```

<210> SEQ ID NO 60
<211> LENGTH: 124
<212> TYPE: PRT
<213> ORGANISM: Homo sapiens

<400> SEQUENCE: 60

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
```

```
                65                  70                  75                  80
Lys Leu Ser Ser Met Thr Ala Ala Asp Thr Ala Val Tyr Tyr Cys Ala
                        85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 61
<211> LENGTH: 379
<212> TYPE: DNA
<213> ORGANISM: Homo sapiens

<400> SEQUENCE: 61

```
cagatgtcag gtgcagctgc aggagtcggg cccaggactg gtgaagcctt cggagaccct      60
gtccctcacc tgcactgtct ctggtggctc catcagtagt tacatctgga gctggatccg     120
gcagcccgcc ggaaagggac tggagtggat tgggcgtatc tatgccagtg ggcaaaccaa     180
ctacaacccc tccctcaaga gtcgagtcac catatcagta gacacgtcca agaaccagtt     240
ctccctgaag ctgagctcta tgaccgccgc ggacacggcc gtatattact gtgcgagaga     300
ttataggatg gctggcactt actactacta ctacggtttg gacgtctggg gccaagggac     360
cacggtcacc gtctcctca                                                  379
```

<210> SEQ ID NO 62
<211> LENGTH: 124
<212> TYPE: PRT
<213> ORGANISM: Homo sapiens

<400> SEQUENCE: 62

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                        85                  90                  95

Arg Asp Tyr Arg Val Ala Gly Thr Tyr Tyr Tyr Tyr Gly Leu Asp
            100                 105                 110

Val Trp Gly Gln Gly Thr Thr Val Thr Val Ser Ser
        115                 120
```

<210> SEQ ID NO 63
<211> LENGTH: 379
<212> TYPE: DNA
<213> ORGANISM: Homo sapiens

<400> SEQUENCE: 63

```
cagatgtcag gtgcagctgc aggagtcggg cccaggactg gtgaagcctt cggagaccct      60
gtccctcacc tgcactgtct ctggtggctc catcagtagt tacatctgga gctggatccg     120
gcagcccgcc ggaaagggac tggagtggat tgggcgtatc tatgccagtg ggcaaaccaa     180
```

```
ctacaacccc tccctcaaga gtcgagtcac catgtcagta gacacgtcca agaaccagtt    240
ctccctgaag ctgagctctg taaccgccgc ggacacggcc gtatattact gtgcgagaga    300
ttatagggtg gctggcactt actactacta ctacggtttg gacgtctggg gccaagggac    360
cacggtcacc gtctcctca                                                 379
```

<210> SEQ ID NO 64
<211> LENGTH: 124
<212> TYPE: PRT
<213> ORGANISM: Homo sapiens

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Val Val Gly Ala Ser Arg Tyr Tyr Tyr Gly Val Asp
            100                 105                 110

Val Trp Gly Gln Gly Thr Thr Val Thr Val Ser Ser
        115                 120

<210> SEQ ID NO 65
<211> LENGTH: 372
<212> TYPE: DNA
<213> ORGANISM: Homo sapiens

<400> SEQUENCE: 65

```
caggtgcagc tgcaggagtc gggcccagga ctggtgaagc cttcggagac cctgtccctc    60
acctgcactg tctctggtgg ctccatcagt agttactact ggacctggat ccggcagccc    120
gccgggaagg gactggagtg gattggcgt atctatacca gtggaatcac caactacaat    180
ccctccctca agagtcgcgt caccatgtca gtagacacgt ccaagaacca gttctccctg    240
aagctgagct ctgtgaccgc cgcggacacg gccgtgtatt actgtgcgag agagcgggta    300
gtgggagcta gtaggtacta ctactacggt gtggacgtct ggggccaagg gaccacggtc    360
accgtctcct cc                                                        372
```

<210> SEQ ID NO 66
<211> LENGTH: 124
<212> TYPE: PRT
<213> ORGANISM: Homo sapiens

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
            50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Arg Val Val Gly Ala Ser Arg Tyr Tyr Tyr Gly Val Asp
                100                 105                 110

Val Trp Gly Gln Gly Thr Thr Val Thr Val Ser Ser
            115                 120

<210> SEQ ID NO 67
<211> LENGTH: 372
<212> TYPE: DNA
<213> ORGANISM: Homo sapiens

<400> SEQUENCE: 67
caggtgcagc tgcaggagtc gggcccagga ctggtgaagc cttcggagac cctgtccctc    60
acctgcactg tctctggtgg ctccatcagt agttactact ggacctggat ccggcagccc   120
gccgggaagg gactggagtg gattggcgt atctatacca gtggaatcac caactacaat   180
ccctccctca agagtcgcgt caccatgtca gtagacacgt ccaagaacca gttctccctg   240
aagctgagct ctgtgaccgc cgcggacacg gccgtgtatt actgtgcgag agagcgggta   300
gtgggagcta gtaggtacta ctactacggt gtggacgtct ggggccaagg gaccacggtc   360
accgtctcct cc                                                      372

<210> SEQ ID NO 68
<211> LENGTH: 124
<212> TYPE: PRT
<213> ORGANISM: Homo sapiens

<400> SEQUENCE: 68

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Ser Trp Ser Trp Ile Arg Gln Pro Ala Gly Lys Gly Leu Glu Trp Ile
             35                  40                  45

Gly Arg Thr Ser Thr Ser Gly Arg Asn Asn Tyr Asn Pro Ser Leu Lys
        50                  55                  60

Ser Arg Val Thr Met Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Asp Phe Thr Ile Ala Ala Arg Arg Tyr Tyr Tyr Gly Met Asp
                100                 105                 110

Val Trp Gly Gln Gly Thr Thr Val Thr Val Ser Ser
            115                 120

<210> SEQ ID NO 69
<211> LENGTH: 372
<212> TYPE: DNA
<213> ORGANISM: Homo sapiens

<400> SEQUENCE: 69
caggtgcagt tgcaggagtc gggcccagga ctggtgaagc cttcggagac cctgtccctc    60

```
acctgcactg tctctggtgg ctccatcagt agttactcct ggagctggat ccggcagccc      120
gccgggaagg gactggagtg gattgggcgt accagtacca gtgggagaaa caactacaac      180
ccctccctca agagtcgagt caccatgtca gttgacacgt ccaagaacca gttctccctg      240
aagctgaact ctgtgaccgc cgcggacacg gccgtgtatt actgtgcgag agatttcact      300
atagcagctc gtcgctacta ctactacggt atggacgtct ggggccaagg gaccacggtc      360
accgtctcct ca                                                          372
```

<210> SEQ ID NO 70
<211> LENGTH: 124
<212> TYPE: PRT
<213> ORGANISM: Homo sapiens

<400> SEQUENCE: 70

```
Gln Val Gln Leu Gln Glu Ser Gly Pro Arg Leu Val Lys Pro Ser Glu
  1               5                  10                  15

Thr Leu Ser Leu Thr Cys Thr Val Ser Gly Gly Ser Ile Thr Asn Asn
             20                  25                  30

Tyr Trp Ser Trp Ile Arg Gln Pro Ala Gly Lys Gly Leu Glu Trp Ile
         35                  40                  45

Gly Arg Val Tyr Ser Ser Gly Leu Thr Asn Tyr Lys Pro Ser Leu Lys
     50                  55                  60

Ser Arg Val Thr Met Ser Val Asp Thr Ser Lys Asn Gln Phe Ser Leu
 65                  70                  75                  80

Arg Leu Asn Ser Val Thr Ala Ala Asp Thr Ala Val Tyr Tyr Cys Ala
                 85                  90                  95

Arg Glu Arg Ala Thr Val Thr Thr Arg Tyr His Tyr Asp Gly Met Asp
            100                 105                 110

Val Trp Gly Gln Gly Thr Ser Val Thr Val Ser Ser
        115                 120
```

<210> SEQ ID NO 71
<211> LENGTH: 372
<212> TYPE: DNA
<213> ORGANISM: Homo sapiens

<400> SEQUENCE: 71

```
caggtgcagc tgcaggagtc gggcccaaga ctggtgaagc cttcggagac cctgtccctc       60
acctgcactg tctctggtgg ctccatcact aataactact ggagctggat ccggcagccc      120
gccgggaagg ggctggagtg gattgggcgt gtctatagta gtggactcac caactacaag      180
ccctccctca agagtcgagt caccatgtca gtagacacgt ccaagaacca attctccctg      240
aggttgaact ctgtgaccgc cgcggacacg gccgtgtatt actgtgcgag agagagggca      300
acagtaacta cgaggtacca ctacgacggt atggacgtct ggggccaagg gacctcggtc      360
accgtctcct ca                                                          372
```

<210> SEQ ID NO 72
<211> LENGTH: 124
<212> TYPE: PRT
<213> ORGANISM: Homo sapiens

<400> SEQUENCE: 72

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30
```

Tyr Trp Ser Trp Ile Arg Gln Pro Ala Gly Lys Gly Leu Glu Trp Ile
            35                  40                  45

Gly Arg Ile Phe Ala Ser Gly Ser Thr Asn Tyr Asn Pro Ser Leu Arg
        50                  55                  60

Ser Arg Val Thr Met Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Glu Arg Val Gly Val Gln Asp Tyr Tyr His Tyr Ser Gly Met Asp
            100                 105                 110

Val Trp Gly Gln Gly Thr Thr Val Thr Val Ser Ser
        115                 120

<210> SEQ ID NO 73
<211> LENGTH: 372
<212> TYPE: DNA
<213> ORGANISM: Homo sapiens

<400> SEQUENCE: 73
caggtgcagc tgcaggagtc gggcccagga ctggtgaagc cttcggagac cctgtccctc    60
acttgcactg tctctggtgg ctccatcagt agttactact ggagctggat ccggcagccc   120
gccgggaagg gactggagtg gattgggcgc atctttgcca gtgggagcac caactacaac   180
ccctccctca ggagtcgagt caccatgtca agagacacgt ccaagaacca gttctccctg   240
aagctgagtt ctgtgaccgc cgcggacacg gccgtttatt actgtgcgaa agaaagggtg   300
ggagtacagg attactacca ctattccggt atggacgtct ggggccaagg gaccacggtc   360
accgtctcct ca                                                      372

<210> SEQ ID NO 74
<211> LENGTH: 234
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Cytoplasmic
<220> FEATURE:
<221> NAME/KEY: MISC_FEATURE
<222> LOCATION: (38)..(62)
<223> OTHER INFORMATION: Transmembrane
<220> FEATURE:
<221> NAME/KEY: MISC_FEATURE
<222> LOCATION: (63)..(234)
<223> OTHER INFORMATION: Extracellular

<400> SEQUENCE: 74

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

```
Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile, Ser or Tyr
<220> FEATURE:
<221> NAME/KEY: MOD_RES
<222> LOCATION: (5)..(5)
<223> OTHER INFORMATION: Thr or Ser

<400> SEQUENCE: 75

Ser Tyr Xaa Trp Xaa
1               5

<210> SEQ ID NO 76
<211> LENGTH: 21
<212> TYPE: PRT
<213> ORGANISM: Homo sapiens

<400> SEQUENCE: 76

Asp Tyr Lys Asp Asp Asp Asp Lys His His His His His His Glu Asn
1               5                   10                  15

Leu Tyr Phe Gln Gly
            20

<210> SEQ ID NO 77
<211> LENGTH: 16
<212> TYPE: PRT
<213> ORGANISM: Homo sapiens

<400> SEQUENCE: 77

Phe Gln Tyr Ile Asp Thr Ser Thr Phe Pro Leu Glu Asn Val Leu Ser
1               5                   10                  15

<210> SEQ ID NO 78
<211> LENGTH: 21
<212> TYPE: PRT
<213> ORGANISM: Homo sapiens
```

<400> SEQUENCE: 78

Asp Tyr Lys Asp Asp Asp Lys His His His His His Glu Asn
1               5                   10                  15

Leu Tyr Phe Gln Gly
            20

<210> SEQ ID NO 79
<211> LENGTH: 40
<212> TYPE: PRT
<213> ORGANISM: Homo sapiens

<400> SEQUENCE: 79

Asp Tyr Lys Asp Asp Asp Lys His His His His His Glu Asn
1               5                   10                  15

Leu Tyr Phe Gln Gly Asp Ser Ile Pro Asn Ser Pro Asn Val Pro
            20                  25                  30

Leu Lys Gly Gly Asp Cys Ser Glu
35                  40

<210> SEQ ID NO 80
<211> LENGTH: 42
<212> TYPE: PRT
<213> ORGANISM: Homo sapiens

<400> SEQUENCE: 80

Asp Tyr Lys Asp Asp Asp Lys His His His His His Glu Asn
1               5                   10                  15

Leu Tyr Phe Gln Gly Asp Ser Ile Pro Asn Ser Pro Asn Val Pro
            20                  25                  30

Leu Lys Gly Gly Asp Cys Ser Glu Asp Leu
        35                  40

<210> SEQ ID NO 81
<211> LENGTH: 43
<212> TYPE: PRT
<213> ORGANISM: Homo sapiens

<400> SEQUENCE: 81

Asp Tyr Lys Asp Asp Asp Lys His His His His His Glu Asn
1               5                   10                  15

Leu Tyr Phe Gln Gly Asp Ser Ile Pro Asn Ser Pro Asn Val Pro
            20                  25                  30

Leu Lys Gly Gly Asp Cys Ser Glu Asp Leu Leu
        35                  40

<210> SEQ ID NO 82
<211> LENGTH: 20
<212> TYPE: PRT
<213> ORGANISM: Homo sapiens

<400> SEQUENCE: 82

Tyr Phe Gln Gly Asp Ser Ile Pro Asn Ser Pro Asn Val Pro Leu
1               5                   10                  15

Lys Gly Gly Asp
            20

<210> SEQ ID NO 83
<211> LENGTH: 23
<212> TYPE: PRT
<213> ORGANISM: Homo sapiens -continued

```
<400> SEQUENCE: 83

Tyr Phe Gln Gly Asp Ser Ile Pro Asn Ser Pro Asp Asn Val Pro Leu
1               5                   10                  15

Lys Gly Gly Asp Cys Ser Glu
            20

<210> SEQ ID NO 84
<211> LENGTH: 24
<212> TYPE: PRT
<213> ORGANISM: Homo sapiens

<400> SEQUENCE: 84

Tyr Phe Gln Gly Asp Ser Ile Pro Asn Ser Pro Asp Asn Val Pro Leu
1               5                   10                  15

Lys Gly Gly Asp Cys Ser Glu Asp
            20

<210> SEQ ID NO 85
<211> LENGTH: 25
<212> TYPE: PRT
<213> ORGANISM: Homo sapiens

<400> SEQUENCE: 85

Tyr Phe Gln Gly Asp Ser Ile Pro Asn Ser Pro Asp Asn Val Pro Leu
1               5                   10                  15

Lys Gly Gly Asp Cys Ser Glu Asp Leu
            20                  25

<210> SEQ ID NO 86
<211> LENGTH: 26
<212> TYPE: PRT
<213> ORGANISM: Homo sapiens

<400> SEQUENCE: 86

Tyr Phe Gln Gly Asp Ser Ile Pro Asn Ser Pro Asp Asn Val Pro Leu
1               5                   10                  15

Lys Gly Gly Asp Cys Ser Glu Asp Leu Leu
            20                  25

<210> SEQ ID NO 87
<211> LENGTH: 27
<212> TYPE: PRT
<213> ORGANISM: Homo sapiens

<400> SEQUENCE: 87

Tyr Phe Gln Gly Asp Ser Ile Pro Asn Ser Pro Asp Asn Val Pro Leu
1               5                   10                  15

Lys Gly Gly Asp Cys Ser Glu Asp Leu Leu Cys
            20                  25

<210> SEQ ID NO 88
<211> LENGTH: 16
<212> TYPE: PRT
<213> ORGANISM: Homo sapiens

<400> SEQUENCE: 88

Asp Ser Ile Pro Asn Ser Pro Asp Asn Val Pro Leu Lys Gly Gly Asp
1               5                   10                  15

<210> SEQ ID NO 89
<211> LENGTH: 21
```

```
<212> TYPE: PRT
<213> ORGANISM: Homo sapiens

<400> SEQUENCE: 89

Asp Ser Ile Pro Asn Ser Pro Asp Asn Val Pro Leu Lys Gly Gly Asp
1               5                   10                  15

Cys Ser Glu Asp Leu
            20

<210> SEQ ID NO 90
<211> LENGTH: 22
<212> TYPE: PRT
<213> ORGANISM: Homo sapiens

<400> SEQUENCE: 90

Asp Ser Ile Pro Asn Ser Pro Asp Asn Val Pro Leu Lys Gly Gly Asp
1               5                   10                  15

Cys Ser Glu Asp Leu Leu
            20

<210> SEQ ID NO 91
<211> LENGTH: 16
<212> TYPE: PRT
<213> ORGANISM: Homo sapiens

<400> SEQUENCE: 91

Leu Cys Ile Leu Lys Arg Ala Pro Phe Lys Lys Ser Trp Ala Tyr Leu
1               5                   10                  15

<210> SEQ ID NO 92
<211> LENGTH: 15
<212> TYPE: PRT
<213> ORGANISM: Homo sapiens

<400> SEQUENCE: 92

Cys Ile Leu Lys Arg Ala Pro Phe Lys Lys Ser Trp Ala Tyr Leu
1               5                   10                  15

<210> SEQ ID NO 93
<211> LENGTH: 14
<212> TYPE: PRT
<213> ORGANISM: Homo sapiens

<400> SEQUENCE: 93

Ile Leu Lys Arg Ala Pro Phe Lys Lys Ser Trp Ala Tyr Leu
1               5                   10

<210> SEQ ID NO 94
<211> LENGTH: 12
<212> TYPE: PRT
<213> ORGANISM: Homo sapiens

<400> SEQUENCE: 94

Lys Arg Ala Pro Phe Lys Lys Ser Trp Ala Tyr Leu
1               5                   10

<210> SEQ ID NO 95
<211> LENGTH: 29
<212> TYPE: PRT
<213> ORGANISM: Homo sapiens

<400> SEQUENCE: 95

Gln Val Ala Lys His Leu Asp Lys Thr Lys Leu Ser Trp Asn Lys Asp
1               5                   10                  15
```

Gly Ile Leu His Gly Val Arg Tyr Gln Asp Gly Asn Leu
            20                  25

<210> SEQ ID NO 96
<211> LENGTH: 27
<212> TYPE: PRT
<213> ORGANISM: Homo sapiens

<400> SEQUENCE: 96

Ala Lys His Leu Asp Lys Thr Lys Leu Ser Trp Asn Lys Asp Gly Ile
1               5                   10                  15

Leu His Gly Val Arg Tyr Gln Asp Gly Asn Leu
            20                  25

<210> SEQ ID NO 97
<211> LENGTH: 8
<212> TYPE: PRT
<213> ORGANISM: Homo sapiens

<400> SEQUENCE: 97

Ser Trp Asn Lys Asp Gly Ile Leu
1               5

<210> SEQ ID NO 98
<211> LENGTH: 16
<212> TYPE: PRT
<213> ORGANISM: Homo sapiens

<400> SEQUENCE: 98

Ser Trp Asn Lys Asp Gly Ile Leu His Gly Val Arg Tyr Gln Asp Gly
1               5                   10                  15

<210> SEQ ID NO 99
<211> LENGTH: 18
<212> TYPE: PRT
<213> ORGANISM: Homo sapiens

<400> SEQUENCE: 99

Ser Trp Asn Lys Asp Gly Ile Leu His Gly Val Arg Tyr Gln Asp Gly
1               5                   10                  15

Asn Leu

<210> SEQ ID NO 100
<211> LENGTH: 7
<212> TYPE: PRT
<213> ORGANISM: Homo sapiens

<400> SEQUENCE: 100

Val Ile Gln Phe Pro Gly Leu
1               5

<210> SEQ ID NO 101
<211> LENGTH: 8
<212> TYPE: PRT
<213> ORGANISM: Homo sapiens

<400> SEQUENCE: 101

Val Ile Gln Phe Pro Gly Leu Tyr
1               5

<210> SEQ ID NO 102
<211> LENGTH: 9
<212> TYPE: PRT

<213> ORGANISM: Homo sapiens

<400> SEQUENCE: 102

Val Ile Gln Phe Pro Gly Leu Tyr Phe
1               5

<210> SEQ ID NO 103
<211> LENGTH: 10
<212> TYPE: PRT
<213> ORGANISM: Homo sapiens

<400> SEQUENCE: 103

Leu Val Gln Cys Pro Gln Asn Ser Val Asp
1               5                   10

<210> SEQ ID NO 104
<211> LENGTH: 5
<212> TYPE: PRT
<213> ORGANISM: Homo sapiens

<400> SEQUENCE: 104

Leu Lys Leu Glu Leu
1               5

<210> SEQ ID NO 105
<211> LENGTH: 11
<212> TYPE: PRT
<213> ORGANISM: Homo sapiens

<400> SEQUENCE: 105

Leu Ile Asn Lys His Ile Lys Lys Gln Ala Leu
1               5                   10

<210> SEQ ID NO 106
<211> LENGTH: 13
<212> TYPE: PRT
<213> ORGANISM: Homo sapiens

<400> SEQUENCE: 106

Leu Ile Asn Lys His Ile Lys Lys Gln Ala Leu Val Thr
1               5                   10

<210> SEQ ID NO 107
<211> LENGTH: 17
<212> TYPE: PRT
<213> ORGANISM: Homo sapiens

<400> SEQUENCE: 107

Val Thr Val Cys Glu Ser Gly Met Gln Thr Lys His Val Tyr Gln Asn
1               5                   10                  15
Leu

<210> SEQ ID NO 108
<211> LENGTH: 19
<212> TYPE: PRT
<213> ORGANISM: Homo sapiens

<400> SEQUENCE: 108

Val Thr Val Cys Glu Ser Gly Met Gln Thr Lys His Val Tyr Gln Asn
1               5                   10                  15
Leu Ser Gln

<210> SEQ ID NO 109

```
<211> LENGTH: 20
<212> TYPE: PRT
<213> ORGANISM: Homo sapiens

<400> SEQUENCE: 109

Val Thr Val Cys Glu Ser Gly Met Gln Thr Lys His Val Tyr Gln Asn
1               5                   10                  15

Leu Ser Gln Phe
            20

<210> SEQ ID NO 110
<211> LENGTH: 15
<212> TYPE: PRT
<213> ORGANISM: Homo sapiens

<400> SEQUENCE: 110

Val Cys Glu Ser Gly Met Gln Thr Lys His Val Tyr Gln Asn Leu
1               5                   10                  15

<210> SEQ ID NO 111
<211> LENGTH: 12
<212> TYPE: PRT
<213> ORGANISM: Homo sapiens

<400> SEQUENCE: 111

Phe Gln Tyr Ile Asp Thr Ser Thr Phe Pro Leu Glu
1               5                   10

<210> SEQ ID NO 112
<211> LENGTH: 15
<212> TYPE: PRT
<213> ORGANISM: Homo sapiens

<400> SEQUENCE: 112

Phe Gln Tyr Ile Asp Thr Ser Thr Phe Pro Leu Glu Asn Val Leu
1               5                   10                  15

<210> SEQ ID NO 113
<211> LENGTH: 10
<212> TYPE: PRT
<213> ORGANISM: Homo sapiens

<400> SEQUENCE: 113

Tyr Ile Asp Thr Ser Thr Phe Pro Leu Glu
1               5                   10

<210> SEQ ID NO 114
<211> LENGTH: 13
<212> TYPE: PRT
<213> ORGANISM: Homo sapiens

<400> SEQUENCE: 114

Tyr Ile Asp Thr Ser Thr Phe Pro Leu Glu Asn Val Leu
1               5                   10

<210> SEQ ID NO 115
<211> LENGTH: 14
<212> TYPE: PRT
<213> ORGANISM: Homo sapiens

<400> SEQUENCE: 115

Tyr Ile Asp Thr Ser Thr Phe Pro Leu Glu Asn Val Leu Ser
1               5                   10
```

```
<210> SEQ ID NO 116
<211> LENGTH: 9
<212> TYPE: PRT
<213> ORGANISM: Homo sapiens

<400> SEQUENCE: 116

Ser Thr Phe Pro Leu Glu Asn Val Leu
1               5

<210> SEQ ID NO 117
<211> LENGTH: 7
<212> TYPE: PRT
<213> ORGANISM: Homo sapiens

<400> SEQUENCE: 117

Cys Ser Glu Asp Leu Leu Cys
1               5
```